US008968702B2

United States Patent
Li et al.

(10) Patent No.: US 8,968,702 B2
(45) Date of Patent: Mar. 3, 2015

(54) INHIBITION OF HIF-1 ACTIVATION FOR ANTI-TUMOR AND ANTI-INFLAMMATORY RESPONSES

(75) Inventors: Chuan-Yuan Li, Englewood, CO (US); Fang Li, Greenwood Village, CO (US); Pierre Sonveaux, Ottignies-Louvain-la-Neuve (BE); Mark W. Dewhirst, Durham, NC (US)

(73) Assignee: Duke University, Durham, NC (US)

( * ) Notice: Subject to any disclaimer, the term of this patent is extended or adjusted under 35 U.S.C. 154(b) by 342 days.

(21) Appl. No.: 11/731,719

(22) Filed: Mar. 30, 2007

(65) Prior Publication Data

US 2007/0297984 A1 Dec. 27, 2007

Related U.S. Application Data

(60) Provisional application No. 60/787,373, filed on Mar. 30, 2006.

(51) Int. Cl.
*A61K 49/00* (2006.01)
*C12N 5/00* (2006.01)
*C12N 5/02* (2006.01)
*A61K 41/00* (2006.01)
*A61K 45/06* (2006.01)

(52) U.S. Cl.
CPC ............ *A61K 41/0038* (2013.01); *A61K 45/06* (2013.01)
USPC ........................................... 424/9.2; 435/375

(58) Field of Classification Search
None
See application file for complete search history.

(56) References Cited

U.S. PATENT DOCUMENTS

| 5,114,951 | A | | 5/1992 | King |
| 5,410,016 | A | | 4/1995 | Hubbell et al. |
| 5,411,554 | A | | 5/1995 | Scopelianos et al. |
| 5,468,253 | A | | 11/1995 | Bezwada et al. |
| 5,554,638 | A | * | 9/1996 | Dewhirst et al. ............. 514/398 |
| 5,573,934 | A | | 11/1996 | Hubbell et al. |

(Continued)

FOREIGN PATENT DOCUMENTS

| WO | WO97/47763 | 12/1997 |
| WO | WO99/07409 | 2/1999 |

(Continued)

OTHER PUBLICATIONS

Salvucci et al. (Antiapoptotic Role of Endogenous Nitric Oxide in Human Melanoma Cells; Cancer Research 61, 318-326, Jan. 1, 2001).*

(Continued)

*Primary Examiner* — Trevor Love
(74) *Attorney, Agent, or Firm* — Jenkins, Wilson, Taylor & Hunt, P.A.

(57) ABSTRACT

The presently disclosed subject matter generally relates to methods and compositions for inhibiting the expression and/or activation of hypoxia-inducible factor 1 (HIF-1) genes in a hypoxic cell. More particularly, the methods disclosed herein relate to inhibition of HIF-1 activation in a cell, increasing sensitivity of a tumor cell to radiation and/or chemotherapy, delaying tumor growth, inhibiting tumor blood vessel growth, inhibiting inflammatory responses in a cell through the use of compositions that prevent the nitrosylation of HIF-1, and methods for screening for new inhibitors of HIF-1 activiation. Additionally, the compositions disclosed herein relate to compositions that can be employed in, and are identified by, the disclosed methods.

6 Claims, 23 Drawing Sheets
(2 of 23 Drawing Sheet(s) Filed in Color)

(56) References Cited

U.S. PATENT DOCUMENTS

| | | | |
|---|---|---|---|
| 5,599,852 A | 2/1997 | Scopelianos et al. | |
| 5,612,310 A | 3/1997 | Dewhirst et al. | |
| 5,631,015 A | 5/1997 | Bezwada et al. | |
| 5,653,992 A | 8/1997 | Bezwada et al. | |
| 5,677,350 A * | 10/1997 | Frydman | 514/655 |
| 5,688,900 A | 11/1997 | Cooper et al. | |
| 5,713,920 A | 2/1998 | Bezwada et al. | |
| 5,728,752 A | 3/1998 | Scopelianos et al. | |
| 5,788,958 A | 8/1998 | Dewhirst et al. | |
| 5,824,333 A | 10/1998 | Scopelianos et al. | |
| 5,858,746 A | 1/1999 | Hubbell et al. | |
| 5,858,784 A | 1/1999 | Debs et al. | |
| 5,916,910 A * | 6/1999 | Lai | 514/423 |
| 6,013,638 A | 1/2000 | Crystal et al. | |
| 6,020,308 A | 2/2000 | Dewhirst et al. | |
| 6,022,737 A | 2/2000 | Niven et al. | |
| 6,136,295 A | 10/2000 | Edwards et al. | |
| 6,946,484 B2 | 9/2005 | Adams et al. | |
| 7,009,034 B2 | 3/2006 | Pathak et al. | |
| 7,011,842 B1 | 3/2006 | Simhambhatla et al. | |
| 7,012,126 B2 | 3/2006 | Matsuda et al. | |
| 2003/0215528 A1 | 11/2003 | Graham et al. | |
| 2011/0054023 A1 | 3/2011 | Dewhirst | |

FOREIGN PATENT DOCUMENTS

| | | |
|---|---|---|
| WO | WO99/32619 | 7/1999 |
| WO | WO00/01846 | 1/2000 |
| WO | WO00/44895 | 8/2000 |
| WO | WO00/44914 | 8/2000 |
| WO | WO01/29058 | 4/2001 |
| WO | WO01/36646 | 5/2001 |

OTHER PUBLICATIONS

Ruiz et al. (S-nitrosylation: a potential new paradigm in signal transduction; Cardiovascular Research 62 (2004) 43-52.*
Moeller et al.(Pleiotropic effects of HIF-1 blockade on tumor radiosensitivity: Cancer Cell; Aug. 2005, vol. 8, pp. 99-110) and Frydman (US Patent No. 5,677,350 ; issued on Oct. 14, 1997).*
Metzen et al. (Nitric Oxide Impairs Normoxic Degredation of HIF-1alpha by Inhibition of Prolyl Hydroxylases; Molecular Biology of the Cell, vol. 14, 3470-3481, Aug. 2003).*
Esho, FAQ—Frequently Asked Questions, Jul. 13, 2003, http://www.esho.info/patients/faqs.html#13artikel, accessed through Wayback Machine: https://web.archive.org/web/20030713204658/http://esho.info/patients/faqs.html, pp. 1-7.*
Hildebrandt et al, Inhibition of the iNOS Pathway in Inflammatory Macrophages by Low-Dose X-Irradiation in Vitro, 2003, Strahlentherapie and Onkologie, No. 3, pp. 158-166.*
Notification of Transmittal of the International Search Report and the Written Opinion of the International Searching Authority, or the Declaration corresponding to International Patent Application No. PCT/US07/08034 dated Jul. 29, 2008.
Acker (1998). Serial in vivo observations of cerebral vasculature after treatment with a large single fraction of radiation. Rad Research. 149: 350-359.
Alderton et al. (2001). Nitric oxide synthases: structure, function and inhibition. Biochem J 357:593-615.
Barr et al. (2008). Vascular endothelial growth factor is an autocrine survival factor for breast tumour cells under hypoxia. Int J Oncol. 32:41-48.
Berchner-Pfannschmidt et al (2007). Nitric oxide modulates oxygen sensing by hypoxia-inducible factor 1-dependent induction of prolyl hydroxylase 2. J Biol Chem 282: 1788-1796.
Bertout (2008). The impact of O2 availability on human cancer. Nat Rev Cancer 8: 967-975.
Brizel et al. (1996). Radiation therapy and hyperthermia improve the oxygenation of human soft tissue sarcomas.Cancer Res. 56:5347-5350.
Chen et al. (2003). Direct interactions between HIF-1 alpha and Mdm2 modulate p53 function. J Biol Chem 278:13595-13598.
Cho et al. (2004). Oncolytic Effects of Adenovirus Mutant Capable of Replicating in Hypoxic and Normoxic Regions of Solid Tumor. Molecular Therapy 10(5): 938-949.
Cho et al. (1994). Crystal structure of a p53 tumor suppressor-DNA complex: understanding tumorigenic mutations. Science. 265: 346-355.
Cockman et al. (2000). Hypoxia inducible factor-alpha binding and ubiquitylation by the von Hippel-Lindau tumor suppressor protein. J Biol Chem. 275:25733-25741.
Colombo & Mantovani (2005). Targeting myelomonocytic cells to revert inflammation-dependent cancer promotion. Cancer Res 65:9113-9116.
Comerford et al. (2002). Hypoxia-inducible factor-1-dependent regulation of the multidrug resistance (MDR1) gene. Cancer Res. 62:3387-3394.
Cramer et al. (2003). HIF-1alpha is essential for myeloid cell-mediated inflammation. Cell. 112:645-657.
Forsythe et al. (1996). Activation of vascular endothelial growth factor gene transcription by hypoxia-inducible factor 1. Mol Cell Biol 16:4604-4613.
Fukuda et al. (2002). Insulin-like growth factor 1 induces hypoxia-inducible factor 1-mediated vascular endothelial growth factor expression, which is dependent on MAP kinase and phosphatidylinositol 3-kinase signaling in colon cancer cells. J Biol Chem. 277:38205-38211.
Fukuda et al. (2003). Vascular endothelial growth factor gene expression in colon cancer cells exposed to prostaglandin E2 is mediated by hypoxia-inducible factor 1. Cancer Res. 63:2330-2334.
Genbank® Accession No. AAA62405, Feb. 24, 1995. Hall, et al. (1994). Structural organization of the human neuronal nitric oxide synthase gene. J Biol Chem. 269(52):33082-33090.
Genbank® Accession No. AAH69465, Jul. 15, 2006. Strausberg et al. (2002). Generation and initial analysis of more than 15,000 full-length human and mouse cDNA sequences. Proc Natl Acad Sci USA. 99(26):16899-16903.
Genbank® Accession No. AAP43517, Jun. 30, 2005. Clausen et al. (2005). Lineage-specific effects of polychlorinated biphenyls (PCB) on gene expression in the rabbit blastocyst. Reprod Toxicol. 20(1):47-56.
Genbank® Accession No. AAU14021, May 27, 2005. Morin, et al. (2005). Cloning and expression of hypoxia-inducible factor 1alpha from the hibernating ground squirrel, *Spermophilus tridecemlineatus*. Biochem Biophys. Acta 1729(1):32-40.
Genbank® Accession No. AAX89137, Jul. 18, 2006. Xie et al. Cloning of HIF-1 alpha cDNA from Tibetan antelope. Unpublished.
Genbank® Accession No. AAY27087, May 10, 2005. Xie et al. Cloning of hypoxia-inducible factor 1 alpha cDNA from root bole. Unpublished.
Genbank® Accession No. ABB17537, Apr. 2, 2007. Chen et al. Cloning of hypoxia-inducible factor 1 alpha from plateau zokor (*Myospalax* baileyi). Unpublished.
Genbank® Accession Nos. BAE01417, Oct. 6, 2006. Osada et al. DNA sequences of macaque genes expressed in brain or testis and its evolutionary implications. Unpublished.
Genbank® Accession No. BC069465, Jul. 15, 2006. Stausberg et al. (2002) Generation and initial analysis of more than 15,000 full-length human and mouse cDNA sequences. Proc Natl Acad Sci USA. 99(26): 16899-16903.
Genbank® Accession No. CAB96628, Apr. 15, 2005. Kietzman . Cloning and expression of the *Xenopus laevis* hypoxia inucible factor 1 alpha homologue. Unpublished.
Genbank® Accession No. CAG29396, Jan., 26, 2006. Shams et al. (2004). Hypoxic stress tolerance of the blind subterranean mole rat: expression of erythropoietin and hypoxia-inducible factor 1 alpha. Proc. Natl. Acad. Sci. USA. 101(26):9698-9703.
Genbank® Accession No. CAH93355, Oct. 7, 2008. Wambutt et al. Unpublished.
Genbank® Accession No. NM_000625, Jun. 10, 2012. Guo et al. (2012). miRNA-939 regulates human inducible nitric oxide synthase posttranscriptional gene expression in human hepatocytes. Proc. Nat. Acad. Sci. USA. 109(15): 5826-5831.

(56) References Cited

OTHER PUBLICATIONS

Genbank® Accession No. NP_000616, Jun. 10, 2012. Guo et al. (2012). miRNA-939 regulates human inducible nitric oxide synthase posttranscriptional gene expression in human hepatocytes. Proc. Natl. Acad. Sci. USA. 109(15): 5826-5831.
Genbank® Accession No. NP_001521, Jun. 10, 2012. Carbonaro et al. (2012). Microtubules regulate hypoxia-inducible factor-1 alpha protein trafficking and activity: implications for taxane therapy. J Biol Chem 287(15):11859-11869.
Genbank® Accession No. NP_034561, Jun. 9, 2012. Wei et al. Endothelial expression of hypoxia-inducible factor 1 protects the murine heart and aorta from pressure overload by suppression of TGF-beta signaling. J Biol Chem 287(13): 9659-9671.
Genbank® Accession No. NP_077335, Jun. 3, 2012. Sparkenbaugh et al. (2012). Hypoxia sensitization of hepatocytes to neurtrophil elastase-mediated cell death depends on MAPKs and HIF-1alpha. Am J Physiol Gastrointest Liver Physiol 302(7): G748-G757.
Genbank® Accession No. NP_776764, Mar. 25, 2012. Mattmiller et al. (2011). Glucose transporter and hypoxia-associated gene expression in the mammary gland of transition dairy cattle. J Dairy Sci. 94(6):2912-2922.
Genbank® Accession No. NP_956527, Jun. 10, 2012. Stevenson et al. (2012). Hypoxia disruption of vertebrate CNS pathfinding through ephrinB2 is rescued by magnesium. PLoS Genet. 8(4): E1002738.
Genbank® Accession No. NP_989628, Apr. 21, 2012. Wikenheiser et al. (2009). Altered hypoxia-inducible factor-1 alpha expression levels correlate with coronary vessel anomalies. Dev. Dyn. 238(10): 2688-2700.
Genbank® Accession No. P74553, Oct. 31, 2006. Kaneko et al. (1996). Sequence analysis of the genome of the unicellular cyanobacterium *Synechocystis* sp. Strain PCC6803. II. Sequence determination of the entire genome and assignment of potential protein-coding regions. DNA Res. 3(3):109-136.
Genbank® Accession No. HSU17327, Feb. 24, 1995. Hall et al. (1994). Strutural organization of the human neuronal nitric oxide synthase gene (NOS1). J Biol Chenn 269(52):33082-33090.
Genbank® Accession No. MMU59496, Aug. 30, 1996. Induction of phosphoglycerate kinase 1 gene expression by hypoxia. Roles of Arnt and HIFalpha. Ju Bil Chem. 271(35):21262-21267.
Generali et al (2006). Hypoxia-inducible factor-1alpha expression predicts a poor response to primary chemoendocrine therapy and disease-free survival in primary human breast cancer. Clin Cancer Res 12: 4562-4568.
Goldmann et al. (2004). Role of macrophages in host resistance to group A streptococci. Infect Immun. 72:2956-2963.
Gruber et al. (2004). Hypoxia-inducible factor 1 alpha in high-risk breast cancer: an independent prognostic parameter? Breast Cancer Res. 6:R191-198.
Guo et al. (2008) Osteopontin mediates Stat1 degradation to inhibit iNOS transcription in a cecal ligation and puncture model of sepsis. Surgery. 144:182-188.
Hagen et al. (2003). Redistribution of intracellular oxygen in hypoxia by nitric oxide: effect on HIF1alpha. Science. 302:1975-1978.
Isaacs et al. (2005). HIF overexpression correlates with biallelic loss of fumarate hydratase in renal cancer: novel role of fumarate in regulation of HIF stability. Cancer Cell. 8:143-153.
Ivan et al. (2001). HIFalpha targeted for VHL-mediated destruction by proline hydroxylation: implications for O2 sensing. Science. 292:464-468.
Iwashina et al. (1998). Transfection of inducible nitric oxide synthase gene causes apoptosis in vascular smooth muscle cells. Circulation. 98: 1212-1218.
Jiang et al. (1997). V-SRC induces expression of hypoxia-inducible factor 1 (HIF-1) and transcription of genes encoding vascular endothelial growth factor and enolase 1: involvement of HIF-1 in tumor progression. Cancer Res. 57:5328-5335.
Jung et al. (2000). Hypoxic regulation of inducible nitric oxide synthase via hypoxia inducible factor-1 in cardiac myocytes. Circ Res. 86:319-325.

Jung et al. (2000). Correction to: Hypoxic regulation of inducible nitric oxide synthase via hypoxia inducible factor-1 in cardiac myocytes. Circ Res. 86:319-325.
Kamura et al. (2000). Activation of HIF1alpha ubiquitination by a reconstituted von Hippel-Lindau (VHL) tumor suppressor complex.
Karlin & Altschul (1993). Applications and statistics for multiple high-scoring segments in molecular sequences. Proc Natl Acad Sci USA. 90:5873-5877.
Keith et al. (2007). Hypoxia-inducible factors, stem cells, and cancer. Cell. 129:465-472.
Kim et al. (2005). Inducible nitric oxide synthase binds, S-nitrosylates, and activates cyclooxygenase-2. Science 310:1966-1970.
Kim et al. (2009). Brain arteriovenous malformation biology relevant to hemorrhage and implication for therapeutic development. Stroke. S95-S97.
Kimura et al. (2000). Hypoxia response element of the human vascular endothelial growth factor gene mediates transcriptional regulation by nitric oxide: control of hypoxia-inducible factor-1 activity by nitric oxide. Blood. 95:189-197.
Krishnamachary et al. (2003). Regulation of colon carcinoma cell invasion by hypoxia-inducible factor 1. Cancer Res. 63:1138-1143.
Kurihara et al. (2000). Selectivity of a replication-competent adenovirus for human breast carcinoma cells expressing the MUC1 antigen. J Clin Invest. 106:763-771.
Lando et al. (2002). FIH-1 is an asparaginyl hydroxylase enzyme that regulates the transcriptional activity of hypoxia-inducible factor. Genes Dev. 16:1466-1471.
Laughner et al. (2001). HER2 (neu) signaling increases the rate of hypoxia-inducible factor 1alpha (HIF-1alpha) synthesis: novel mechanism for HIF-1-mediated vascular endothelial growth factor expression. Mol Cell Biol.21:3995-4004.
Lee et al. (2007). Vascular endothelial growth factor mediates intracrine survival in human breast carcinoma cells through internally expressed VEGFR1/FLT1. PLoSMed. 4:e186.
Lee et al. (2009). Anthracycline chemotherapy inhibits HIF-1 transcriptional activity and tumor-induced mobilization of circulating arlgiogenic cells. Proc Natl Acad Sci USA. 106:2353-2358.
Leek et al. (2002). Relation of hypoxia-inducible factor-2 alpha (HIF-2 alpha) expression in tumor-infiltrative macrophages to tumor angiogenesis and the oxidative thymidine phosphorylase pathway in Human breast cancer. Cancer Res. 62:1326-1329.
Li et al. (2009). Hypoxia-inducible factors regulate tumorigenic capacity of glioma stem cells. Cancer Cell. 15:501-513.
Liao et al. (2007). Hypoxia-inducible factor-1alpha is a key regulator of metastasis in a transgenic model of cancer initiation and progression. Cancer Res. 67:563-572.
Liu et al, (1998). Inhibition of Stat1-mediated gene activation by PIAS1. Proc Natl Acad Sci. USA. 95:10626-10631.
Lewis & Murdoch (2005). Macrophage responses to hypoxia: implications for tumor progression and anti-cancer therapies. Am J Pathol. 167:627-635.
Li et al. (2007). Regulation of HIF-1( Stability through S-Nitrosylation. Molecular Cell. 26:63-74 (Apr. 13, 2007).
Mateo et al. (2003). Regulation of hypoxia-inducible factor-1alpha by nitric oxide through mitochondria-dependent and -independent pathways. Biochem J. 376:537-544.
Maltepe et al. (1997). Abnormal angiogenesis and responses to glucose and oxygen deprivation in mice lacking the protein ARNT. Nature. 386:403-407.
Maxwell et al. (1997). Hypoxia-inducible factor-1 modulates gene expression in solid tumors and influences both angiogenesis and tumor growth. Proc Natl Acad Sci USA. 94:8104-8109.
Melillo et al. (1997). Functional requirement of the hypoxia-responsive element in the activation of the inducible nitric oxide synthase promoter by the iron chelator desferrioxamine. J Biol Chem. 272:12236-12243.
Melillo (2004). HIF-1; a target for cancer, ischemia and inflammation—too good to be true? Cell Cycle .3:154-155.
Nagasawa et al. (1995). Relationship between radiation-induced G1 phase arrest and p53 function in human tumor cells. Cancer Research. 55:1842-1846.

(56) References Cited

OTHER PUBLICATIONS

Nardinocchi et al. (2009). Inhibition of HIF-1alpha activity by homeodomain-interacting protein kinase-2 correlates with sensitization of chemoresistant cells to undergo apoptosis. Mol Cancer. 8:1.
Needleman & Wunsch (1970). A general method applicable to the search for similarities in the amino acid sequence of two proteins. J Mol Biol. 48:443-453.
Office Action corresponding to U.S. Appl. No. 12/924,620 dated Feb. 22, 2012.
Office Action corresponding to U.S. Appl. No. 12/924,620 dated Jun. 8, 2011.
Park et al. (2008). Nitric oxide donor, (+/−)-S-nitroso-N-acetylpenicillamine, stabilizes transactive hypoxia-inducible factor-1alpha by inhibiting von Hippel-Lindau recruitment and asparagine hydroxylation. Mol. Pharmacol. 74:236-245.
Pause et al. (1999). Studying interactions of four proteins in the yeast two-hybrid system: structural resemblence of the pVHL/elongin BC/hCUL-2 complex with the ubiquitin ligase complex SKP1/cullin/F-box protein. Proc Nat Acad Sci USA. 96:9533-9538.
Pearson & Lipman (1988). Improved tools for biological sequence comparison. Proc Natl Acad Sci USA. 85:2444-2448.
Peyssonnaux et al. (2005). HIF-1alpha expression regulates the bactericidal capacity of phagocytes. J Clin Invest.115:1806-1815.
Primeau et al. (2005). The distribution of the anticancer drug Doxorubicin in relation to blood vessels in solid tumors. Clin Cancer Res. 11:8782-8788.
Rankin et al. (2008). The role of hypoxia-inducible factors in tumorigenesis. Cell Death Differ. 15:678-685.
Rapisarda et al. (2002). Identification of small molecule inhibitors of hypoxia-inducible factor 1 transcriptional activation pathway. Cancer Res. 62:4316-4324.
Ravi et al. (2000). Regulation of tumor angiogenesis by p53-induced degradation of hypoxia-inducible factor 1alpha. Genes Dev. 14:34-44.
Rottenberg et al. (2007). Selective induction of chemotherapy resistance of mammary tumors in a conditional mouse model for hereditary breast cancer. Proc Natl Acad Sci USA. 104:12117-12122.
Sandau et al. (2001). Accumulation of HIF-1alpha under the influence of nitric oxide. Blood. 97:1009-1015.
Scharfmann et al. (1991). Long-term in vivo expression of retrovirus-mediated gene transfer in mouse fibroblast implants. Proc Natl Acad Sci USA. 88:4626-4630.
Shaked et al. (2008). Rapid chemotherapy-induced acute endothelial progenitor cell mobilization: implications for antiangiogenic drugs as chemosensitizing agents. Cancer Cell 14:263-273.
Sogawa et al. (1998). Inhibition of hypoxia-inducible factor 1 activity by nitric oxide donors in hypoxia. Proc Natl Acad Sci U S A. 95:7368-7373.
Sutphin et al. (2004). Dead cells don't form tumors: HIF-dependent cytotoxins. Cell Cycle. 3:160-163.
Sweeney et al. (2001). The antiangiogenic property of docetaxel is synergistic with a recombinant humanized monoclonal antibody against vascular endothelial growth factor or 2-methoxyestradiol but antagonized by endothelial growth factors. Cancer Res. 61:3369-3372.
Talks et al. (2000). The expression and distribution of the hypoxia-inducible factors HIF-1alpha and HIF-2alpha in normal human tissues, cancers, and tumor-associated macrophages. Am J. Pathol. 157:411-421.
Thomas et al. (2004). STAT1: a modulator of chemotherapy-induced apoptosis. Cancer Res. 64:8357-8364.
Thomsen et al. (1997). Selective inhibition of inducible nitric oxide synthase inhibits tumor growth in vivo: studies with 1400W, a novel inhibitor. Cancer Res. 57:3300-3304.
Tran et al. (2002). A role for survivin in chemoresistance of endothelial cells mediated by VEGF. Proc Natl Acad Sci USA. 99:4349-4354.
Udono et al. (1994). Cellular requirements for tumor-specific immunity elicited by heat shock proteins: tumor rejection antigen gp96 primes CD8+ T cells in vivo. Proc Natl Acad Sci U S A. 91:3077-3081.
Vanhoefer et al. (1997). Comparative antitumor efficacy of docetaxel and paclitaxel in nude mice bearing human tumor xenografts that overexpress the multidrug resistance protein (MRP). Ann Oncol. 8:1221-1228.
Wachsberger et al. (2003). Tumor response to ionizing radiation combined with antiangiogenesis or vascular targeting agents: exploring mechanisms of interaction. Clin Cancer Res 9:1957-1971.
Wang & Semenza (1993a). Characterization of hypoxia-inducible factor 1 and regulation of DNA binding activity by hypoxia. J Biol Chem. 268:21513-21518.
Wang & Semenza (1993b). General involvement of hypoxia-inducible factor 1 in transcriptional response to hypoxia. Proc Natl Acad Sci USA .90:4304-4308.
Wang & Semenza (1995). Purification and characterization of hypoxia-inducible factor 1. J Biol Chem. 270:1230-1237.
Williams et al. (1993) Human heat shock protein 70 (hsp70) protects murine cells from injury during metabolic stress. J Clin Invest 92:503-508.
Yeo et al. (2003). YC-1: a potential anticancer drug targeting hypoxia-inducible factor 1. J Natl Cancer Inst. 95:516-525.
Yu et al. (1998). Temporal, spatial, and oxygen-regulated expression of hypoxia-inducible factor-1 in the lung. Am J Physiol. 275:L818-826.
Yu et al. (1999). The addition of adenovirus type 5 region E3 enables calydon virus 787 to eliminate distant prostate tumor xenografts. Cancer Res. 59:4200-4203.
Zhang et al. (2004a). Tracking angiogenesis induced by skin wounding and contact hypersensitivity using a Vegfr2-luciferase transgenic mouse. Blood. 103:617-626.
Zhang et al. (2004b). Enhancement of hypoxia-induced tumor cell death in vitro and radiation therapy in vivo by use of small interfering RNA targeted to hypoxia-inducible factor-1alpha. Cancer Res. 64:8139-8142.
Zhong et al. (2000). Modulation of hypoxia-inducible factor 1alpha expression by the epidermal growth factor/phosphatidylinositol 3-kinase/PTEN/AKT/FRAP pathway in human prostate cancer cells: implications for tumor angiogenesis and therapeutics. Cancer Res. 60:1541-1545.
Zundel et al. (2000). Loss of PTEN facilitates HIF-1-mediated gene expression. Genes Dev 14:391-396.
Apte et al. (2009). J Labelled Compd Rad. 52:S408-S. (Abstract).
Bergers & Benjamin (2003). Tumorigenesis and the angiogenic switch. Nat Rev Cancer. 3:401-410.
Brizel et al. (1999). Oxygenation of head and neck cancer: changes during radiotherapy and impact on treatment outcome. Radiother Oncol. 53:113-117.
Brown et al. (2004). Exploiting tumour hypoxia in cancer treatment. Nat Rev Cancer. 4:437-447.
Brune et al. (2007). Hypoxia-inducible factor-1alpha under the control of nitric oxide. Methods Enzymol. 435: 463-478.
Carcereri de Prati et al. (2005). STAT1 as a new molecular target of anti-inflammatory treatment. Curr Med Chem. 12:1819-1828.
Chan et al. (2002). J Biol Chem 277:40112-40117.
Cipolla et al. (2000). Coarse spray delivery to a localized region of the pulmonary airways for gene therapy. Hum Gene Ther. 11:361-371.
Clinical Trials.gov, Phase II study of induction chemotherapy comprising doxorubicin and cisplatin followed by combretastatin A4 phosphate and radiotherapy in patients with newly diagnosed regionally advanced anaplastic thyroid cancer (Phase I portion of the study closed as of May 6, 2004), U.S. National Insitutes of Health, pp. 1-6. Printed Feb. 3, 2012.
Contag et al. (1998). Bioluminescent indicators in living mammals. Nat Med. 4:245-247.
Dachs et al. (1997). Targeting gene expression to hypoxic tumor cells. Nat Med. 3:515-520.
Dales et al. (2005). Overexpression of hypoxia-inducible factor HIF-1alpha predicts early relapse in breast cancer: retrospective study in a series of 745 patients. Int J Cancer. 116:734-739.

(56) References Cited

OTHER PUBLICATIONS

Denko (2008). Hypoxia, HIF1 and glucose metabolism in the solid tumour. Nat Rev Cancer 8:705-713.

Dewhirst et al. (2008). Cycling hypoxia and free radicals regulate angiogenesis and radiotherapy response. Nat Rev Cancer. 8:425-437.

Elbashir et al. (2001). Duplexes of 21-nucleotide RNAs mediate RNA interference in cultured mammalian cells. Nature. 411:494-498.

Fryknas et al. (2006). STAT1 signaling is associated with acquired crossresistance to doxorubicin and radiation in myeloma cell lines. Int J Cancer 120: 189-195.

Garcia-Barros et al. (2003). Tumor response to radiotherapy regulated by endothelial cell apoptosis. Science. 300:1155-1159.

Gasparini et al. (2001). Angiogenesis sustains tumor dormancy in patients with breast cancer treated with adjuvant chemotherapy.

Giaccia et al. (2003). HIF-1 as a target for drug development. Nat Rev Drug Discov. 2:803-811.

Greenberg et al. (1994). The rat probasin gene promoter directs hormonally and developmentally regulated expression of a heterologous gene specifically to the prostate in transgenic mice. Mol Endocrinol 8:230-239.

Gunning et al. (2007). Isoform selective inhibition of STAT1 or STAT3 homo-dimerization via peptidomimetic probes: structural recognition of STAT SH2 domains. Bioorg Med Chem Lett. 17:1875-1878.

Habib et al. (1999). A phase I/II study of hepatic artery infusion with wtp53-CMV-Ad in metastatic malignant liver tumours. Hum Gene Ther. 10:2019-2034.

Harris (2002). Hypoxia—a key regulatory factor in tumour growth. Nat Rev Cancer. 2:38-47.

Hon et al. (2002). Structural basis for the recognition of hydroxyproline in HIF-1 alpha by pVHL. Nature. 417:975-978.

Huang et al. (1999). Noninvasive visualization of tumors in rodent dorsal skin window chambers. Nat Biotechnol. 17:1033-1035.

Jeong et al. (2002). Regulation and destabilization of HIF-1alpha by ARD1-mediated acetylation. Cell. 111:709-720.

Lando et al. (2002b). Asparagine hydroxylation of the HIF transactivation domain a hypoxic switch. Science. 295:858-861.

Lechner et al. (2005). Inducible nitric oxide synthase (iNOS) in tumor biology: the two sides of the same coin. Semin Cancer Biol. 15:277-289.

Leek et al. (2000). Macrophage infiltration is associated with VEGF and EGFR expression in breast cancer. J Pathol. 190:430-436.

Matrone et al. (2004). HIF-1alpha reveals a binding activity to the promoter of iNOS gene after permanent middle cerebral artery occlusion. J Neurochem. 90:368-378.

Maxwell et al. (1999). The tumour suppressor protein VHL targets hypoxia-inducible factors for oxygen-dependent proteolysis. Nature 399:271-275.

Maxwell et al. (2001). The pVHL-hIF-1 system. A key mediator of oxygen homeostasis. Adv Exp Med Biol 502:365-376.

Min et al. (2002). Structure of an HIF-1alpha-pVHL complex: hydroxyproline recognition in signaling. Science. 296:1886-1889.

Minchinton et al. (2006). Drug penetration in solid tumours. Nat Rev Cancer. 6:583-592.

Mitra et al. (2006). Photodynamic therapy mediates the oxygen-independent activation of hypoxia-inducible factor 1alpha. Mol Cancer Ther. 5:3268-3274.

Moeller et al. (2004). Radiation activates HIF-1 to regulate vascular radiosensitivity in tumors: role of reoxygenation, free radicals, and stress granules. Cancer Cell 5:429-441.

Moeller et al. (2005). Pleiotropic effects of HIF-1 blockade on tumor radiosensitivity. Cancer Cell.8:99-110.

Muerkoster et al. (2006). Acquired chemoresistance in pancreatic carcinoma cells: induced secretion of IL-1beta and NO lead to inactivation of caspases. Oncogene. 25:3973-3981.

Muller et al. (2005). Inhibition of indoleamine 2,3-dioxygenase, an immunoregulatory target of the cancer suppression gene Bin1, potentiates cancer chemotherapy. Nat Med. 11:312-319.

Naka et al. (1997). Structure and function of a new STAT-induced STAT inhibitor. Nature. 387:924-929.

Ohh et al. (2000). Ubiquitination of hypoxia-inducible factor requires direct binding to the beta-domain of the von Hippel-Lindau protein. Nat Cell Biol 2:423-427.

Pipili-Synetos et al., (1993) Nitric Oxide is involved in the regulation of angiogenesis, Br. J. Pharmacol., 108, 855-857.

Samardzic (2001). STAT1 is required for iNOS activation, but not IL-6 production in murine fibroblasts. Cytokine. 13:179-182.

Sanchez-Puig et al. (2005). Binding of natively unfolded HIF-1alpha ODD domain to p53. Mol Cell. 17:11-21.

Semenza et al. (2000a). Hypoxia, HIF-1, and the pathophysiology of common human diseases. Adv Exp Med Biol. 475:123-130.

Semenza et al. (2000b). HIF-1: mediator of physiological and pathophysiological responses to hypoxia, J. Appl. Physiol. 88:1474-1480.

Smith & Waterman (1981) Adv Appl Math 2:482-489.

Song et al. (2006). Hypoxia-induced resistance to cisplatin and doxorubicin in non-small cell lung cancer is inhibited by silencing of HIF-1alpha gene. Cancer Chemother Pharmacoll. 58:776-784.

Speri et al. (2009). Natural product inhibitors of protein-protein interactions mediated by Src-family SH2 domains. Bioorg Med Chem Lett. 19:3305-3309.

Sumbayev et al. (2003). HIF-1 alpha protein as a target for S-nitrosation. FEBS Lett. 535:106-112.

Unruh et al. (2003). The hypoxia-inducible factor-1 alpha is a negative factor for tumor therapy. Oncogene. 22:3213-3220.

Wartenberg et al. (1998). Development of an intrinsic P-glycoprotein-mediated doxorubicin resistance in quiescent cell layers of large, multicellular prostate tumor spheroids. J Cancer 75:855-863.

Weigand et al. (2005). Angiogenesis. 8:197-204.

Yamaguchi et al. (2005). Expression of inducible nitric oxide synthase is significantly correlated with expression of vascular endothelial growth factor and dendritic cell infiltration in patients with advanced gastric carcinoma. Oncology. 68:471-478.

Yasinska & Sumbayev (2003). S-nitrosation of Cys-800 of HIF-1alpha protein activates its interaction with p300 and stimulates its transcriptional activity. FEBS Lett 549:105-109.

* cited by examiner

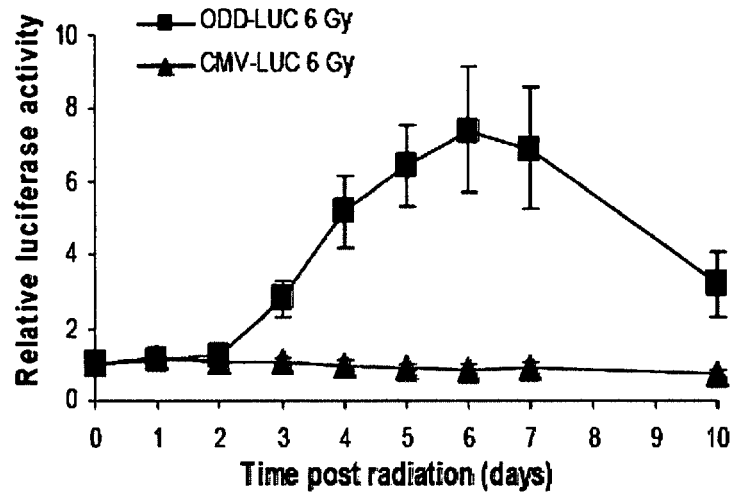
*Figure 2A*
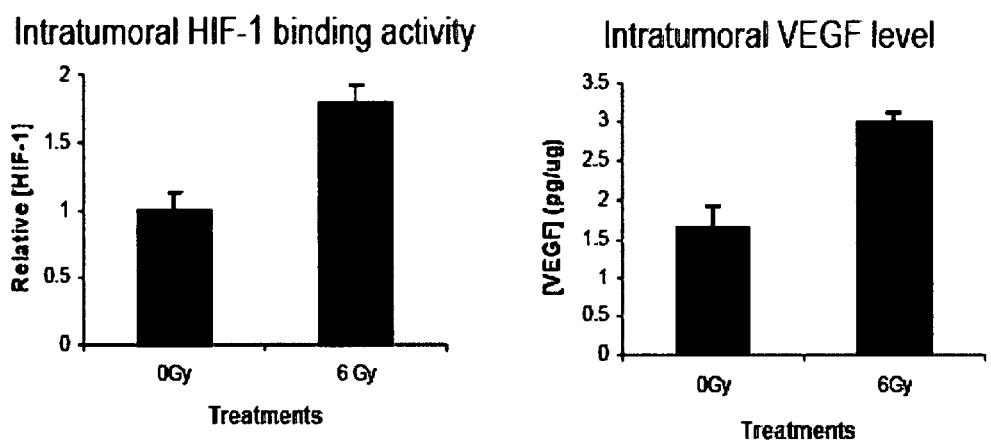
*Figure 2B*  *Figure 2C*

A

| | |
|---|---|
| pnspseycfyvdsdm | *Homo sapiens* (human) |
| pnspseycfdvdsdm | *Mus musculus* (house mouse) |
| pnspseycfdvdsdm | *Rattus norvegicus* (Norway rat) |
| pnspseycfdvdsdm | *Spalax judaei* (subterranean mole rat) |
| pnspseycfdvdsdm | *Bos grunniens* (domestic yak) |
| pnspmeycfqvdsdi | *Carassius carassius* (crucian carp) |
| epntpeycfdvdsem | *Xenopus laevis* (frog) |

B

C

D

E

F

A

B

```
Spalax         MEG-AGGENEKK-KMSSERRKEKSRDAARSRRSKESEVFYELAHQLPLPHNVSSHLDKAS   58
Eospalax       MEGAAGGEEKKN-RMSSERRKEKSRDAARSRRSKESEVFYELAHQLPLPHNVSSHLDKAS   59
Mus            MEG-AGGENEKK-KMSSERRKEKSRDAARSRRSKESEVFYELAHQLPLPHNVSSHLDKAS   58
Rattus         MEG-AGGENEKKNRMSSERRKEKSRDAARSRRSKESEVFYELAHQLPLPHNVSSHLDKAS   59
Microtus       MEG-AGGENEKK-KMSSERRKEKSRDAARSRRSKESEVFYELAHQLPLPHNVSSHLDKAS   58
Human          MEG-AGGANDKK-KISSERRKEKSRDAARSRRSKESEVFYELAHQLPLPHNVSSHLDKAS   58
Pongo          MEG-AGGANDKKNRISSERRKEKSRDAARSRRSKESEVFYELAHQLPLPHNVSSHLDKAS   59
Macaca         MEG-AGGANDKK-KISSERRKEKSRDAARSRRSKESEVFYELAHQLPLPHNVSSHLDKAS   58
Spermaphilus   MEG-AGGTNDKK-KISSERRKEKSRDAARSRRSKESEVFYELAHQLPLPHNVSSHLDKAS   58
Bos            MEG-AGGANDKK-KISSERRKEKSRDAARSRRSKESEVFYELAHQLPLPHXVSSHLDKAS   58
Pantholops     MEG-AGGANDKK-KISSERRKEKSRDAARSRRSKESEVFYELAHQLPLPHNVSSHLDKAS   58
Canis          MEG-AGGANDKK-KISSERRKEKSRDAARSRRSKESEVFYELAHQLPLPHNVSSHLDKAS   58
Oryctolagus    MEG-AGGANDKK-KISSERRKEKSRDAARSRRSKESEVFYELAHQLPLPHNVSSHLDKAS   58
Gallus         MDS-PGGVTDKK-RISSERRKEKSRDAARCRRSKESEVFYELAHQLPLPHTVSAHLDKAS   58
Danio          MDT--GVVTEKK-RVSSERRKGKSRDAARSRRGKESEVFYELAHQLPLPHNVTSHLDKAS   57
Xenopus        MEG-SVVVSEKK-RISSERRKEKSRDAARCRRSNESEVFYELSHELPLPHNVSSHLDKAS   58
               *:  . :  ::*  *******  ***** **.::**************  *::*******

Spalax         VMRLTISYLRVRKLLDAGDLDI--EDEMKAQMNCFYLKALDGFVMVLTDDGDMIYISDNV  116
Eospalax       VMRLTISYLRVRKLLDAGDLDI--EDDMKAQMNCFYLKALDGFVMVLTDDGDMIYISDNV  117
Mus            VMRLTISYLRVRKLLDAGGLDS--EDEMKAQMDCFYLKALDGFVMVLTDDGDMVYISDNV  116
Rattus         VMRLTISYLRVRKLLGAGDLDI--EDEMKAQMNCFYLKALDGFVMVLTDDGDMIYISDNV  117
Microtus       VMRLTISYLRVRKLLDAGDLDI--EDEMKAQMNCFYLKALDGFVMVLTDDGDMIYISDNV  116
Human          VMRLTISYLRVRKLLDAGDLDI--EDDMKAQMNCFYLKALDGFVMVLTDDGDMIYISDNV  116
Pongo          VMRLTISYLRVRKLLDAGDLDI--EDEMKAQMNCFYLKALDGFVMVLTDDGDMIYISDNV  117
Macaca         VMRLTISYLRVRKLLDAGDLDI--EDEMKAQMNCFYLKALDGFVMVLTDDGDMIYISDNV  116
Spermaphilus   VMRLTISYLLVRKLLDAGDLDI--EDEMKAQMNCFYLKALDGFVMVLTDDGDMIYISDNV  116
Bos            VMRLTISYLRVRKLLDAGDLDI--EDEMKAQMNCFYLKALDGFVMVLTDDGDMIYISDNV  116
Pantholops     VMRLTISYLRVRKLLDAGDLDI--EDEMKAQMNCFYLKALDGFVMVLTDDGDMIYISDNV  116
Canis          VMRLTISYLRVRKLLDAGDLDI--EDEMKAQMNCFYLKALDGFVMVLTDDGDMIYISDNV  116
Oryctolagus    VMRLTISYLRVRKLLDAGDLDI--EDEMKAQMNCFYLKALDGFVMVLTDDGDMIYISDNV  116
Gallus         IMRLTISYLRMRKLLDAGELET--EANMEKELNCFYLKALEGFLMVLSEDGDMIYMSENV  116
Danio          IMRLTISYLRMRKLLNSDEKEBEKEENELESQLNGFYLKALEGFLVLTEEGDMIYLSENV  117
Xenopus        IMRLDHQLPAVEKVADAGDLDG--ETELDKQLNCFYLKALEGFVLTEEGDMIYLSENV   116
               :***  .  :.*:  .       *     :: ********:**:: .****:*:::**
```

*Figure 8*

```
Spalax          NKYMGLTQFELTGHSVFDFTHPCDHEEMREMLTHRNGPVKEGKEQNTQRSFFLRMKCTLT  176
Eospalax        NKYMGLTQFELTGHSVFDFTHPCDHEEMREMLTHRNGPIKKGKEQNTQRSFFLRMKCTLT  177
Mus             NKYMGLTQFELTGHSVFDFTHPCDHEEMREMLTHRNGPVRKGKELNTQRSFFLRMKCTLT  176
Rattus          NKYMGLTQFELTGHSVFDFTHPCDHEEMREMLTHRNGPVRKGKEQNTQRSFFLRMKCTLT  177
Microtus        NKYMGLTQFELTGHSVFDFTHPCDHEEMREMLTHRNGPVKKGKEQNTQRSFFLRMKCTLT  176
Human           NKYMGLTQFELTGHSVFDFTHPCDHEEMREMLTHRNGLVKKGKEQNTQRSFFLRMKCTLT  176
Pongo           NKYMGLTQFELTGHSVFDFTHPCDHEEMREMLTHRNGPVKKGKEQNTQRSFFLRMKCTLT  177
Macaca          NKYMGLTQFELTGHSVFDFTHPCGHEEMREMLTHRNGPVKKGKEQNTQRSFFLRMKCTLT  176
Spermaphilus    NKYMGLTQFELTGHSVFDFTHPCDHEEMREMLTHRNGPVKKGKEQNTQRSFFLRMKCTLT  176
Bos             NKYMGLTQFELTGHSVFDFTHPCDHEEMREMLTHRNGLVKKGKEQNTQRSFFLRMKCTLT  176
Pantholops      NKYMGLTQFELTGHSVFDFTHPCDHEEMREMLTHRNGLVKKGKEQNTQRSFFLRMKCTLT  176
Canis           NKYMGLTQFELTGHSVFDFTHPCDHEEMREMLTHRNGLVKKGKEQNTQRSFFLRMKCTLT  176
Oryctolagus     NKYMGLTQFELTGHSVFDFTHPCDHEEMREMLTHRNGPVKKGKEQNTQRSFFLRMKCTLT  176
Gallus          NKCMGLTQFDLTGHSVFDFTHPCDHEELREMLTHRNGPVKKGKEQNTERSFFLRMKCTLT  176
Danio           SKSMGLTQFDLTGHSIFEFSHPCDHEELREMLVHRTG-SKKTKEQNTERSFFLRMKCTLT  176
Xenopus         NKCMGLTQFELTGHSVFDFTHPCDHEELREMLTFRNGPAKKRKRTNHREKFLPSYEMYIN  176
                .*.******.:.:***:*.****.****.:.**  *  .:   .*  *. ..  :  ::

Spalax          S--RGRTMNIKSATWKVLHCTGRIHVYDTNSNQPQCGYKKPPMTCLVLICEPIPHPSNIE  234
Eospalax        S--RGRTMNIKSATWKVLHCTGHIHVYDTNSNQPQCGYKKPPMTCLVLICEPIPHPSNIE  235
Mus             S--RGRTMNIKSATWKVLHCTGHIHVYDTNSNQPQCGYKKPPMTCLVLICEPIPHPSNIE  234
Rattus          S--RGRTMNIKSATWKVLHCTGHIHVYDTSSNQPQCGYKKPPMTCLVLICEPIPHPSNIE  235
Microtus        S--RGRTMNIKSATWKVLHCTGHIHVYDTNSNQSQCGYKKPPMTCLVLICEPIPHPSNIE  234
Human           S--RGRTMNIKSATWKVLHCTGHIHVYDTNSNQPQCGYKKPPMTCLVLICEPIPHPSNIE  234
Pongo           S--RGRTMNIKSATWKVLHCTGHIHVYDTNSNQPQCGYKKPPMTCLVLICEPIPHPSNIE  235
Macaca          S--RGRTMNIKSATWKVLHCTGHIHVYDTNSNQPQCGYKKPPMTCLVLICEPIPHPSNIE  234
Spermaphilus    S--RGRTMNIKSATWKVLHCTGHIHVYDTNSNQSQCGYKKPPMTCLVLICEPIPHPSNIE  235
Bos             S--RGRTMNIKSATWKVLHCTGHIHVYDTNSNQSQCGYKKPPMTCLVLICEPIPHPSNIE  234
Pantholops      S--RGRTMNIKSATWKVLHCTGHIHVYDTNSNQSQCGYKKPPMTCLVLICEPIPHPSNIE  234
Canis           S--RGRTMNIKSATWKVLHCTGHIHVYDTNSNQSQCGYKKPPMTCLVLICEPIPHPSNIE  234
Oryctolagus     S--RGRTMNIKSATWKVLHCTGHIHVYDTNSNQSQCGYKKPPMTCLVLICEPIPHPSNIE  234
Gallus          S--RGRTMNIKSATWKVLHCTGHIRVYDTCNNQTHCGYKKPPMTCLVLICEPIPHPSNIE  234
Danio           S--RGRTVNIKSATWKVLHCAGHVRVHEGSEASEDSGFKEPPVTYLVLICEPIPHPSNIE  234
Xenopus         QSWKNREYKVSHMEGPSLYRT-HACIYDNANNQNHCGYKKPPMTCMVVICEPIPHPSNIE  235
                .  * :   :: . ::  :*    **   *.: * *:*:*****
```

*Figure 8 (cont'd)*

| Species | Sequence | Pos |
|---|---|---|
| Spalax | IPLDSKTFLSRHSLDMKFSYCDERITELMGYEPEELLGRSIYEYYHALDSDHLTKTHHDM | 294 |
| Eospalax | IPLDSKTFLSRHSLDMKFSYCDERITELMGYEPEELLGRSIYEYYHALDSDHLTKTHHDM | 295 |
| Mus | IPLDSKTFLSRHSLDMKFSYCDERITELMGYEPEELLGRSIYEYYHALDSDHLTKTHHDM | 294 |
| Rattus | IPLDSKTFLSRHSLDMKFSYCDERITELMGYEPEELLGRSIYEYYHALDSDHLTKTHHDM | 295 |
| Microtus | IPLDSKTFLSRHSLDMKFSYCDERITELMGYEPEELLGRSIYEYYHALDSDHLTKTHHDM | 294 |
| Human | IPLDSKTFLSRHSLDMKFSYCDERITELMGYEPEELLGRSIYEYYHALDSDHLTKTHHDM | 294 |
| Pongo | IPLDSKTFLSRHSLDMKFSYCDERITELMGYEPEELLGRSIYEYYHALDSDHLTKTHHDM | 295 |
| Macaca | IPLDSKTFLSRHSLDMKFSYCDERITELMGYEPEELLGRSIYEYYHALDSDHLTKTHHGM | 294 |
| Spermaphilus | IPLDSKTFLSRHSLDMKFSYCDERITELMGYEPEELLGRSIYEYYHALDSDHLTKTHHDM | 294 |
| Bos | IPLDSKTFLSRHSLDMKFSYCDERITELMGYEPEELLGRSIYEYYHALDSDHLTKTHHDM | 294 |
| Pantholops | IPLDSKTFLSRHSLDMKFSYCDERITELMGYEPEELLGRSIYEYYHALDSDHLTKTHHDM | 294 |
| Canis | IPLDSKTFLSRHSLDMKFSYCDERITELMGYEPEELLGRSIYEYYHALDSDHLTKTHHDM | 294 |
| Oryctolagus | IPLDSKTFLSRHSLDMKFSYCDERITELMGYEPEELLGRSIYEYYHALDSDHLTKTHHDM | 294 |
| Gallus | VPLDSKTFLSRHSLDMKFSYCDERITELMGYEPEELLGRSIYEYYHALDSDHLTKTHHDM | 294 |
| Danio | VPLDSKTFLSRHTLDMKFSYCDERITELMGYEPDDLLNRSVYEYYHALDSDHLTKTHHNL | 294 |
| Xenopus | FPLDSKTFLSRHSLDMKFSYCDERVTELVGYEPDELLGRSVYEYYHALDSDHLTKPNYM | 295 |
|  | .*:******.**:.*.*:* *:*.*********** :::: |  |

| Species | Sequence | Pos |
|---|---|---|
| Spalax | FTKGQVTTGQYRMLAKRGGYVWVETQATVIYNTRNSQPQCIVCVNYVVSGIIQHDLIFSL | 354 |
| Eospalax | FTKGQVTTGQYRMLAKRGGYVWVETQATVIYNTRNSQPQCIVCVNYVVSGIIQHDLIFSL | 355 |
| Mus | FTKGQVTTGQYRMLAKRGGYVWVETQATVIYNTKNSQPQCIVCVNYVVSGIIQHDLIFSL | 354 |
| Rattus | FTKGQVTTGQYRMLAKRGGYVWVETQATVIYNTKNSQPQCIVCVNYVVSGIIQHDLIFSL | 355 |
| Microtus | FTKGQVTTGQYRMLAKRGGYVWIETQATVIYNTKNSQPQCIVCVNYVVSGIIQHDLIFSL | 354 |
| Human | FTKGQVTTGQYRMLAKRGGYVWVETQATVIYNTKNSQPQCIVCVNYVVSGIIQHDLIFSL | 354 |
| Pongo | FTKGQVTTGQYRMLAKRGGYVWVETQATVIYNTKNSQPQCIVCVNYVVSGIIQHDLIFSL | 355 |
| Macaca | FTKGQVTTGQYRMLAKRGGYVWVETQATVIYNTKNSQPQCIVCVNYVVSGIIQHDLIFSL | 354 |
| Spermaphilus | FTKGQVTTGQYRMLAKRGGYVWVETQATVIYNTKNSQPQCIVCVNYVVSGIIQHGLIFSL | 354 |
| Bos | FTKGQVTTGQYRMLAKRGGYVWIETQATVIYNTKNSQPQCIVCVNYVVSGIIQHDLIFSL | 354 |
| Pantholops | FTKGQVTTGQYRMLAKRGGYVWIETQATVIYNTKNSQPQCIVCVNYVVSGIIQHDLIFSL | 354 |
| Canis | FTKGQVTTGQYRMLAKRGGYVWVETQATVIYNTKNSQPQCIVCVNYVVSGIIQHDLIFSL | 354 |
| Oryctolagus | FTKGQVTTGQYRMLAKQGGYVWVETQATVIYNTKNSQPQCIVCVNYVLSGIVQKDLIFSL | 354 |
| Gallus | FAKGQATTGQYRMLAKKGGFVWVETQATVIYNPKNSQPQCIVCVNYVLSGIVEGDVVLSL | 354 |
| Danio | FTKGQVTTGQYRMLAKKGGYVWVETQATVIYNSKRNSQPQCIVCVNYVLSEVVEKDLILSL | 355 |
|  | *:*:.******::.**********::******:::: ..*:* |  |

*Figure 8 (cont'd)*

| Species | Sequence | |
|---|---|---|
| Spalax | QQTECVLKPVE----------SSDMKMTQLFTKV----ESEDTSCLFDKLKKEPDALTMLAP | 402 |
| Eospalax | QQTECVLKPVE----------SSDMKMTQLFTKV----ESEDTSCLFDKLKKEPDALTLLAP | 403 |
| Mus | QQTESVLKPVE----------SSDMKMTQLFTKV----ESEDTSCLFDKLKKEPDALTLLAP | 402 |
| Rattus | QQTESVLKPVE----------SSDMKMTQLFTKV----ESEDTSCLFDKLKKEPDALTLLAP | 403 |
| Microtus | QQTECVLKPVE----------SSDMKMTQLFTKV----ESEDTSCLFDKLKKEPDALTLLAP | 402 |
| Human | QQTECVLKPVE----------SSDMKMTQLFTKV----ESEDTSSLFDKLKKEPDALTLLAP | 402 |
| Pongo | QQTECVLKPVE----------SSDMKMTQLFTKV----ESEDTSSLFDKLKKEPDALTLLAP | 403 |
| Macaca | QQTECVLKPVE----------SSDMKMTQLFTKV----ESEDTSSLFDKLKKEPDALTLLAP | 402 |
| Spermaphilus | QQTECVLKPVE----------SSDMKMTQLFTKV----ESEDTSSLFDKLKKEPDALTLLAP | 402 |
| Bos | QQTECVLKPVE----------SSDMKMTQLFTKV----ESEDTSSLFDKLKKEPDALTLLAP | 402 |
| Pantholops | QQTECVLKPVE----------SSDMKMTQLFTKV----ESEDTSSLFDKLKKEPDALTLLAP | 402 |
| Canis | QQTECVLKPVE----------SSDMKMTQLFTKV----ESEDTSSLFDKLKKEPDALTLLAP | 402 |
| Oryctolagus | QQTECVLKPVE----------SSDMKMTQLFTKV----ESADTSSLFDKLKKEPDALTLLAP | 402 |
| Gallus | GQTECMLKPVE----------SPEMKMTKIFSKD----DWDDTNSLFEKLKQEPDALTVLAP | 402 |
| Danio | QQTVTEPKAVEKESEETEEKTSELDILKLFKPESLNCSLESSTLYNKLKEEPEALTVLAP | 414 |
| Xenopus | GQTASVLIPVE----------SQEIKMPEIFTELN--EENNSECLFDKLKQEPESLTVLAP | 404 |
|  |  .:   : ::...: ::*.  *::.**:*:**:*. | |
| Spalax | AAGDTIISLDFGSDDTETEDQQLEDVPLYNDVMFPSSDDKLTSINLAMSPLPAPETKPL | 462 |
| Eospalax | AAGDTIISLDFGSDDTETEDQQLEDVPLYNDVMFPSSDDKLTSINLAMSPLPASETKPL | 463 |
| Mus | AAGDTIISLDFGSDDTETEDQQLEDVPLYNDVMFPSSNEKLN--INLAMSPLPSSETKPL | 461 |
| Rattus | AAGDTIISLDFGSDDTETEDQQLEDVPLYNDVMFPSSNEKLN--INLAMSPLPASETKPL | 462 |
| Microtus | AAGDTIISLDFGSDDTETEDQQLEEVPLYNDVMFPSSNEKLTNINLALSPLPASETKPL | 462 |
| Human | AAGDTIISLDFGSNDTETDDQQLEEVPLYNDVMLPSPNEKLQNINLAMSPLPTAETKPL | 462 |
| Pongo | AAGDTIISLDFGSNDTETDDQQLEEVPLYNDVMLPSPNEKLQNINLAMSPLPTAETKPL | 463 |
| Macaca | AAGDTIISLDFGSNDTETDDQQLEEVPLYNDVMLPSSNEKLQNINLAMSPLPTSETKPL | 462 |
| Spermaphilus | AAGDTIISLDFGSNDTETDDQQLEEVPLYNDVMFPSSSEKLQNINLAMSPLPASETKPL | 462 |
| Bos | AAGDTIISLDFGSNDTETDDQQLEEVPLYNDVMLPSSNEKLQNINLAMSPLPASETKPL | 462 |
| Pantholops | AAGDTIISLDFGSNDTETDDQQLEEVPLYNDVMLPSSNEKLQNINLAMSPLPASETKPL | 462 |
| Canis | AAGDTIISLDFGSNDAETDDQQLEEVPLYNDVMLPSSNEKLQNINLAMSPLPASETKPL | 462 |
| Oryctolagus | AAGDTIISLDFGSNDTETDDQQLEEVPLYNDVMFPSSNEKLQNINLALSPLPASETKPL | 462 |
| Gallus | AAGDTIISLDFGSNDTETDDQQLEEVPLYNDVMLPSSNEKLQDINLAMSPLPASESPKPL | 462 |
| Danio | AAGDAIISLDFNNSD--ESDEQQCDEVPLYNDVMLPSSSEKLQNINIAMSPLPASETTKPL | 460 |
| Xenopus | DAGDEIIPLDFSSGD---SDKPYEDVPLYNDVMLHSTSNKLES--TPITPLPAPEMPKPL | 459 |
|  | *. . *** .    ..*:*:*:  ..:::* | |

*Figure 8 (cont'd)*

```
Spalax         RSNADPALNQEVALKLEPNAESLELSFTMPQIQDQPASPSDGSTRQSSPE------------  512
Eospalax       RSNADPALNQEVALKLEPNAESLELSFTMPQIQDQPASPSDGSTRQSSPE------------  513
Mus            RSSADPALNQEVALKLESSPESLGLSFTMPQIQDQPASPSDGSTRQSSPERLLQENVNTP-  521
Rattus         RSSADPALNQEVALKLESSPESLGLSFTMPQIQDQPASPSDGSTRQSSPE------------  512
Microtus       RSSADPALNQEVALKLEPSPESLELSFTMPQIQDQPASPSDGSTRQSSPE------------  512
Human          RSSADPALNQEVALKLEPNPESLELSFTMPQIQDQTPSPSDGSTRQSSPE------------  512
Pongo          RSSADPALNQEVALKLEPNPESLELSFTMPQIQDQPPSPSDGSTRQSSPE------------  513
Macaca         RSSADPALNQEVALKLEPNPESLELSFTMPQIQDQPPSPSDGSTRQSSPE------------  512
Spermaphilus   RSSADPALNQEVALKLEPNPESLELSFTMPQIQDQPASPSDGSTRQSSPE------------  512
Bos            RSSADPALNQEVALKLEPNPESLELSFTMPQIQDQPASPSDGSTRQSSPE------------  512
Pantholops     RSSADPALNQEVALKLEPNPESLELSFTMPQIQDQPASPSDGSTRQSSPE------------  512
Canis          RSSADPALNQEVALKLEPNPESLELSFTMPQIQDQPASPSDGSTRQSSPE------------  512
Oryctolagus    RSSADPALNQEVALKLEPNPESLELSFTMPQIQDQPASPSDGSTRQSSPE------------  512
Gallus         RSNADPALNREVVSKLEPNTETLELSFTMPQVQEQPTSPSDASTSQSSPE------------  510
Danio          SSHATTAKSTLPCRRRHPGP----------------------------------------  486
Xenopus        RSNVDPALNREVVIKMESNPRTTCASIHHSTAIQARQPFRYQFQSEPSTEP----------  510
               *   :   . *     :  .  .

Spalax         ----PNSPSEYCFDVDSDMVFKLELVEKLFAEDTEAKNPFSTQDTDLDLEMLAPYIPM    568
Eospalax       ----PNSPSEYCFDVDSDMVFKLELVEKLFAEDTEAKNPFSTQDTDLDLEMLAPYIPM    569
Mus            NFSQPNSPSEYCFDVDSDMVNVFKLELVEKLFAEDTEAKNPFSTQDTDLDLEMLAPYIPM  581
Rattus         ----PNSPSEYCFDVDSDMVNVFKLELVEKLFAEDTEAKNPFSAQDTDLDLEMLAPYIPM  568
Microtus       ----PNSPSEYCFDVDSDMVNVFKLELVEKLFAEDTEAKNPFSTQDTDLDLEMLAPYIPM  568
Human          ----PNSPSEYCFYVDSDMVNVFKLELVEKLFAEDTEAKNPFSTQDTDLDLEMLAPYIPM  568
Pongo          ----PNSPSEYCFYVDSDMVNEFKLELVEKLFAEDTEAKNPFSTQDTDLDLEMLAPYIPM  569
Macaca         ----PNSPSEYCFYVDSDMVNEFKLELVEKLFAEDTEAKNPFSTQDTDLDLEMLAPYIPM  568
Spermaphilus   ----PNSPSEYCFDVDSDMVNEFKLELVEKLFAEDTEAKNPFSTQDTDLDLEMLAPYIPM  568
Bos            ----PNSPSEYCFDVDSDMVNEFKLELVEKLFAEDTEAKNPFSTQDTDLDLEMLAPYIPM  568
Pantholops     ----PNSPSEYCFDVDSDMVNEFKLELVEKLFAEDTEAKNPFSTQDTDLDLEMLAPYIPM  568
Canis          ----PNSPSEYCFDVDSDMVNVFKLELVEKLFAEDTEAKNPFSTQDTDLDLEMLAPYIPM  568
Oryctolagus    ----PTSPSEYCFDVDSDMVNVFKLELVEKLFAEDTEAKNPFSTQDTDLDLEMLAPYIPM  568
Gallus         ----PSSPNDYCFDVDNDMANEFKLELVEKLFAIDTEAKNPFSTQETDLDLEMLAPYIPM  566
Danio          ----------------------------------------LHPYT--              491
Xenopus        ----NTPEYCFDVDSEMASEFKLDLVEKLFAIDTEAKAPFYYPGNDLDLEMLAPYIPM    564
                                                          *  **
```

```
Spalax         KSHPRSPNLLSVSLSQRNTVPEEELNPKIIAL-QNAQRKRKMEHDGSLFQAAGIGTLLQQ  738
Eospalax       KSHPRSPNVLSVTLSQRNTVPEEELNPKIIAL-QNAQRKRKMEHDGSLFQAAGIGTLLQQ  733
Mus            KAHPRSLK-LSATLNQRNTVPEEELNPKTIAS-QNAQRKRKMEHDGSLFQAAGIGTLLQQ  750
Rattus         KAHPRSLN-LSVTLNQRNTVPEEELNPKTIAL-QNAQRKRKMEHDGSLFQAAGIGTLLQQ  737
Microtus       KAHPRSPN-MSVTLSQRNTVTEEDLNPKIIAL-QNAQRKRKMEHDGSLFQASGIGTLLQQ  742
Human          KSHPRSPNVLSVALSQRTTVPEEELNPKILAL-QNAQRKRKMEHDGSLFQAVGIGTLLQQ  740
Pongo          KSHPRSPNVLSVALSQRTTVPEEELNPKILAL-QNAQRKRKMEHDGSLFQAVGIGTLLQQ  741
Macaca         KSHPRSPNVLSVTLSQRTTVPEEELNPKILAL-QNAQRKRKMEHDGSLFQAVGIGTLLQQ  740
Spermaphilus   KSHPRSPNVVSVTLSQRTTVPEEELNPKILAL-QNAQKAKMEQDGSLFQAVGIGTLLQQ  735
Bos            KSHPRSPNVLSVALSQRTTAPEEELNPKILAL-QNAQRKRKIEHDGSLFQAVGIGTLLQQ  737
Pantholops     KSHPRSPNVLSVALSQRTTAPEEELNPKILAL-QNAQRKRKIEHDGSLFQAVGIGTLLQQ  737
Canis          KSHPRSPNVLSVTLSQRTTIPEEELNPKILAL-QNAQRKRKIEHDGSLFQAVGIGTLLQQ  737
Oryctolagus    KSHPRSPNVLAVTLSQRTTAPEEELNPKILAL-QNAQRKRKMESDGSLFQAVGIGTLLQQ  733
Gallus         KSCPGAPSLITVTLNKRSTAMDEELNPKMLAL-HNAQRKRKMEHDGSLFQAVGIGSLFQQ  725
Danio          -----------------------------------------------VAVGMPHLFDP  515
Xenopus        KSRPGTPN-LPVPLNKRCTILDEELNPKMICFTQCTAEKRKMESDGPLFQAIGIGTLFQT  719
                                                                    *  * :::

Spalax         PDDRAPATSLSWKRVKGCKSSGQNGMEQKTIILIPSDLACRLLGQSMDGSGLPQLTSYDC  798
Eospalax       PDDRAPATSLSWKRVKGCKSSGQNGMEQKTIILIPSDLACRLLGQSMDGSGLPQLTSYDC  793
Mus            PGDCAPTMSLSWKRVKGFISSEQNGTEQKTIILIPSDLACRLLGQSMDESGLPQLTSYDC  810
Rattus         PGDRAPTMSLSWKRVKGYISSEQDGMEQKTIFLIPSDLACRLLGQSMDESGLPQLTSYDC  797
Microtus       PGDRAPTTSLSWKRVKGCKSNEQNGMEQKTIILIPSDLACRLLGQSMDESGLPQLTSYDC  802
Human          PDDHAATTSLSWKRVKGCKSSEQNGMEQKTIILIPSDLACRLLGQSMDESGLPQLTSYDC  800
Pongo          PDDHAATTSLSWKRVKGCKSSEQNGMEQKTIILIPSDLACRLLGQSMDESGLPQLTSYDC  801
Macaca         PEDHAATTSLSWKRVKGCKSSEQNGMEQKTIILIPSDLACRLLGQSMDESGLPQLTSYDC  800
Spermaphilus   PDDHAATTSLSWKRVKGCKSSEQNGMEQKTIILIPSDLACRLLGQSMDESGLPQLTSYDC  795
Bos            PDDRATTTSLSWKRVKGCKSSEQNGMEQKTIILIPSDLACRLLGQSMDESGLPQLTSYDC  797
Pantholops     PDDRATTTSLSWKRVKGCKSSEQNGMEQKTIILIPSDLACRLLGQSMDESGLPQLTSYDC  797
Canis          PDDRATTTSLSWKRVKGCKSSEQNGMEQKTIILIPSDLACRLLGQSMDESGLPQLTSYDC  797
Oryctolagus    PDDRTTTASLSWKRVKGCKSSEQNGMEQKTIILIPSDLACRLLGQSMDESGLPQLTSYDC  793
Gallus         TGDRGGNASLAWKRVKACKTNGHNGVEQKTIILLSTDIASKLLGQSMDESGLPQLTSYDC  785
Danio          APHRAAVSSTTEKCLQRC------------------------------------------  533
Xenopus        NVDPGPNSSLQWKRVKGSDSERLSSAEQRTILLLSTDMASQLLGQSFDGTVLPQLTGYDC  779
                  *  * ::
```

*Figure 8 (cont'd)*

| | | |
|---|---|---|
| Spalax | EVNAPIQGSRNLLQGEELLRALDQVN | 824 |
| Eospalax | EVNAPIQGSRNLLQGEELLRALDQVN | 819 |
| Mus | EVNAPIQGSRNLLQGEELLRALDQVN | 836 |
| Rattus | EVNAPIQGSRNLLQGEELLRALDQVN | 823 |
| Microtus | EVNAPVQGSRNLLQGEDLLRALDQVN | 828 |
| Human | EVNAPIQGSRNLLQGEELLRALDQVN | 826 |
| Pongo | EVNAPIQGSRNLLQGEELLRALDQVN | 827 |
| Macaca | EVNAPIQGSRNLLQGEELLRALDQVN | 826 |
| Spermaphilus | EVNAPIQGSRNLLQGEELLRALDQVN | 821 |
| Bos | EVNAPIQGSRNLLQGEELLRALDQVN | 823 |
| Pantholops | EVNAPIQGSRNLLQGEELLRALDQVN | 823 |
| Canis | EVNAPIQGSRNLLQGEELLRALDQVN | 823 |
| Oryctolagus | EVNAPIQGSRNLLQGEELLRALDQVN | 819 |
| Gallus | EVNAPIQGNRNLLQGEELLRALDQVN | 811 |
| Danio | -------------------------- | |
| Xenopus | EVNAPVHGTRNLLQGEELLRALDQAN | 805 |

*Figure 8 (cont'd)*

INHIBITION OF HIF-1 ACTIVATION FOR ANTI-TUMOR AND ANTI-INFLAMMATORY RESPONSES

CROSS REFERENCE TO RELATED APPLICATIONS

This application claims the benefit of U.S. Provisional Patent Application Ser. No. 60/787,373, filed Mar. 30, 2006, the disclosure of which is incorporated herein by reference in its entirety.

GOVERNMENT INTEREST

The presently disclosed subject matter was made with U.S. Government support under Grant No. EB001882 from the U.S. National Institute of Bioimaging and Bioengineering, Grant No. CA81512 from the U.S. National Cancer Institute, and Grant No. DAMD17-02-0052 from the U.S. Department of Defense. Thus, the United States Government has certain rights in the presently disclosed subject matter.

TECHNICAL FIELD

The presently disclosed subject matter generally relates to methods and compositions for inhibiting the expression and/or activation of hypoxia-inducible factor 1 (HIF-1) gene products in a hypoxic cell. More particularly, the presently disclosed subject matter provides methods and compositions involved in inhibition of HIF-1 activation through the use of agents that prevent the nitrosylation of HIF-1.

BACKGROUND

In a typical clinical setting, radiation therapy and/or chemotherapy treatments are administered to the majority (>90%) of cancer patients. Therefore, along with surgery, radiation therapy and chemotherapy represent two of the three main modalities employed for cancer treatment. However, the therapeutic outcomes are still far from ideal for many types of tumors. The main problem associated with radiotherapy is the recurrence of tumors and/or the development of metastases at distant locations. For chemotherapy, the problem is the development of resistance. In both cases, new methods and compositions that can sensitize tumors to current treatments are highly desirable. Ideally, these methods and compositions should decrease local recurrences in patients treated with radiotherapy and/or should increase the efficacy of chemotherapeutic agents systemically. In addition, they should not have severe side effects.

What are needed, then, are new strategies and compositions for treating tumors and/or cancers via inhibition of HIF-1 activity and/or the upregulation of HIF-1 activity that results from radiotherapy and/or chemotherapy. The presently disclosed subject matter addresses this and other needs in the art.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

The presently disclosed subject matter provides methods for increasing a sensitivity of a tumor in a subject to a treatment. In some embodiments, the methods comprise administering to the tumor a composition comprising an effective amount of an inhibitor of nitric oxide synthase, a nitric oxide scavenger, an inhibitor of HIF-1 nitrosylation, or a combination thereof, wherein (i) the tumor is resistant to radiation therapy, chemotherapy, or both radiation therapy and chemotherapy; and (ii) the administering increases the sensitivity of the tumor to the radiotherapy, the chemotherapy, or both the radiotherapy and the chemotherapy. In some embodiments, the inhibitor of nitric oxide synthase is selected from the group consisting of L-N(6)-(1-iminoethyl)lysine tetrazole-amide (SC-51); aminoguanidine (AG); guanidinoethyldisulfide; L-NG-nitroarginine methyl ester; mercaptoethylguanidine (MEG); $N^{\omega}$-nitro-L-arginine methyl ester (L-NAME); N-(3-(aminomethyl)benzyl)acetamidine (1400W); $N^G$-monomethyl-L-arginine (L-NMMA); 7-nitroindazole (7-NI). In some embodiments, the nitric oxide scavenger is selected from the group consisting of hydroxocobalamin; 2-(4-carboxyphenyl)-4,4,5,5-tetramethylimidazoline-1-oxyl-3-oxide (carboxy-PTIO); diethyldithiocarbamate; AMD6221 (ruthenium[hydrogen(diethylenetrinitrilo) pentaacetato]chloride); and N-dithiocarboxy-sarcosine (DTCS). In some embodiments, the administering comprises administering a minimally therapeutic dose of an inhibitor of inducible nitric oxide synthase (iNOS). In some embodiments, the composition inhibits nitrosylation of Cys520 of SEQ ID NO: 6.

The presently disclosed subject matter also provides methods for delaying tumor growth in a subject. In some embodiments, the methods comprise (a) administering to the subject a composition comprising an effective amount of an inhibitor of nitric oxide synthase, a nitric oxide scavenger, an inhibitor of HIF-1 nitrosylation, or a combination thereof; and (b) treating a tumor that is resistant to radiation therapy, chemotherapy, or both radiation therapy and chemotherapy, with radiation therapy, chemotherapy, or both radiation therapy and chemotherapy, whereby tumor growth in the subject is delayed. In some embodiments, the composition inhibits nitrosylation of Cys520 of SEQ ID NO: 6. In some embodiments, the treating comprises treating the tumor with a sub-therapeutic dose of ionizing radiation. In some embodiments, the treating comprises administering to the subject a therapeutically effective amount of cyclophosphamide. In some embodiments, the method further comprises promoting tumor regression.

The presently disclosed subject matter also provides methods for inhibiting tumor blood vessel growth in a subject. In some embodiments, the methods comprise (a) administering to the subject a composition comprising an effective amount of an inhibitor of nitric oxide synthase, a nitric oxide scavenger, an inhibitor of HIF-1 nitrosylation, or a combination thereof; and (b) treating a tumor that is resistant to radiation therapy, chemotherapy, or both radiation therapy and chemotherapy, with radiation therapy, chemotherapy, or both radiation therapy and chemotherapy, whereby tumor blood vessel growth is inhibited. In some embodiments, the composition inhibits nitrosylation of Cys520 of SEQ ID NO: 6. In some embodiments, the methods further comprise delaying tumor growth in the subject. In some embodiments, the methods further comprise promoting tumor regression in the subject.

The presently disclosed subject matter also provides methods for inhibiting HIF-1 activity in a cell. In some embodiments, the methods comprise contacting the cell with a composition comprising an effective amount of an inhibitor of nitric oxide synthase, a nitric oxide scavenger, an inhibitor of HIF-1 nitrosylation, or a combination thereof, whereby HIF-1 activity in the cell is inhibited. In some embodiments, the cell is a tumor cell. In some embodiments, the tumor cell is present in a subject. In some embodiments, the subject is a mammal. In some embodiments, the mammal is a human. In some embodiments, the composition inhibits nitrosylation of Cys520 of SEQ ID NO: 6. In some embodiments, the methods further comprise exposing the tumor cell to a treatment selected from the group consisting of radiation therapy, chemotherapy, and combinations thereof.

The presently disclosed subject matter also provides methods for inhibiting an inflammatory response in a cell. In some embodiments, the methods comprise contacting the cell with a composition comprising an effective amount of an inhibitor of nitric oxide synthase, a nitric oxide scavenger, an inhibitor of HIF-1 nitrosylation, or a combination thereof, whereby an inflammatory response in the cell is inhibited. In some embodiments, the cell is present in a subject. In some embodiments, the subject is a mammal. In some embodiments, the mammal is a human. In some embodiments, the agent inhibits nitrosylation of Cys520 of SEQ ID NO: 6.

In some embodiments of the presently disclosed methods, the composition is provided to the subject in an implantable device. In some embodiments, the subject is a mammal, and in some embodiments the mammal is a human.

The presently disclosed subject matter also provides methods for identifying an inhibitor of nitrosylation of an HIF-1 polypeptide. In some embodiments, the methods comprise (a) providing a cell comprising a nucleic acid a nucleotide sequence comprising any of SEQ ID NOs: 18-21; (b) contacting the cell with a compound comprising a potential inhibitor of nitrosylation of an HIF-1 polypeptide; and (c) assaying nitrosylation of a cysteine residue present in the nucleic acid, whereby an inhibitor of nitrosylation of an HIF-1 polypeptide is identified. In some embodiments, the cell is present in a subject. In some embodiments, the subject is a mammal. In some embodiments, the mammal is a human. In some embodiments, the nucleic acid comprises an expression vector in which the nucleic acid is operably linked to a promoter that is active in the cell. In some embodiments, the expression vector is a transgene and the animal is a transgenic animal that expresses the nucleic acid. In some embodiments, the compound is administered to the transgenic animal via a route that results in the compound contacting the cell. In some embodiments, the methods further comprise comparing a level of nitrosylation of the cysteine residue present in the nucleic acid to a level of nitrosylation of the cysteine residue present in the nucleic acid prior to the contacting step. In some embodiments, the cell is an in vitro cultured cell and the contacting is performed in vitro.

The presently disclosed subject matter also provides expression constructs comprising one or more of SEQ ID NOs: 18-21 operably linked to a promoter.

The presently disclosed subject matter also provides expression constructs comprising one or more of SEQ ID NOs: 18-21 operably linked to a promoter, with the proviso that all cysteine residues present within SEQ ID NOs: 18-21 have been replaced with a non-nitrosylatable amino acid. In some embodiments, the non-nitrosylatable amino acid is serine.

The presently disclosed subject matter also provides host cells comprising the disclosed expression constructs.

The presently disclosed subject matter also provides transgenic, non-human animals comprising the disclosed expression constructs.

The presently disclosed subject matter also provides for the use of inhibitors of nitric oxide synthases to prevent activation of HIF-1 activity in tumors by cancer therapy that include radiation and chemotherapy, the use of nitric oxide scavengers to prevent activation of HIF-1 activity in tumors by cancer therapy that include radiation and chemotherapy, the use of agents that can reduce the production of NO to sensitize tumors to radiotherapy and/or chemotherapy, the use of nitric oxide synthase or nitric oxide scavengers to inhibit inflammatory reaction through the inhibition of HIF-1 activation, the use of agents that can block the nitrosylation of HIF-1α cysteine 520 for the purpose of enhancing cancer therapy, and the use of agents that can block the nitrosylation of HIF-1α cysteine 520 for the purpose of inhibiting/attenuating inflammatory response.

This and other objects are achieved in whole or in part by the presently disclosed subject matter.

An object of the presently disclosed subject matter having been stated above, other objects and advantages of the presently disclosed subject matter will become apparent to those of ordinary skill in the art after a study of the following description and non-limiting Examples.

BRIEF DESCRIPTION OF THE DRAWINGS

The patent or application file contains at least one drawing executed in color. Copies of this patent or patent application publication with color drawing(s) will be provided by the United States Patent and Trademark Office upon request and payment of the necessary fee.

FIG. 1A depicts the domain structure of murine HIF-1α and reporter proteins. The oxygen dependent degradation (ODD) domain is located between amino acids 401 to 613 (top construct) of murine HIF-1α (SEQ ID NO: 3). The ODD-luc reporter coding sequence (middle construct) was obtained by inserting the ODD domain of murine HIF-1α between an upstream cytomegalovirus (CMV) promoter and the downstream gene firefly luciferase coding sequence (luc). The ODD and luc sequences were engineered to be in frame. A Kozak sequence and start codon (ATG) were inserted 5' of the ODD coding sequence. A luciferase coding sequence driven by the CMV promoter (lower construct) was used as a control.

FIG. 1B is a graphical depiction of the expression of ODD-luc in 4T1 cells determined from luc-dependent conversion of luciferin to luminescent oxoluciferin, and measurement of associated light emission. ODD-luc expression/activity was measured in 4T1 cells cultured after activation of ODD-luc by $CoCl_2$ (240 µM for 12 hrs), exposure to a proteasome inhibitor (10 µM MG132 for 12 hrs), hypoxia (0.5% $O_2$ for 24 hrs), or anti-VHL siRNA transfection (VHL-KD). The average luc activities were calculated from triplicate experiments in each case. Significant differences were observed between control and treated cells ($p<0.05$ in all cases, Student's t test).

FIG. 1C depicts Western blot analysis showing down regulation of VHL protein expression after introducing an siRNA-expressing vector encoding an anti-VHL minigene into 4T1 cells as a stable, integrated construct. The sequence of the siRNA was AACATCACATTGCCAGTGTAT (SEQ ID NO: 17). β-actin levels were used as loading controls.

FIG. 1D depicts Western blot analysis of wild type 4T1 cells treated as in FIG. 1B. Lysates of the cells were analyzed for endogenous HIF-1α protein expression using a rabbit anti-mouse HIF-1α polyclonal antiserum. VHL-KD: cells stably transduced with an siRNA gene against VHL. β-actin was used as the loading control.

FIGS. 2A-2C depict in vivo activation of HIF-1α by ionizing radiation in tumors.

FIG. 2A depicts luciferase activity in 4T1 tumors stably transduced with ODD-luc or CMV-luc reporter genes established in nude mice. Size-matched tumors were locally irradiated (6 Gy) at day 0. Luciferase activity in tumors was determined daily though non-invasive imaging. Fourteen animals were used in each group and the error bars indicate the standard error of the mean. The difference between the irradiated group and control was significant ($p<0.05$ from day 3 to day 10 by two-way ANOVA).

FIG. 2B is a bar graph presenting the results of radiation-induced activation of endogenous HIF-1 binding activity to a hypoxia responsive element (HRE) measured by ELISA in tumors irradiated 5 days earlier. In each group, the average results from 4 tumor samples are shown ($p<0.05$, Student's t test). Error bars represent standard deviation.

FIG. 2C is a bar graph presenting the results of a radiation-induced increase in intratumoral VEGF levels as measured by ELISA. In each group, the average results from 4 tumors are shown ($p<0.05$, Student's t test). Error bars represent standard deviation.

FIG. 3A presents the results of assays for luciferase activity in 4T1-ODD-luc or 4T1-luc transduced tumors established in the hind legs of nude mice and irradiated (at day 0) with or without the administration of L-NAME (at day -1). Luciferase levels were then monitored post irradiation. Tumors with the CMV-luc reporter were used as controls. Significant inhibition of ODD-luc expression were observed by the use of L-NAME. Eight animals were used in each group and the error bars indicate standard error of the mean. $p<0.05$ from day 4 (two-way ANOVA). The graph is of the activities of the listed conditions from day 0 to day 10.

FIG. 3B is a bar graph depicting S-nitrosoglutathione-(GSNO) induced activation of ODD-luc cells in vitro. 4T1-ODD-luc cells were exposed to the NO donor GSNO at indicated dosage and monitored for ODD-luc expression. The data were normalized against cells that were not treated with GSNO. The error bars represent standard deviations. Each data point represents the average of triplicate experiments. Dose-dependent induction was observed. $p<0.001$ (Student's t test)

FIG. 3C depicts Western blot analysis of endogenous HIF-1α protein levels after GSNO treatment (1 mM for 8 hours) in 4T1 cells. β-actin levels were used as loading control.

FIG. 3D is a bar graph depicting suppression of NO-mediated HIF-1α activation by a nitric oxide scavenger. 4T1-ODD-luc cells were exposed to GSNO (1 mM) in the presence or absence of a chemical NO scavenger—carboxy-PTIO (0.5 mM). The cells were monitored for luciferase expression 24 hours later. The error bars represent standard deviation and each data point represents the average of triplicate experiments. $p<0.05$ (Student's t test).

FIG. 4A depicts the effect of an iNOS specific inhibitor. Subcutaneous tumors were established in the hind legs of nude mice through the use of 4T1-ODD-luc cells and irradiated with or without the administration of 1400W, an iNOS-specific inhibitor. ODD-luc level were then monitored daily post irradiation. Significant inhibition of radiation-induced HIF-1 activation was observed in the group treated with 1400W ($p<0.001$ from day 4, two-way ANOVA).

FIG. 4B depicts the effect of a homozygous genetic disruption (i.e., knockout) of the iNOS gene on HIF-1α activation in a host animal. Tumors were established from B16F10-ODD-luc cells in syngeneic wild type or iNOS$^{-/-}$ C57BL/6 mice. In some groups, mice received L-NAME one day before tumor irradiation (6 Gy) at day 0. Luciferase activities were determined every other day. Eight animals were used in each group and the error bars represent the standard errors of the mean. In wild type C57BL/6 mice (solid lines), the difference between L-NAME treated and non-treated groups was statistically significant ($p<0.01$ on days 1, 3, and 5, two-way ANOVA test). In iNOS$^{-/-}$ mice (broken lines), the difference between L-NAME treated and non-treated groups was not significant ($p>0.05$ at all time points, two-way ANOVA).

FIG. 5A depicts luciferase expression in tumors established from 4T1-ODD-luc cells in nude mice. In some mice, macrophages were depleted by injection of carrageenan. Selected groups of mice also received L-NAME one day before irradiation (6 Gy). Luciferase expression was determined every other day. Eight mice were included in each group. The error bars represent the standard errors of the mean.

FIG. 5B depicts immunohistochemistry analysis of HIF-1α, iNOS, and macrophages in tumors. Mice with irradiated 4T1 tumors were sacrificed and their tumors excised 5 days after localized 6 Gy or sham irradiation of tumors. Shown in the left panel are representative results from co-staining of CD68 (a marker for macrophages (Mφ) and iNOS. Co-staining of HIF-1α and iNOS is shown on the right panel. In each case, merged pictures are provided. Orange color in both panels represents co-localization.

FIG. 6A presents amino acid subsequence conservation across different species in the region of Cys 533 of murine HIF-1α (GENBANK® Accession No. NP_034561 (SEQ ID NO: 3). The subsequences presented include PNSPSEYC-FYVDSDM (*Homo sapiens;* SEQ ID NO: 18); PNSPSEY-CFDVDSDM (*Mus musculus;* SEQ ID NO: 19); PNSPSEY-CFDVDSDM (*Rattus norvegicus;* SEQ ID NO: 19); PNSPSEYCFDVDSDM (*Spalax judaei;* SEQ ID NO: 19); PNSPSEYCFDVDSDM (*Bos grunniens;* SEQ ID NO: 19); PNSPMEYCFQVDSDI (*Carassius carassius;* SEQ ID NO: 20); and EPNTPEYCFDVDSEM (*Xenopus laevis;* SEQ ID NO: 21). See also FIG. 8.

FIG. 6B is a bar graph depicting the effects of various stimuli (0.5% hypoxia, proteasome inhibitor MG132, and CoCl$_2$) on the activation of wild type ODD-luc and C533S-ODD-luc in 4T1 cells. The experiments were carried out in the similar manner as those described in FIG. 1B. The data shown are the results of triplicate experiments. The error bars represent standard deviations. In all treatment groups, $p>0.05$ between wild type and mutant ODD-luc expression levels (Student's t test).

FIG. 6C is a bar graph depicting luciferase activity in wild type ODD-luc or C533S ODD-luc transduced 4T1 cells treated with GSNO (1 mM). Significant attenuation of luc expression was observed in C533S-ODD-luc transduced cells ($p<0.01$, Student's t test). Each data point is the results of triplicate experiments and the error bars represent standard errors. The unit for light output shown is p/sec/CM²/Sr.

FIG. 6D is a graph depicting luciferase activity in irradiated (6 Gy) tumors established from 4T1 cells transduced with wild type or C533S-ODD-luc. Luciferase expression was monitored every other day. Significant attenuation of luciferase expression was observed in C533S-ODD-luc-transduced 4T1 tumors (p<0.01 from day 5, two-way ANOVA). Each group has five animals and the error bars represent standard errors of the mean.

FIG. 6E depicts the results of Western blot analysis of S-nitrosylation of C533 in the ODD domain. 4T1 cells transduced with wild type ODD or C533S-ODD (both with a myc-tag at the 3' end for Western blot detection) were exposed to GSNO and then lysed. S-nitrosylation of ODD was determined through the biotin switch assay (Jaffrey & Snyder, 2001). A clear nitrosylation signal was observed for wild type ODD after GSNO treatment, but was not observed in C533S ODD with or without GSNO treatment.

FIG. 6F depicts the results of Western blot analysis demonstrating the absence of binding between nitrosylated ODD and VHL. 4T1 tumor ells were transduced with CMV-ODD-mycTag, CMV-C533S-ODD-mycTag, or CMV-HA-VHL. Where indicated, ODD-transfected cells were exposed to 1 mM GSNO for 8 hours. The lysate of ODD-transfected cells was admixed with lysate of cells expressing HA-VHL. Mixed lysates were immunoprecipitated with anti-HA antibody to pull down the VHL protein and any ODD bound thereto. The immunoprecipitate was then immunoblotted with antibody against mycTag to detect ODD bound to VHL. Total tagged ODD (Input ODD) and VHL (Input VHL) were detected by Western blot analysis with antibodies against the mycTag and the HA-tag, respectively.

FIG. 7A is a graph depicting 4T1 tumor growth delay.

FIG. 7B is a graph depicting B16F10 melanoma growth delay.

FIG. 7C is a bar graph depicting CD31⁺ cells (indicative of vasculature) in tumors excised from different groups on day 10. The tumors were excised, sectioned, and probed for the presence of vasculature by use of an antibody against CD31, which stained for endothelial cells. The average vascular length density of tumors was determined from five randomly chosen fields for each treatment type. The error bars represent the standard errors. The differences between the combined treatment group and the individual groups were significant ($p<0.05$, one way ANOVA) in both tumor models.

Figure 8:
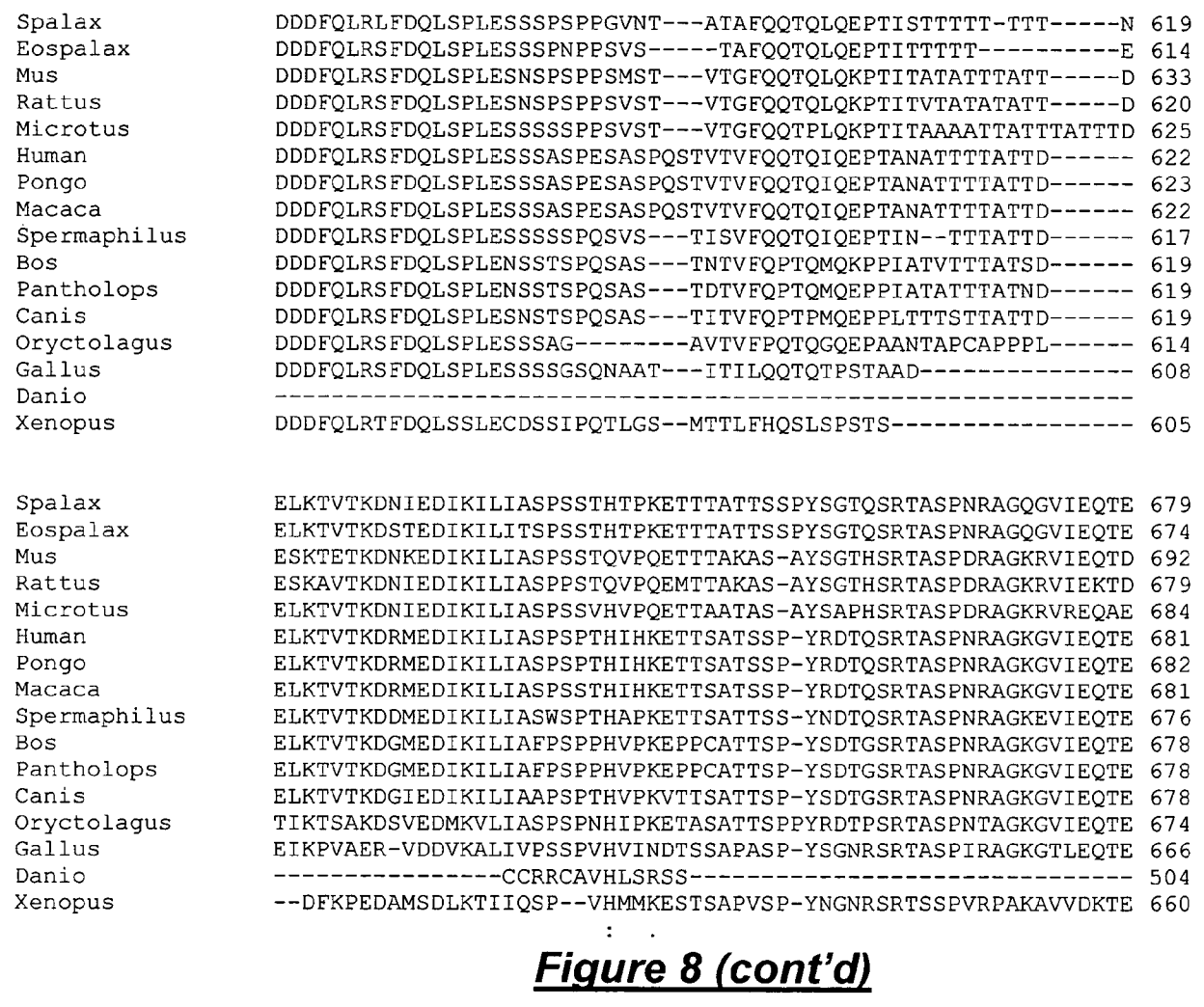

FIG. 8 presents a maximized amino acid sequence alignment of HIF-1α polypeptide sequences from the following organisms: *Spalax judaei* (GENBANK® Accession No. CAG29396; SEQ ID NO: 1); *Eospalax baileyi* (GENBANK® Accession No. ABB17537; SEQ ID NO: 2); *Mus musculus* (GENBANK® Accession No. NP_034561; SEQ ID NO: 3); *Rattus norvegicus* (GENBANK® Accession No. NP_077335; SEQ ID NO: 4); *Microtus oeconomus* (GENBANK® Accession No. AAY27087; SEQ ID NO: 5); *Homo sapiens* (GENBANK® Accession No. NP_001521; SEQ ID NO: 6); *Pongo pygmaeus* (GENBANK® Accession No. CAH93355; SEQ ID NO: 7); *Macaca fascicularis* (GENBANK® Accession No. BAE01417; SEQ ID NO: 8); *Spermophilus tridecemlineatus* (GENBANK® Accession No. AAU14021; SEQ ID NO: 9); *Bos taurus* (GENBANK® Accession No. NP_776764; SEQ ID NO: 10); *Pantholops hodgsonii* (GENBANK® Accession No. AAX89137; SEQ ID NO: 11); *Canis familiaris* (GENBANK® Accession No. XP_852278; SEQ ID NO: 12); *Oryctolagus cuniculus* (GENBANK® Accession No. AAP43517; SEQ ID NO: 13); *Gallus gallus* (GENBANK® Accession No. NP_989628; SEQ ID NO: 14); *Danio rerio* (GENBANK® Accession No. NP_956527; SEQ ID NO: 15); and *Xenopus laevis* (GENBANK® Accession No. CAB96628; SEQ ID NO: 16).

FIG. 9A depicts a time course of ODD-luc change in 4T1 tumors treated with cyclophosphamide.

FIG. 9B depicts images of ODD-luc expression with (bottom 2 panels) or without (top 2 panels) cyclophosphamide exposure.

DETAILED DESCRIPTION

I. General Considerations

Figure 1A:
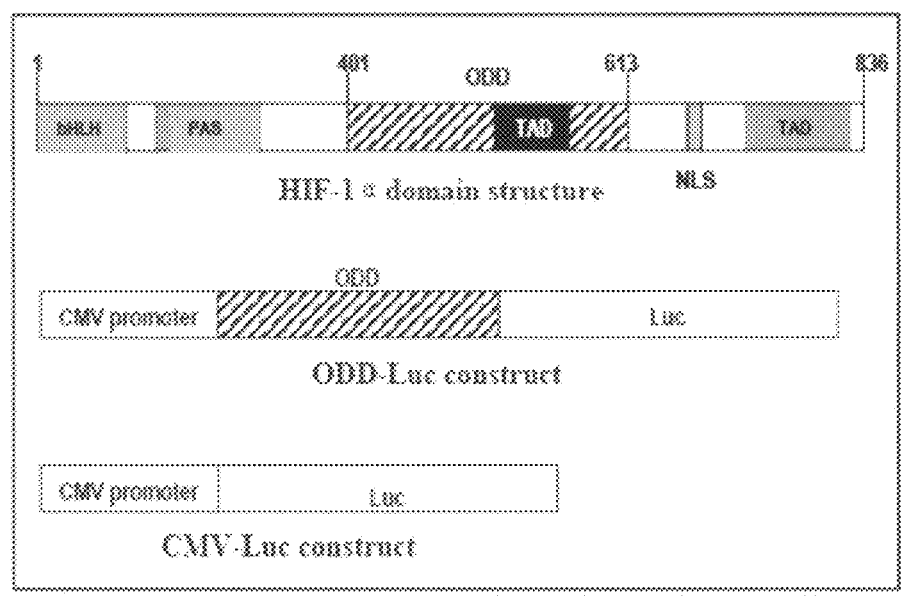
FIGS. 1A-1D depict the results of experiments to establish ODD-luc as a non-invasive reporter for HIF-1α expression.

Radiotherapy and chemotherapy are two of the three main modalities of cancer therapy. However, for the majority of cancer patients, the therapeutic efficacy of chemotherapy or radiotherapy is not ideal. Many tumors are resistant to various chemotherapy and radiotherapy treatments. At the molecular level, the mechanisms involved in such resistance are not completely understood. However, recent studies indicate that the hypoxia-inducible factor 1 (HIF-1) factor might be involved. These studies have shown that radiation and chemotherapy can upregulate the level and activity of HIF-1 protein and this upregulation is related to increased tumor angiogenesis and tumor resistance to therapy. Furthermore, inhibition of HIF-1 activity can significantly increase the sensitivity of tumor cells to radiotherapy and chemotherapy.

Recent progress in the understanding of tumor physiology and the tumor microenvironment has yielded new targets that can be used to develop novel therapeutic agents. One such target is the hypoxia-inducible factor 1 (HIF-1). HIF-1 is a master transcriptional regulator that plays important roles in development, physiology, and many pathological processes (Semenza et al., 2000; Semenza, 2002; Semenza, 2003; Melillo, 2004). Originally identified as a transcription factor activated under conditions of abnormally low oxygen (Wang & Semenza, 1993a; Wang & Semenza, 1993b), HIF-1's potential roles in cancer biology are a topic of current interest. More than 60 genes have been identified as direct targets of HIF-1 activity (Semenza, 2003) including, but not limited to genes involved in angiogenesis, metabolic adaptation, apoptosis induction/resistance, and invasion/metastasis.

HIF-1 is a heterodimeric protein that consists of the constitutively expressed HIF-1β subunit (also called aryl hydrocarbon receptor nuclear translocator; ARNT) and the highly regulated HIF-1α subunit (Wang & Semenza, 1995). The overall activity of HIF-1 is determined by intracellular HIF-1α level. In the past decade, certain insights related to HIF-1α regulation have been realized. One significant advance has been the discovery of HIF-1α regulation by oxygen tension, which is mainly mediated by the ubiquitin-proteasome pathway. Under normoxic conditions, human HIF-1α is hydroxylated by one or more prolyl hydroxylases (PHDs) at proline residues 402 and 564 in the oxygen dependent domain (ODD; Ivan et al., 2001; Jaakkola et al., 2001). This hydroxylation renders HIF-1α susceptible to binding and ubiquitylation by E3 ubiquitin protein ligases, which contain the von Hippel-Lindau tumor suppressor protein (VHL; Pause et al., 1999; Maxwell et al., 1999; Maxwell et al., 2001). Ubiquitylated HIF-1α is then rapidly degraded by the proteasome. Under hypoxic conditions, the enzymatic activities of PHDs are significantly reduced due to the oxygen-dependent nature of PHDs. As a result, HIF-1α accumulates.

In addition to hydroxylation of the proline residues in the ODD domain by PHDs, hydroxylation of the asparagine at residue 803 in human HIF-1α, which is located in the trans-activation domain, by a polypeptide termed factor inhibiting HIF-1 protein (FIH-1) has been found to regulate the activity of HIF-1α by preventing its interaction with two co-activators—p300 and CBP (Lando et al., 2002a; Lando et al., 2002b). Acetylation of a lysine residue (Lys 532 in human HIF-1α) has also been shown to regulate HIF-1 by enhancing the binding of HIF-1α to VHL and its subsequent degradation (Jeong et al., 2002). The ARD1 acetyl transferase has been shown to be responsible for this acetylation.

Still another recently identified mechanism of HIF-1 regulation is fumarate-dependent. Intracellular fumarate is regulated by fumarate hydratase, an enzyme in the tricarboxylic acid (TCA) cycle. Mutations in this gene, which occur in hereditary leiomyomatosis, were shown to cause increased levels of intracellular fumarate. The increased fumarate can act as a competitive inhibitor of prolyl hydroxylase, causing increased level of HIF-1α to accumulate (Isaacs et al., 2005). A similar function has been identified for succinate dehydrogenase (SDH), which is another member of the TCA cycle. Mutations of SDH, a candidate tumor suppressor for renal cell carcinoma, leads to increased succinate level, which has been shown to inhibit PHD activity and to lead to increased HIF-1α levels (Selak et al., 2005).

In solid tumors, HIF-1α activity is regulated via several mechanisms. Hypoxia is a common feature of all solid tumor microenvironments by virtue of the rapid proliferation of tumor cells and the generally poor functionality of newly formed tumor vasculature. Therefore, in the majority of solid tumors, hypoxia plays an important role in upregulating HIF-1α activity (Harris, 2002). In fact, hypoxia-induced HIF-1 activation and subsequent VEGF expression has been postulated to be a major driving force in tumor angiogenesis in solid tumors (Maltepe et al., 1997; Harris, 2002). As a result, a significant effort is now being devoted to the development of HIF-1 inhibitors as anti-cancer drugs (Giaccia et al., 2003; Sutphin et al., 2004).

In addition to hypoxia, many hypoxia-independent pathways of HIF-1 regulation have been identified. These are mainly genetic/epigenetic alterations that can upregulate the level and/or activity of the HIF-1α polypeptide. Loss of VHL (Maxwell et al., 1999; Ohh et al., 2000) and/or p53 gene function (Ravi et al., 2000; Chen et al., 2003; Sanchez-Puig et al., 2005), which decreases the ubiquitylation and subsequent degradation of HIF-1α protein, can significantly upregulate HIF-1 activity. In addition, mutations in the PTEN tumor suppressor gene (Zundel et al., 2000; Zhong et al., 2000), which increase activity of the PI3K-AKT-mTOR signaling pathway (Laughner et al., 2001; Chan et al., 2002); ERBB2 gain of function mutations (Laughner et al., 2001); increased EGFR (Zhong et al., 2000), MEK-ERK (Fukuda et al., 2002), and/or IGF-1R signaling (Fukuda et al., 2003); and SRC gain of function mutations (Jiang et al., 1997) can all cause increased synthesis of the HIF-1α protein and overall HIF-1 activation.

In addition to tumor microenvironmental conditions and genetic/epigenetic changes in host tumor cells, it has recently been shown that HIF-1 activity can also be modified by exposure to radiotherapy (Moeller et al., 2004; Moeller et al., 2005). Exposure to ionizing radiation appears to activate HIF-1 via a hypoxia-independent mechanism. This activation appears to be mediated by a post-transcriptional mechanism that involves the release of pre-stored HIF-1α-encoding mRNAs in "stress granules" located in the cytoplasm (Moeller et al., 2004). The triggering signals were identified to be free radical species induced by exposure to ionizing radiation.

This important discovery indicates that tumors respond to radiotherapy by activating HIF-1, which mediates the expression of VEGF and other factors that protect tumor vasculature against cytotoxic therapy, thereby increasing overall tumor cell survival. Consistent with this hypothesis are data indicating that combining radiotherapy with HIF-1 inhibitors appears to synergize their anti-tumor effects (Moeller et al., 2004).

Accordingly, disclosed herein is the identification of nitric oxide as a major regulator of HIF-1α activity during cancer treatment. Thus, NO inhibitors can be employed as sensitizers of cancer radiation and chemotherapy.

Also disclosed herein is the discovery that an important cysteine (Cys 520) residue in the human HIF-1α protein is responsible NO-mediated activation of HIF-1α during cancer therapy. This residue serves as the site for nitrosylation and subsequent activation of the HIF-1α during cancer therapy. The absence of this residue abolishes the induction of HIF-1α. Therefore, Cys 520 and corresponding residues in HIF-1α polypeptides from other species are targets for drug development.

Also disclosed herein is the discovery that compositions that can inhibit the production of nitric oxide can significantly increase therapeutic efficacy of radiotherapy through the inhibition of radiation-induced HIF-1α upregulation. Therefore, inhibitors of nitric oxide production can act as sensitizers of radiation and cancer treatment.

Also disclosed herein is the administration of agents that can inhibit the production of NO and subsequent nitrosylation and stabilization of the HIF-1α protein in tumors before, during, or after radiation therapy or cytotoxic chemotherapy. One rationale is that these agents would be expected to decrease the level of NO in the tumor microenvironment and cause a concomitant reduction of the level of HIF-1α that is induced by radiation or chemotherapy. Because HIF-1α has been shown to be a key angiogenesis regulator and survival factor for tumors during cancer therapy, the lower level of HIF-1α should allow for a better therapeutic outcome.

In addition, agents that can inhibit the nitrosylation and activation of HIF-1α either directly or indirectly can also serve as inhibitors of anti-inflammatory agents. To that end, disclosed herein is the discovery that treatment of macrophages with inflammation-causing agents can result in the stabilization and activation of HIF-1α. As HIF-1α has been shown to be important in mediating inflammatory response, agents that inhibit the nitrosylation and stabilization of HIF-1α can also be used as anti-inflammatory agents.

II. Definitions

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in this application, including the claims. Thus, for example, reference to "a tumor cell" includes a plurality of such tumor cells, and so forth.

As used herein, the term "about," when referring to a value or to an amount of mass, weight, time, volume, concentration, or percentage is meant to encompass variations of in some embodiments, ±20%, in some embodiments ±10%, in some embodiments ±5%, in some embodiments ±1%, and in some embodiments ±0.1% from the specified amount, as such variations are appropriate to perform the disclosed methods.

As used herein, "significance" or "significant" relates to a statistical analysis of the probability that there is a non-random association between two or more entities. To determine whether or not a relationship is "significant" or has "significance", statistical manipulations of the data can be performed to calculate a probability, expressed as a "p value". Those p values that fall below a user-defined cutoff point are regarded as significant. In some embodiments, a p value less than or equal to 0.05, in some embodiments less than 0.01, in some embodiments less than 0.005, and in some embodiments less than 0.001, are regarded as significant. Accordingly, a p value greater than or equal to 0.05 is considered not significant.

As used herein, the term "subject" refers to any organism for which application of the presently disclosed subject matter would be desirable. The subject treated in the presently disclosed subject matter in its many embodiments is desirably a human subject, although it is to be understood that the principles of the presently disclosed subject matter indicate that the presently disclosed subject matter is effective with respect to all vertebrate species, including mammals, which are intended to be included in the term "subject". Moreover, a mammal is understood to include any mammalian species in which treatment of a tumor and/or a cancer is desirable, particularly agricultural and domestic mammalian species.

More particularly provided is the treatment of mammals such as humans, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economic importance to humans. Thus, contemplated is the treatment of livestock, including, but not limited to, domesticated swine (pigs and hogs), ruminants, horses, poultry, and the like.

The terms "small interfering RNA", "short interfering RNA", and "siRNA" are used interchangeably and refer to any nucleic acid molecule capable of mediating RNA interference (RNAi) or gene silencing. See e.g., Bass, 2001; Elbashir et al., 2001; and PCT International Publication Nos. WO 99/07409; WO 99/32619; WO 00/01846; WO 00/44895; WO 00/44914; WO 01/36646; WO 01/29058. A non-limiting example of an siRNA molecule of the presently disclosed subject matter is shown in SEQ ID NO: 17. In some embodiments, the siRNA comprises a double stranded polynucleotide molecule comprising complementary sense and antisense regions, wherein the antisense region comprises a sequence complementary to a region of a target nucleic acid molecule (for example, an mRNA encoding VHL). In some embodiments, the siRNA comprises a single stranded polynucleotide having self-complementary sense and antisense regions, wherein the antisense region comprises a sequence complementary to a region of a target nucleic acid molecule. In some embodiments, the siRNA comprises a single stranded polynucleotide having one or more loop structures and a stem comprising self complementary sense and antisense regions, wherein the antisense region comprises a sequence complementary to a region of a target nucleic acid molecule, and wherein the polynucleotide can be processed either in vivo or in vitro to generate an active siRNA capable of mediating RNAi. As used herein, siRNA molecules need not be limited to those molecules containing only RNA, but further encompass chemically modified nucleotides and non-nucleotides.

The term "gene expression" generally refers to the cellular processes by which a biologically active polypeptide is produced from a DNA sequence and exhibits a biological activity in a cell. As such, gene expression involves the processes of transcription and translation, but also involves post-transcriptional and post-translational processes that can influence a biological activity of a gene or gene product. These processes include, but are not limited to RNA syntheses, processing, and transport, as well as polypeptide synthesis, transport, and post-translational modification of polypeptides. Additionally, processes that affect protein-protein interactions within the cell (for example, the interaction between HIF-1α and VHL) can also affect gene expression as defined herein.

As used herein, the term "modulate" refers to a change in the expression level of a gene, or a level of RNA molecule or equivalent RNA molecules encoding one or more proteins or protein subunits, or activity of one or more proteins or protein subunits is upregulated or downregulated, such that expression, level, and/or activity is greater than or less than that observed in the absence of the modulator. For example, the term "modulate" can mean "inhibit" or "suppress", but the use of the word "modulate" is not limited to this definition.

As used herein, the terms "inhibit", "suppress", "downregulate", and grammatical variants thereof are used interchangeably and refer to an activity whereby gene expression (e.g., a level of an RNA encoding one or more gene products) is reduced below that observed in the absence of a composition of the presently disclosed subject matter. In some embodiments, inhibition results in a decrease in the steady state level of a target RNA. In some embodiments, inhibition results in an expression level of a gene product that is below that level observed in the absence of the modulator.

In some embodiments, the terms "inhibit", "suppress", "downregulate", and grammatical variants thereof refer to a biological activity of a polypeptide or polypeptide complex that is lower in the presence of a modulator than that which occurs in the absence of the modulator. For example, a modulator can inhibit the ability of a polypeptide (e.g., an HIF-1 polypeptide) to interact with its target (e.g., VHL and/or a promoter sequence comprising a hypoxia response element (HRE)). This can be accomplished by any mechanism, including but not limited to enhancing its existence in an inactive form (e.g., enhancing the complexing of an HIF-1 with VHL and/or inhibiting the dissociation of an HIF-1 from VHL) and/or by enhancing the rate of degradation of an HIF-1.

As used herein, the terms "gene" and "target gene" refer to a nucleic acid that encodes an RNA, for example, nucleic acid sequences including, but not limited to, structural genes encoding a polypeptide. The target gene can be a gene derived from a cell, an endogenous gene, a transgene, etc. The cell containing the target gene can be derived from or contained in any organism, for example an animal. The term "gene" also refers broadly to any segment of DNA associated with a biological function. As such, the term "gene" encompasses sequences including but not limited to a coding sequence, a promoter region, a transcriptional regulatory sequence, a non-expressed DNA segment that is a specific recognition sequence for regulatory proteins, a non-expressed DNA segment that contributes to gene expression, a DNA segment designed to have desired parameters, or combinations thereof. A gene can be obtained by a variety of methods, including cloning from a biological sample, synthesis based on known or predicted sequence information, and recombinant derivation of an existing sequence.

In some embodiments, a gene is a hypoxia-inducible gene. As used herein, a "hypoxia-inducible gene" is a gene for which the expression level increases in response to hypoxia. In some embodiments, a hypoxia-inducible gene is a gene that is characterized by upregulated transcription in response to hypoxic conditions. Exemplary hypoxia-inducible genes thus include genes with hypoxia response elements (HREs) in their promoters. Under hypoxic conditions, transcription of these genes is induced as a result of activated HIF-1 binding to the HREs. Also as used herein, a hypoxia-inducible gene is a gene for which an activity of the gene product changes in response to hypoxia. In these embodiments, a hypoxia-inducible gene is a gene for which the polypeptide encoded by the gene experiences a change in state in response to hypoxia. Such a change in state includes, but is not limited to a post-transcriptional modification or an interaction with another molecule (for example, a protein-protein interaction). Thus, as used herein, the term hypoxia-inducible gene includes, but is not limited to HIF-1α and VHL, each of which undergoes a change in state (in this example, a dissociation one from the other) in response to hypoxia.

As is understood in the art, a gene comprises a coding strand and a non-coding strand. As used herein, the terms "coding strand" and "sense strand" are used interchangeably, and refer to a nucleic acid sequence that has the same sequence of nucleotides as an mRNA from which the gene product is translated. As is also understood in the art, when the coding strand and/or sense strand is used to refer to a DNA molecule, the coding/sense strand includes thymidine residues instead of the uridine residues found in the corresponding mRNA. Additionally, when used to refer to a DNA molecule, the coding/sense strand can also include additional elements not found in the mRNA including, but not limited to promoters, enhancers, and introns. Similarly, the terms "template strand" and "antisense strand" are used interchangeably and refer to a nucleic acid sequence that is complementary to the coding/sense strand.

As used herein, the terms "complementarity" and "complementary" refer to a nucleic acid that can form one or more hydrogen bonds with another nucleic acid sequence by either traditional Watson-Crick or other non-traditional types of interactions.

As used herein, the phrase "percent complementarity" refers to the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). The terms "100% complementary", "fully complementary", and "perfectly complementary" indicate that all of the contiguous residues of a nucleic acid sequence can hydrogen bond with the same number of contiguous residues in a second nucleic acid sequence.

As used herein, the term "cell" is used in its usual biological sense. In some embodiments, the cell is present in an organism, for example, mammals such as humans, cows, sheep, apes, monkeys, swine, dogs, cats, and rodents. In some embodiments, the cell is a eukaryotic cell (e.g., a mammalian cell, such as a human cell). The cell can be of somatic or germ line origin, totipotent or pluripotent, dividing or non-dividing. The cell can also be derived from or can comprise a gamete or embryo, a stem cell, or a fully differentiated cell.

As used herein, the term "RNA" refers to a molecule comprising at least one ribonucleotide residue. By "ribonucleotide" is meant a nucleotide with a hydroxyl group at the 2' position of a β-D-ribofuranose moiety. The terms encompass double stranded RNA, single stranded RNA, RNAs with both double stranded and single stranded regions, isolated RNA such as partially purified RNA, essentially pure RNA, synthetic RNA, recombinantly produced RNA, as well as altered RNA, or analog RNA, that differs from naturally occurring RNA by the addition, deletion, substitution, and/or alteration of one or more nucleotides. Such alterations can include addition of non-nucleotide material. Nucleotides in the RNA molecules of the presently disclosed subject matter can also comprise non-standard nucleotides, such as non-naturally occurring nucleotides or chemically synthesized nucleotides or deoxynucleotides. These altered RNAs can be referred to as analogs or analogs of a naturally occurring RNA.

As used herein, the phrase "double stranded RNA" refers to an RNA molecule at least a part of which is in Watson-Crick base pairing forming a duplex. As such, the term is to be understood to encompass an RNA molecule that is either fully or only partially double stranded. Exemplary double stranded RNAs include, but are not limited to molecules comprising at least two distinct RNA strands that are either partially or fully duplexed by intermolecular hybridization. Additionally, the term is intended to include a single RNA molecule that by intramolecular hybridization can form a double stranded region (for example, a hairpin). Thus, as used herein the phrases "intermolecular hybridization" and "intramolecular hybridization" refer to double stranded molecules for which the nucleotides involved in the duplex formation are present on different molecules or the same molecule, respectively.

As used herein, the phrase "double stranded region" refers to any region of a nucleic acid molecule that is in a double stranded conformation via hydrogen bonding between the nucleotides including, but not limited to hydrogen bonding between cytosine and guanosine, adenosine and thymidine, adenosine and uracil, and any other nucleic acid duplex as would be understood by one of ordinary skill in the art. The length of the double stranded region can vary from about 15 consecutive basepairs to several thousand basepairs.

As used herein, the terms "corresponds to", "corresponding to", and grammatical variants thereof refer to a nucleotide sequence that is 100% identical to at least 19 contiguous nucleotides of a nucleic acid sequence of a hypoxia-inducible gene. Thus, a first nucleic acid sequence that "corresponds to" a coding strand of a hypoxia-inducible gene is a nucleic acid sequence that is 100% identical to at least 19 contiguous nucleotides of a hypoxia-inducible gene, including, but not limited to 5' untranslated sequences, exon sequences, intron sequences, and 3' untranslated sequences.

The term "tumor" as used herein encompasses both primary and metastasized solid tumors and carcinomas of any tissue in a subject, including, but not limited to breast; colon; rectum; lung; oropharynx; hypopharynx; esophagus; stomach; pancreas; liver; gallbladder; bile ducts; small intestine;

urinary tract including kidney, bladder and urothelium; female genital tract including cervix, uterus, ovaries (e.g., choriocarcinoma and gestational trophoblastic disease); male genital tract including prostate, seminal vesicles, testes and germ cell tumors; endocrine glands including thyroid, adrenal, and pituitary; skin (e.g., hemangiomas and melanomas), bone or softtissues; blood vessels (e.g., Kaposi's sarcoma); brain, nerves, eyes, and meninges (e.g., astrocytomas, gliomas, glioblastomas, retinoblastomas, neuromas, neuroblastomas, Schwannomas and meningiomas). The term "tumor" also encompasses solid tumors arising from hematopoietic malignancies such as leukemias, including chloromas, plasmacytomas, plaques and tumors of mycosis fungoides and cutaneous T-cell lymphoma/leukemia, and lymphomas including both Hodgkin's and non-Hodgkin's lymphomas. The term "tumor" also encompasses radioresistant and/or chemoresistant tumors, including, but not limited to radioresistant and/or chemoresistant variants of the any of the tumor listed above.

The terms "radiosensitivity" and "radiosensitive", as used herein to describe a tumor, refer to a quality of susceptibility to treatment using ionizing radiation. Thus, radiotherapy can be used to delay growth of a radiosensitive tumor. Radiosensitivity can be quantified by determining a minimal amount of ionizing radiation that can be used to delay tumor growth. Thus, the term "radiosensitivity" refers to a quantitative range of radiation susceptibility.

The terms "sensitivity to chemotherapy", "chemosensitivity", and "chemosensitive", as used herein to describe a tumor, refer to a quality of susceptibility to treatment using chemotherapy. Thus, chemotherapy can be used to delay growth of a tumor sensitive to chemotherapy. Sensitivity of chemotherapy can be quantified by determining a minimal dosage of chemotherapy that can be used to delay tumor growth. Thus, the phrase "sensitivity to chemotherapy" refers to a quantitative range of chemotherapy susceptibility.

The terms "radiation resistant tumor" and "radioresistant tumor" each generally refer to a tumor that is substantially unresponsive to radiotherapy when compared to other tumors. Representative radiation resistant tumor models include glioblastoma multiforme and melanoma. Similarly, the terms "chemotherapy resistant tumor" and "chemoresistant tumor" generally refer to a tumor that is substantially unresponsive to chemotherapy when compared to other tumors.

The term "delaying tumor growth" refers to a decrease in duration of time required for a tumor to grow a specified amount. For example, treatment with the compositions and/or methods disclosed herein can delay the time required for a tumor to increase in volume 3-fold relative to an initial day of measurement (day 0) or the time required to grow to 1 cm³.

The term "increase," as used herein to refer to a change in radiosensitivity and/or sensitivity to chemotherapy of a tumor, refers to change that renders a tumor more susceptible to destruction by ionizing radiation and/or chemotherapy. Alternatively stated, an increase in radiosensitivity and/or chemosensitivity refers to a decrease in the minimal amount of ionizing radiation and/or chemotherapy that effectively delays tumor growth. An increase in radiosensitivity and/or chemosensitivity can also comprise delayed tumor growth when a composition of the presently disclosed subject matter is administered with radiation and/or chemotherapy as compared to a same dose of radiation and/or chemotherapy alone. In some embodiments, an increase in radiosensitivity and/or chemosensitivity refers to an increase of at least about 2-fold, in some embodiments an increase of at least about 5-fold, and in some embodiments an increase of at least 10-fold. In some embodiments of the presently disclosed subject matter, an increase in radiosensitivity and/or chemosensitivity comprises a transformation of a radioresistant and/or chemoresistant tumor to a radiosensitive and/or chemosensitive tumor.

The term "tumor regression" generally refers to any one of a number of indices that suggest change within the tumor to a less developed form. Such indices include, but are not limited to a destruction of tumor vasculature (for example, a decrease in vascular length density or a decrease in blood flow), a decrease in tumor cell survival, a decrease in tumor volume, and/or a decrease in tumor growth rate. Methods for assessing tumor growth delay and tumor regression are known to the skilled artisan.

The term "nucleic acid molecule" refers to deoxyribonucleotides or ribonucleotides and polymers thereof in either single- or double-stranded form. Unless specifically limited, the term encompasses nucleic acids containing known analogues of natural nucleotides that have similar properties as the reference natural nucleic acid. Unless otherwise indicated, a particular nucleotide sequence also implicitly encompasses complementary sequences, subsequences, elongated sequences, as well as the sequence explicitly indicated. The terms "nucleic acid molecule" or "nucleotide sequence" can also be used in place of "gene", "DNA", "cDNA", "RNA", or "mRNA". Nucleic acids can be derived from any source, including any organism.

The term "isolated", as used in the context of a nucleic acid molecule or polypeptide, indicates that the nucleic acid molecule or polypeptide exists apart from its native environment and is not a product of nature. An isolated nucleic acid molecule or polypeptide can exist in a purified form or can exist in a non-native environment such as a host cell.

The terms "identical" or percent "identity" in the context of two or more nucleotide or polypeptide sequences refer to two or more sequences or subsequences that are the same or have a specified percentage of amino acid residues or nucleotides that are the same, when compared and aligned for maximum correspondence, as measured using one of the sequence comparison algorithms disclosed herein or by visual inspection.

The term "substantially identical", in the context of two nucleotide sequences, refers to two or more sequences or subsequences that have in some embodiments at least 60%, in some embodiments about 70%, in some embodiments about 80%, in some embodiments about 90%, in some embodiments about 95%, in some embodiments, about 97%, and in some embodiments about 99% nucleotide identity, when compared and aligned for maximum correspondence, as measured using one of the following sequence comparison algorithms (described herein below) or by visual inspection. In some embodiments, the substantial identity exists in nucleotide sequences of at least 50 residues, in some embodiments in nucleotide sequence of at least about 100 residues, in some embodiments in nucleotide sequences of at least about 150 residues, and in some embodiments in nucleotide sequences comprising complete coding sequences.

In one aspect, polymorphic sequences can be substantially identical sequences. The terms "polymorphic", "polymorphism", and "polymorphic variants" refer to the occurrence of two or more genetically determined alternative sequences or alleles in a population. An allelic difference can be as small as one base pair. As used herein in regards to a nucleotide or polypeptide sequence, the term "substantially identical" also refers to a particular sequence that varies from another sequence by one or more deletions, substitutions, or additions, the net effect of which is to retain biological activity of a gene, gene product, or sequence of interest.

For sequence comparison, typically one sequence acts as a reference sequence to which test sequences are compared. When using a sequence comparison algorithm, test and reference sequences are entered into a computer program, subsequence coordinates are designated if necessary, and sequence algorithm program parameters are selected. The sequence comparison algorithm then calculates the percent sequence identity for the designated test sequence(s) relative to the reference sequence, based on the selected program parameters.

Optimal alignment of sequences for comparison can be conducted, e.g., by the local homology algorithm of Smith & Waterman, 1981, by the homology alignment algorithm of Needleman & Wunsch, 1970, by the search for similarity method for Pearson & Lipman, 1988, by computerized implementations of these algorithms (GAP, BESTFIT, FASTA, and TFASTA, in the Wisconsin Genetics Software Package, available from Accelrys Inc., San Diego, Calif., United States of America), or by visual inspection. See generally, Ausubel, 1995.

In some embodiments, an algorithm for determining percent sequence identity and sequence similarity is the BLAST algorithm, which is described by Altschul et al., 1990. Software for performing BLAST analyses is publicly available through the website of the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength W=11, an expectation E=10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See Henikoff & Henikoff, 1992.

In addition to calculating percent sequence identity, the BLAST algorithm also performs a statistical analysis of the similarity between two sequences. See e.g., Karlin & Altschul, 1993. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is in some embodiments less than about 0.1, in some embodiments less than about 0.01, and in some embodiments less than about 0.001.

Another indication that two nucleotide sequences are substantially identical is that the two molecules specifically or substantially hybridize to each other under stringent conditions. In the context of nucleic acid hybridization, two nucleic acid sequences being compared can be designated a "probe" and a "target". A "probe" is a reference nucleic acid molecule, and a "target" is a test nucleic acid molecule, often found within a heterogeneous population of nucleic acid molecules. A "target sequence" is synonymous with a "test sequence".

The phrase "hybridizing substantially to" refers to complementary hybridization between a probe nucleic acid molecule and a target nucleic acid molecule and embraces minor mismatches that can be accommodated by reducing the stringency of the hybridization media to achieve the desired hybridization.

"Stringent hybridization conditions" and "stringent hybridization wash conditions" in the context of nucleic acid hybridization experiments such as Southern and Northern blot analysis are both sequence- and environment-dependent. Longer sequences hybridize specifically at higher temperatures. An extensive guide to the hybridization of nucleic acids is found in Tijssen, 1993. Generally, highly stringent hybridization and wash conditions are selected to be about 5° C. lower than the thermal melting point ($T_m$) for the specific sequence at a defined ionic strength and pH. Typically, under "stringent conditions" a probe will hybridize specifically to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of highly stringent hybridization conditions for Southern or Northern Blot analysis of complementary nucleic acids having more than about 100 complementary residues is overnight hybridization in 50% formamide with 1 mg of heparin at 42° C. An example of highly stringent wash conditions is 15 minutes in 0.1× standard saline citrate (SSC), 0.1% (w/v) SDS at 65° C. Another example of highly stringent wash conditions is 15 minutes in 0.2×SSC buffer at 65° C. (see Sambrook & Russell, 2001 for a description of SSC buffer and other stringency conditions). Often, a high stringency wash is preceded by a lower stringency wash to remove background probe signal. An example of medium stringency wash conditions for a duplex of more than about 100 nucleotides is 15 minutes in 1×SSC at 45° C. Another example of medium stringency wash for a duplex of more than about 100 nucleotides is 15 minutes in 4-6×SSC at 40° C. For short probes (e.g., about 10 to 50 nucleotides), stringent conditions typically involve salt concentrations of less than about 1M Na$^+$ ion, typically about 0.01 to 1M Na$^+$ ion concentration (or other salts) at pH 7.0-8.3, and the temperature is typically at least about 30° C. Stringent conditions can also be achieved with the addition of destabilizing agents such as formamide. In general, a signal to noise ratio of 2-fold or higher than that observed for an unrelated probe in the particular hybridization assay indicates detection of a specific hybridization.

The following are examples of hybridization and wash conditions that can be used to clone homologous nucleotide sequences that are substantially identical to reference nucleotide sequences of the presently disclosed subject matter: a probe nucleotide sequence hybridizes in one example to a target nucleotide sequence in 7% sodium dodecyl sulfate (SDS), 0.5M NaPO$_4$, 1 mm EDTA at 50° C. followed by washing in 2×SSC, 0.1% SDS at 50° C.; in another example, a probe and target sequence hybridize in 7% sodium dodecyl sulfate (SDS), 0.5M NaPO$_4$, 1 mm EDTA at 50° C. followed by washing in 1×SSC, 0.1% SDS at 50° C.; in another example, a probe and target sequence hybridize in 7% sodium dodecyl sulfate (SDS), 0.5M NaPO$_4$, 1 mm EDTA at 50° C. followed by washing in 0.5×SSC, 0.1% SDS at 50° C.; in another example, a probe and target sequence hybridize in 7% sodium dodecyl sulfate (SDS), 0.5M NaPO$_4$, 1 mm EDTA at 50° C. followed by washing in 0.1×SSC, 0.1% SDS at 50° C.; in yet another example, a probe and target sequence hybridize in 7% sodium dodecyl sulfate (SDS), 0.5M NaPO$_4$, 1 mm EDTA at 50° C. followed by washing in 0.1×SSC, 0.1% SDS at 65° C.

The term "subsequence" refers to a sequence of a nucleic acid or polypeptide that comprises a part of a longer nucleic acid or polypeptide sequence.

The term "elongated sequence" refers to an addition of nucleotides (or other analogous molecules) or amino acid residues incorporated into the nucleic acid or polypeptide. For example, a polymerase (e.g., a DNA polymerase) can add sequences at the 3' terminus of the nucleic acid molecule. In addition, the nucleotide sequence can be combined with other DNA sequences, such as promoters, promoter regions, enhancers, polyadenylation signals, intronic sequences, additional restriction enzyme sites, multiple cloning sites, and other coding segments.

The terms "operatively linked" and "operably linked", as used herein, refer to a nucleic acid molecule in which a promoter region is connected to a nucleotide sequence in such a way that the transcription of that nucleotide sequence is controlled and regulated by the promoter region. Similarly, a nucleotide sequence is said to be under the "transcriptional control" of a promoter to which it is operably linked. Techniques for operatively linking a promoter region to a nucleotide sequence are known in the art.

The terms "heterologous gene", "heterologous DNA sequence", "heterologous nucleotide sequence", "exogenous nucleic acid molecule", or "exogenous DNA segment", as used herein, each refer to a sequence that originates from a source foreign to an intended host cell and/or, if from the same source, is modified from its original form. Thus, a heterologous gene in a host cell includes a gene that is endogenous to the particular host cell but has been modified, for example by mutagenesis and/or by isolation from native transcriptional regulatory sequences. The terms also include non-naturally occurring multiple copies of a naturally occurring nucleotide sequence. Thus, the terms refer in some embodiments to a DNA segment that is foreign or heterologous to the cell, or is homologous to the cell but in a position within the host cell nucleic acid wherein the element is not ordinarily found.

The term "expression vector" as used herein refers to a nucleotide sequence capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The construct comprising the nucleotide sequence of interest can be chimeric. The construct can also be one that is naturally occurring but has been obtained in a recombinant form useful for heterologous expression.

The term "promoter" or "promoter region" each refers to a nucleotide sequence within a gene that is positioned 5' to a coding sequence and functions to direct transcription of the coding sequence. The promoter region comprises a transcriptional start site, and can additionally include one or more transcriptional regulatory elements. In some embodiments, a method for the presently disclosed subject matter employs a hypoxia inducible promoter.

A "minimal promoter" is a nucleotide sequence that has the minimal elements required to enable basal level transcription to occur. As such, minimal promoters are not complete promoters but rather are subsequences of promoters that are capable of directing a basal level of transcription of a reporter construct in an experimental system. Minimal promoters include but are not limited to the CMV minimal promoter, the HSV-tk minimal promoter, the simian virus 40 (SV40) minimal promoter, the human β-actin minimal promoter, the human EF2 minimal promoter, the adenovirus E1B minimal promoter, and the heat shock protein (hsp) 70 minimal promoter. Minimal promoters are often augmented with one or more transcriptional regulatory elements to influence the transcription of an operably linked gene. For example, cell-type-specific or tissue-specific transcriptional regulatory elements can be added to minimal promoters to create recombinant promoters that direct transcription of an operably linked nucleotide sequence in a cell-type-specific or tissue-specific manner Different promoters have different combinations of transcriptional regulatory elements. Whether or not a gene is expressed in a cell is dependent on a combination of the particular transcriptional regulatory elements that make up the gene's promoter and the different transcription factors that are present within the nucleus of the cell. As such, promoters are often classified as "constitutive", "tissue-specific", "cell-type-specific", or "inducible", depending on their functional activities in vivo or in vitro. For example, a constitutive promoter is one that is capable of directing transcription of a gene in a variety of cell types. Exemplary constitutive promoters include the promoters for the following genes which encode certain constitutive or "housekeeping" functions: hypoxanthine phosphoribosyl transferase (HPRT), dihydrofolate reductase (DHFR; (Scharfmann et al., 1991), adenosine deaminase, phosphoglycerate kinase (PGK), pyruvate kinase, phosphoglycerate mutase, the β-actin promoter (see e.g., Williams et al., 1993), and other constitutive promoters known to those of skill in the art. "Tissue-specific" or "cell-type-specific" promoters, on the other hand, direct transcription in some tissues and cell types but are inactive in others. Exemplary tissue-specific promoters include the PSA promoter (Yu et al., 1999; Lee et al., 2000), the probasin promoter (Greenberg et al., 1994; Yu et al., 1999), and the MUC1 promoter (Kurihara et al., 2000) as discussed above, as well as other tissue-specific and cell-type specific promoters known to those of skill in the art.

The term "transcriptional regulatory sequence" or "transcriptional regulatory element", as used herein, each refers to a nucleotide sequence within the promoter region that enables responsiveness to a regulatory transcription factor. Responsiveness can encompass a decrease or an increase in transcriptional output and is mediated by binding of the transcription factor to the DNA molecule comprising the transcriptional regulatory element.

The term "transcription factor" generally refers to a protein that modulates gene expression by interaction with the transcriptional regulatory element and cellular components for transcription, including RNA polymerase, Transcription Associated Factors (TAFs), chromatin-remodeling proteins, and any other relevant protein that impacts gene transcription.

The terms "reporter gene" or "marker gene" or "selectable marker" each refer to a heterologous gene encoding a product that is readily observed and/or quantitated. A reporter gene is heterologous in that it originates from a source foreign to an intended host cell or, if from the same source, is modified from its original form. Non-limiting examples of detectable reporter genes that can be operatively linked to a transcriptional regulatory region can be found in Alam & Cook, 1990 and PCT International Publication No. WO 97/47763. Exemplary reporter genes for transcriptional analyses include the lacZ gene (see e.g., Rose & Botstein, 1983), Green Fluorescent Protein (GFP; Cubitt et al., 1995), luciferase, and chloramphenicol acetyl transferase (CAT). Reporter genes for methods to produce transgenic animals include but are not limited to antibiotic resistance genes, for example the antibiotic resistance gene confers neomycin resistance. Any suitable reporter and detection method can be used, and it will be appreciated by one of skill in the art that no particular choice is essential to or a limitation of the presently disclosed subject matter.

An amount of reporter gene can be assayed by any method for qualitatively or quantitatively determining presence or activity of the reporter gene product. The amount of reporter gene expression directed by each test promoter region fragment is compared to an amount of reporter gene expression to a control construct comprising the reporter gene in the absence of a promoter region fragment. A promoter region fragment is identified as having promoter activity when there is significant increase in an amount of reporter gene expression in a test construct as compared to a control construct. The term "significant increase", as used herein, refers to an quantified change in a measurable quality that is larger than the margin of error inherent in the measurement technique, in one example an increase by about 2-fold or greater relative to a control measurement, in another example an increase by about 5-fold or greater, and in yet another example an increase by about 10-fold or greater.

Nucleic acids of the presently disclosed subject matter can be cloned, synthesized, recombinantly altered, mutagenized, or combinations thereof. Standard recombinant DNA and molecular cloning techniques used to isolate nucleic acids are known in the art. Exemplary, non-limiting methods are described by Silhavy et al.,1984; Ausubel et al.,1992; Glover & Hames, 1995; and Sambrook & Russell, 2001). Site-specific mutagenesis to create base pair changes, deletions, or small insertions is also known in the art as exemplified by publications (see e.g., Adelman et al., 1983; Sambrook & Russell, 2001).

III. Compositions

The compositions disclosed herein can be employed in vitro and/or in vivo in order to perform the disclosed methods. In some embodiments, the compositions described herein comprise an agent selected from the group consisting of an inhibitor of nitric oxide synthase, a nitric oxide scavenger, an inhibitor of NIF-1 nitrosylation, and combinations thereof.

III.A. Inhibitors of Nitric Oxide Synthase(s)

In some embodiments, an agent comprises an inhibitor of nitric oxide synthase (NOS). As is known in the art, there are several nitric oxide synthases, including but not limited to neural/neuronal NOS (nNOS; also referred to as NOS1), inducible NOS (iNOS; also referred to as NOS2), and endothelial NOS (eNOS; also referred to as NOS3). Nucleic acid and amino acid sequences for each of these NOS gene products are present in the GENBANK® database, each of which is expressly incorporated by reference herein in its entirety. For example, human NOS sequences present in the GENBANK® database include GENBANK® Accession Nos. U17327 and AAA62405 (nNOS nucleic acid and amino acid sequences, respectively), NM_000625 and NP_000616 (iNOS nucleic acid and amino acid sequences, respectively), and BC069465 and AAH69465 (eNOS nucleic acid and amino acid sequences, respectively).

Various inhibitors of NOS have been identified, some of which are selective and other of which are non-selective for one or more specific NOS type. As used herein, a "selective" or "specific" NOS inhibitor demonstrates markedly greater specificity for one of the NOS types (e.g., iNOS) than it does for the other two (e.g., eNOS and nNOS), while "non-selective" or "non-specific" NOS inhibitors demonstrate approximately equivalent inhibition of two or more of the NOS types. Both non-selective and selective NOS inhibitors are appropriate for use in the methods and compositions for the presently disclosed subject matter. Representative NOS inhibitors thus include, but are not limited to L-N(6)-(1-iminoethyl) lysine tetrazole-amide (SC-51); aminoguanidine (AG); guanidinoethyldisulfide; L-NG-nitroarginine methyl ester; mercaptoethylguanidine (MEG); $N^\omega$-nitro-L-arginine methyl ester (L-NAME); N-(3-(aminomethyl)benzyl)acetamidine (1400W); $N^G$-monomethyl-L-arginine (L-NMMA); 7-nitroindazole (7-NI), L-NIL($N^6$-(1-iminoethyl)-lysine (L-NIL); and $N^5$-(1-iminoethyl)-L-ornithine (L-NIO); as well as their pharmaceutically acceptable salts and other derivatives.

III.B. Nitric Oxide Scavengers

In some embodiments, a composition of the presently disclosed subject matter comprises a nitric oxide (NO) scavenger. As used herein, the phrase "nitric oxide scavenger" refers to a molecule that binds to nitric oxide or otherwise makes the nitric oxide less available to take part in a biochemical process within a cell. Nitric oxide scavengers are also known, and include, but are not limited to vitamin B12, particularly in the hydroxocobalamin form; 2-(4-carboxyphenyl)-4,4,5,5-tetramethylimidazoline-1-oxyl-3-oxide (carboxy-PTIO); diethyldithiocarbamate; AMD6221 (ruthenium[hydrogen(diethylenetrinitrilo)pentaacetato]chloride); and N-dithiocarboxysarcosine (DTCS), as well as pharmaceutically acceptable salts and other derivatives thereof.

III.C. Inhibitors of HIF-1 Nitrosylation

In some embodiments, a composition of the presently disclosed subject matter comprises an inhibitor of HIF-1 nitrosylation. As used herein, the phrase "inhibitor of HIF-1 nitrosylation" refers to any molecule that inhibits, either completely or partially, nitrosylation of an HIF-1 polypeptide. As such, this phrase encompasses NOS inhibitors, NO scavengers, and any other molecule that can inhibit the nitrosylation of an HIF-1 polypeptide. Representative other molecules include, but are not limited to peptides, peptide mimetics, proteins, antibodies or fragments thereof, small molecules, nucleic acids, and combinations thereof. The term "small molecule" as used herein refers to a compound, for example an organic compound, with a molecular weight in one example of less than about 1,000 daltons, in another example less than about 750 daltons, in another example less than about 600 daltons, and in yet another example less than about 500 daltons. A small molecule also has in one example a computed log octanol-water partition coefficient in the range of about −4 to about +14, more preferably in the range of about −2 to about +7.5.

As is known in the art, polypeptides such as HIF-1 can be S-nitrosylated on cysteine residues. As disclosed herein, nitrosylation of C533 of murine HIF-1α (which corresponds to C520 of human HIF-1α) interferes with the interaction between HIF-1α and VHL, which in turn inhibits the ubiquitylation and subsequent degradation of HIF-1α by the proteasome. S-nitrosylation of HIF-1α at this highly conserved cysteine (see also SEQ ID NOs. 1-21 showing the conservation of this cysteine in various animal species) thus results in an increased persistence of HIF-1α in the cell, leading to higher HIF-1α activity. Accordingly, inhibitors of HIF-1α nitrosylation can be employed to reduce HIF-1 activity in cells.

III.D. Formulations

The compositions of the presently disclosed subject matter comprise in some embodiments a composition that includes a pharmaceutically acceptable carrier. Any suitable pharmaceutical formulation can be used to prepare the adenovirus vectors for administration to a subject.

For example, suitable formulations can include aqueous and non-aqueous sterile injection solutions which can contain anti-oxidants, buffers, bacteriostats, bactericidal antibiotics and solutes which render the formulation isotonic with the bodily fluids of the intended recipient; and aqueous and non-aqueous sterile suspensions which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are SDS, in one example in the range of 0.1 to 10 mg/ml, in another example about 2.0 mg/ml; and/or mannitol or another sugar, for example in the range of 10 to 100 mg/ml, in another example about 30 mg/ml; and/or phosphate-buffered saline (PBS).

It should be understood that in addition to the ingredients particularly mentioned above the formulations of this presently disclosed subject matter can include other agents conventional in the art having regard to the type of formulation in question. For example, sterile pyrogen-free aqueous and non-aqueous solutions can be used.

The therapeutic regimens and compositions of the presently disclosed subject matter can be used with additional adjuvants or biological response modifiers including, but not limited to, the cytokines IFN-α, IFN-γ, IL2, IL4, IL6, TNF, or other cytokine affecting immune cells. In accordance with this aspect of the presently disclosed subject matter, the disclosed nucleic acid molecules can be administered in combination therapy with one or more of these cytokines.

III.E. Administration

Administration of the compositions of the presently disclosed subject matter can be by any method known to one of ordinary skill in the art, including, but not limited to intravenous administration, intrasynovial administration, transdermal administration, intramuscular administration, subcutaneous administration, topical administration, rectal administration, intravaginal administration, intratumoral administration, oral administration, buccal administration, nasal administration, parenteral administration, inhalation, and insufflation. In some embodiments, suitable methods for administration of a composition of the presently disclosed subject matter include, but are not limited to intravenous or intratumoral injection. Alternatively, a composition can be deposited at a site in need of treatment in any other manner, for example by spraying a composition comprising a composition within the pulmonary pathways. The particular mode of administering a composition of the presently disclosed subject matter depends on various factors, including the distribution and abundance of cells to be treated, whether a vector is employed, additional tissue- or cell-targeting features of the vector and/or composition, and mechanisms for metabolism or removal of the composition from its site of administration. For example, relatively superficial tumors can be injected intratumorally. By contrast, internal tumors can be treated by intravenous injection.

In some embodiments, the method for administration encompasses features for regionalized delivery or accumulation at the site in need of treatment. In some embodiments, a composition is delivered intratumorally. In some embodiments, selective delivery of a composition to a tumor is accomplished by intravenous injection of the composition.

Alternatively or in addition, a composition of the presently disclosed subject matter can be provided at a pre-determined site using an implantable device containing the composition, whereby longer term delivery of the composition to a target tissue can be accomplished. Representative implantable devices are known in the art. For example, absorbable thermoplastic elastomers have been developed to address the need in medical device development for an elastic material (e.g., U.S. Pat. Nos. 5,468,253 and 5,713,920). In addition, absorbable polymeric liquids and pastes have been developed to increase the range of physical properties exhibited by the aliphatic polyesters based on glycolide, lactide, p-dioxanone, 5,5-dimethyl-1,3-dioxan-2-one, trimethylene carbonate, and ε-caprolactone (e.g., U.S. Pat. Nos. 5,411,554; 5,599,852; 5,631,015; 5,653,992; 5,688,900; 5,728,752; and 5,824,333).

U.S. Pat. Nos. 5,573,934 and 5,858,746 (both to Hubbell et al.) disclosed the use of photocurable polymers to encapsulate biological materials including drugs, proteins, and cells in a hydrogel. The hydrogel was formed from a water soluble biocompatible macromer containing at least two free radical polymerizable substituents and either a thermal or light activated free radical initiator. An example of such a photoreactive system is an acrylate ester endcapped poly(ethylene glycol) containing ethyl eosin and a tertiary amine. After a series of light activated reactions between ethyl eosin and the amine, the acrylate endgroups polymerize into short segments that result in a crosslinked polymeric network composed of poly(ethylene glycol) chains radiating outward from the acrylate oligomers. The physical and mechanical properties of the resulting hydrogel are dependent on the reproducibility of the free radical oligomerization reaction.

U.S. Pat. No. 5,410,016 in the form of photocurable, segmented block copolymers composed not only of water soluble segments, such as poly(ethylene glycol), but also of segments with hydrolizable groups, in particular, with short segments of aliphatic polyesters. In this way, the resulting hydrogel breaks down into soluble units in vitro and in vivo in a controlled fashion. The photochemistry is the same and based on the free radical polymerization of acrylate and methacrylate endgroups.

Other implantable devices are described in U.S. Pat. Nos. 7,009,034; 7,011,842; and 7,012,126.

For delivery of compositions to pulmonary pathways, the presently disclosed subject matter can be formulated as an aerosol or coarse spray. Methods for preparation and administration of aerosol or spray formulations can be found, for example, in Cipolla et al., 2000, and in U.S. Pat. Nos. 5,858,784; 6,013,638; 6,022,737; and 6,136,295.

III.F. Dosage

An effective dose of a composition of the presently disclosed subject matter is administered to a subject in need thereof. A "therapeutically effective amount" is an amount of the composition sufficient to produce a measurable response (e.g., a cytolytic response in a subject being treated). In some embodiments, an activity that inhibits tumor growth is measured. Actual dosage levels of active ingredients in the compositions of the presently disclosed subject matter can be varied so as to administer an amount of the active compound(s) that is effective to achieve the desired therapeutic response for a particular subject. The selected dosage level can depend upon the activity of the therapeutic composition, the route of administration, combination with other drugs or treatments, the severity of the condition being treated, and the condition and prior medical history of the subject being treated. However, it is within the skill of the art to start doses of the compositions at levels lower than required to achieve the desired therapeutic effect and to gradually increase the dosage until the desired effect is achieved.

The potency of a composition can vary, and therefore a "therapeutically effective" amount can vary. However, one skilled in the art can readily assess the potency and efficacy of a candidate composition of the presently disclosed subject matter and adjust the therapeutic regimen accordingly.

After review of the disclosure of the presently disclosed subject matter presented herein, one of ordinary skill in the art can tailor the dosages to an individual patient, taking into account the particular formulation, method for administration to be used with the composition, and tumor size. Further calculations of dose can consider patient height and weight, severity and stage of symptoms, and the presence of additional deleterious physical conditions. Such adjustments or variations, as well as evaluation of when and how to make such adjustments or variations, are well known to those of ordinary skill in the art of medicine.

For example, for local administration of viral expression vectors, previous clinical studies have demonstrated that up to $10^{13}$ plaque-forming units (pfu) of virus can be injected with minimal toxicity. In human patients, $1 \times 10^9$-$1 \times 10^{13}$ pfu are routinely used (see Habib et al., 1999). To determine an appropriate dose within this range, preliminary treatments can begin with $1 \times 10^9$ pfu, and the dose level can be escalated in the absence of dose-limiting toxicity. Toxicity can be assessed using criteria set forth by the National Cancer Institute and is reasonably defined as any grade 4 toxicity or any grade 3 toxicity persisting more than 1 week. Dose is also modified to maximize anti-tumor or anti-angiogenic activity. Representative criteria and methods for assessing anti-tumor and/or anti-angiogenic activity are described herein below. With replicative virus vectors, a dosage of about $1 \times 10^7$ to $1 \times 10^8$ pfu can be used in some instances.

IV. Applications

The presently disclosed subject matter provides methods for inhibiting nitric oxide synthase(s) activity in a cell in a subject. In some embodiments, the methods comprise administering to the cell in the subject a composition comprising (a) an agent selected from the group consisting of (i) an inhibitor of nitric oxide synthase; (ii) a nitric oxide scavenger; (iii) an inhibitor of HIF-1 nitrosylation; and (iv) combinations thereof, whereby nitric oxide synthase activity in the cell is inhibited. This general strategy can be employed in several areas, as disclosed in more detail hereinbelow.

IV.A. Methods for Inhibiting HIF-1 Activity

In some embodiments, the presently disclosed subject matter provides methods and compositions for inhibiting HIF-1 activity in a cell. In some embodiments, the cell is a tumor cell, and in some embodiments, the tumor cell is present within a subject including, but not limited to a mammals such as a human.

As disclosed herein, the presently disclosed subject matter provides compositions for inhibiting HIF-1 activity in a cell by inhibiting nitrosylation of HIF-1α, which in turn results in enhanced degradation of HIF-1α mediated by the ubiquitin-proteasome pathway. As also disclosed herein, a highly conserved cysteine residue has been found to be a site for nitrosylation. This highly conserved cysteine corresponds to the positions listed in Table 1.

TABLE 1

Conserved Cysteines in HIF-1α from Various Species

| Species | Cys Position |
|---|---|
| Spalax judaei | 520 of SEQ ID NO: 1 |
| Eospalax baileyi | 521 of SEQ ID NO: 2 |
| Mus musculus | 533 of SEQ ID NO: 3 |
| Rattus norvegicus | 520 of SEQ ID NO: 4 |
| Microtus oeconomus | 520 of SEQ ID NO: 5 |
| Homo sapiens | 520 of SEQ ID NO: 6 |
| Pongo pygmaeus | 521 of SEQ ID NO: 7 |
| Macaca fascicularis | 520 of SEQ ID NO: 8 |
| Spermophilus tridecemlineatus | 520 of SEQ ID NO: 9 |
| Bos taurus | 520 of SEQ ID NO: 10 |
| Pantholops hodgsonii | 520 of SEQ ID NO: 11 |
| Canis familiaris | 520 of SEQ ID NO: 12 |
| Oryctolagus cuniculus | 520 of SEQ ID NO: 13 |
| Gallus gallus | 518 of SEQ ID NO: 14 |
| Xenopus laevis | 516 of SEQ ID NO: 16 |

Accordingly, the methods and compositions disclosed herein inhibit HIF-1 activity in some embodiments by inhibiting nitrosylation of the listed cysteine residues.

IV.B. Methods for Treating Tumor Cells and/or Cancer Cells

The presently disclosed methods and compositions can also be employed for treatment of tumor cells and/or cancer cells. In some embodiments, the methods comprise contacting the tumor cell and/or the cancer cell with the presently disclosed compositions (e.g., by administering the compositions to a subject that has the tumor cell and/or the cancer cell). In some embodiments, the compositions are selected from the group consisting of inhibitors of nitric oxide synthase, nitric oxide scavengers, inhibitors of HIF-1 nitrosylation, and combinations thereof. In some embodiments, the methods and compositions disclosed herein treat the tumor cell and/or the cancer cell by inhibiting HIF-1 activity in the tumor cell and/or the cancer cell.

As such, the methods and compositions can act directly on the tumor cell and/or the cancer cell to modulate its growth and/or proliferation. However, the methods and compositions can also act indirectly on the tumor cell and/or the cancer cell to modulate its growth and/or proliferation by inhibiting HIF-1 activity in other cells that influence the growth and/or proliferation of the tumor cell and/or the cancer cell. For example, the methods and compositions can inhibit HIF-1 activity in tumor blood vessels (i.e., those blood vessels and other endothelial cells that provide nutrients and remove waste products from the tumor and/or cancer cells) and/or can inhibit tumor angiogenesis modulated by HIF-1 activity. While applicants do not wish to be bound by any particular theory of operation, the methods and compositions disclosed herein can be employed to interfere with the function and/or generation of tumor vasculature, thereby modulating tumor cell and/or cancer cell growth and/or proliferation.

Additionally, the methods and compositions disclosed herein can be employed for increasing the sensitivity of a tumor cell and/or a cancer cell to a treatment, such as surgical resection, radiotherapy, and/or chemotherapy, as discussed in more detail hereinbelow. As used herein, the phrase "increasing the sensitivity of a tumor cell and/or a cancer cell to a treatment" refers to an enhancement of the effect that a combination treatment including use of the presently disclosed methods and compositions has on tumor cell and/or cancer cell growth and/or proliferation as compared to the effect that a treatment would have had under the same conditions absent use of the presently disclosed methods and compositions. In some embodiments, the combination treatment employs the methods and/or compositions disclosed herein in conjunction with surgical resection, radiotherapy, and/or chemotherapy, and in some embodiments, the inclusion of a treatment comprising the methods and/or compositions disclosed herein results in a synergistic (i.e., more than additive) effect. Given the current limitations of surgical resection, radiotherapy, and/or chemotherapy, the presently disclosed subject matter provides an additional therapy that can be used to increase the efficacy of medical treatments directed towards modulating tumor cell and/or cancer cell growth and proliferation.

IV.C. Methods for Inhibiting an Inflammatory Response

The methods and compositions disclosed herein can also be employed for inhibiting inflammatory responses of cells (i.e., a cell in a subject). Also disclosed herein is the discovery that treatment of macrophages with inflammation-causing agents can result in the stabilization and activation of HIF-1α. As HIF-1α has been shown to be important in mediating inflammatory response, methods and compositions that inhibit the nitrosylation and stabilization of HIF-1α can also be used as anti-inflammatory agents.

IV.D. Methods and Compositions for Identifying New Nitrosylation Inhibitors

The presently disclosed subject matter also provides screening methods and compositions that can be employed for identifying potential inhibitors of nitrosylation of an HIF-1 polypeptide. In some embodiments, the methods comprise (a) providing a cell comprising a nucleic acid a nucleotide sequence comprising any of SEQ ID NOs: 18-21; (b) contacting the cell with a compound comprising a potential inhibitor of nitrosylation of an HIF-1 polypeptide; and (c) assaying nitrosylation of a cysteine residue present in the nucleic acid, whereby an inhibitor of nitrosylation of an HIF-1 polypeptide is identified. In some embodiments, the methods further comprise comparing a level of nitrosylation of the cysteine residue present in the nucleic acid to a level of nitrosylation of the cysteine residue present in the nucleic acid prior to the contacting step.

In some embodiments, the nucleic acid comprises an expression vector in which the nucleic acid is operably linked to a promoter that is active in the cell. In some embodiments, the expression vector is a transgene and the animal is a transgenic animal that expresses the nucleic acid. In some embodiments, the compound is administered to the transgenic animal via a route that results in the compound contacting the cell. In some embodiments, the cell is an in vitro cultured cell and the contacting is performed in vitro.

In some embodiments, the cell (e.g., an in vitro cultured cell or a cell in a transgenic animal) comprises an expression construct comprising one or more of SEQ ID NOs: 18-21 operably linked to a promoter. In some embodiments, the cell (e.g., an in vitro cultured cell or a cell in a transgenic animal) comprises an expression construct comprising one or more of SEQ ID NOs: 18-21 operably linked to a promoter, with the proviso that all cysteine residues present within SEQ ID NOs: 18-21 have been replaced with a non-nitrosylatable amino acid. An exemplary non-nitrolysable amino acid is serine.

The cells comprising the expression construct comprising one or more of SEQ ID NOs: 18-21 operably linked to a promoter (e.g., an in vitro cultured cell or a cell in a transgenic animal) can be employed for screening candidate compounds for an ability to modulate nitrosylation of HIF-1. As used herein, the terms "candidate substance" and "candidate compound" are used interchangeably and refer to a substance that is believed to be capable of modulating nitrosylation of the conserved cysteine present in any of SEQ ID NOs: 18-21. Exemplary candidate compounds that can be investigated using the methods and compositions disclosed herein include, but are not restricted to, agonists and antagonists of enzymes disclosed herein to influence HIF-1 nitrosylation (e.g., small molecule agonists and antagonists of a NOS and/or a PDH), peptides, small molecules, and antibodies and derivatives thereof, and combinations thereof.

Assays that can be employed for screening a candidate compound for an ability to modulate HIF-1 nitrosylation are known in the art, and include, but are not limited to the "biotin switch" experiment described in Jaffrey & Snyder, 2001, and in EXAMPLE 6.

V. Combination Therapy

The presently disclosed subject matter can be employed as a part of a combination therapy. As used herein, the phrase "combination therapy" refers to any treatment wherein the methods and compositions disclosed herein are used in combination with another therapy including, but not limited to radiation therapy (radiotherapy), chemotherapy, surgical therapy (e.g., resection), and combinations thereof.

V.A. Radiation Treatment

In some embodiments, the methods and compositions disclosed herein are employed in a combination therapy with radiation treatment. For such treatment of a tumor, the tumor is irradiated concurrent with, or subsequent to, administration of a composition as disclosed herein. In some embodiments, the tumor is irradiated daily for 2 weeks to 7 weeks (for a total of 10 treatments to 35 treatments). Alternatively, tumors can be irradiated with brachytherapy utilizing high dose rate or low dose rate brachytherapy internal emitters.

The duration for administration of a composition as disclosed herein comprises in some embodiments a period of several months coincident with radiotherapy, but in some embodiments can extend to a period of 1 year to 3 years as needed to effect tumor control. A composition as disclosed herein can be administered about one hour before each fraction of radiation. Alternatively, a composition can be administered prior to an initial radiation treatment and then at desired intervals during the course of radiation treatment (e.g., weekly, monthly, or as required). An initial administration of a composition (e.g., a sustained release drug carrier) can comprise administering the composition to a tumor during placement of a brachytherapy after-loading device.

Subtherapeutic or therapeutic doses of radiation can be used for treatment of a radiosensitized tumor as disclosed herein. In some embodiments, a subtherapeutic or minimally therapeutic dose (when administered alone) of ionizing radiation is used. For example, the dose of radiation can comprise in some embodiments at least about 2 Gy ionizing radiation, in some embodiments about 2 Gy to about 6 Gy ionizing radiation, and in some embodiments about 2 Gy to about 3 Gy ionizing radiation. When radiosurgery is used, representative doses of radiation include about 10 Gy to about 20 Gy administered as a single dose during radiosurgery or about 7 Gy administered daily for 3 days (about 21 Gy total). When high dose rate brachytherapy is used, a representative radiation dose comprises about 7 Gy daily for 3 days (about 21 Gy total). For low dose rate brachytherapy, radiation doses typically comprise about 12 Gy administered twice over the course of 1 month. $^{125}$I seeds can be implanted into a tumor can be used to deliver very high doses of about 110 Gy to about 140 Gy in a single administration.

Radiation can be localized to a tumor using conformal irradiation, brachytherapy, stereotactic irradiation, or intensity modulated radiation therapy (IMRT). The threshold dose for treatment can thereby be exceeded in the target tissue but avoided in surrounding normal tissues. For treatment of a subject having two or more tumors, local irradiation enables differential drug administration and/or radiotherapy at each of the two or more tumors. Alternatively, whole body irradiation can be used, as permitted by the low doses of radiation required following radiosensitization of the tumor.

Radiation can also comprise administration of internal emitters, for example $^{131}$I for treatment of thyroid cancer, NETASTRON™ and QUADRAGEN® pharmaceutical compositions (Cytogen Corp., Princeton, N.J., United States of America) for treatment of bone metastases, $^{32}$P for treatment of ovarian cancer. Other internal emitters include $^{125}$I, iridium, and cesium. Internal emitters can be encapsulated for administration or can be loaded into a brachytherapy device.

Radiotherapy methods suitable for use in the practice of presently disclosed subject matter can be found in Leibel & Phillips, 1998, among other sources.

V.B. Chemotherapy Treatment

In some embodiments, the methods and compositions disclosed herein are employed in a combination therapy with chemotherapy. Particular chemotherapeutic agents are generally chosen based upon the type of tumor to be treated, and such selection is within the skill of the ordinary oncologist.

Chemotherapeutic agents are generally grouped into several categories including, but not limited to DNA-interactive agents, anti-metabolites, tubulin-interactive agents, hormonal agents, and others such as asparaginase or hydroxyurea. Each of the groups of chemotherapeutic agents can be further divided by type of activity or compound. For a detailed discussion of various chemotherapeutic agents and their methods for administration, see Dorr et al., 1994, herein incorporated by reference in its entirety.

In order to reduce the mass of the tumor and/or stop the growth of the cancer cells, a chemotherapeutic agent should prevent the cells from replicating and/or should interfere with the cell's ability to maintain itself. Exemplary agents that accomplish this are primarily the DNA-interactive agents such as Cisplatin, and tubulin interactive agents.

DNA-interactive agents include, for example, alkylating agents (e.g., Cisplatin, Cyclophosphamide, Altretamine); DNA strand-breakage agents (e.g., Bleomycin); intercalating topoisomerase II inhibitors (e.g., Dactinomycin and Doxorubicin); non-intercalating topoisomerase II inhibitors (e.g., Etoposide and Teniposide); and the DNA minor groove binder Plicamycin.

Generally, alkylating agents form covalent chemical adducts with cellular DNA, RNA, and/or protein molecules, and with smaller amino acids, glutathione, and/or similar biomolecules. These alkylating agents typically react with a nucleophilic atom in a cellular constituent, such as an amino, carboxyl, phosphate, or sulfhydryl group in nucleic acids, proteins, amino acids, or glutathione.

Anti-metabolites interfere with the production of nucleic acids by either of two major mechanisms. Some of the drugs inhibit production of deoxyribonucleoside triphosphates that are the immediate precursors for DNA synthesis, thus inhibiting DNA replication. Some of the compounds are sufficiently like purines or pyrimidines to be able to substitute for them in the anabolic nucleotide pathways. These analogs can then be substituted into the DNA and RNA instead of their normal counterparts.

Hydroxyurea appears to act primarily through inhibition of the enzyme ribonucleotide reductase.

Asparagenase is an enzyme which converts asparagine to nonfunctional aspartic acid and thus blocks protein synthesis in the tumor.

Tubulin interactive agents act by binding to specific sites on tubulin, a protein that polymerizes to form cellular microtubules. Microtubules are critical cell structure units. When the interactive agents bind on the protein, the cell can not form microtubules. Tubulin interactive agents include Vincristine and Vinblastine, both alkaloids and Paclitaxel.

Adrenal corticosteroids are derived from natural adrenal cortisol or hydrocortisone. They are used because of their anti-inflammatory benefits as well as the ability of some to inhibit mitotic divisions and to halt DNA synthesis. These compounds include Prednisone, Dexamethasone, Methylprednisolone, and Prednisolone.

The hormonal agents and leutinizing hormones are not usually used to substantially reduce the tumor mass. However, they can be used in conjunction with the chemotherapeutic agents. Hormonal blocking agents are also useful in the treatment of cancers and tumors. They are used in hormonally susceptible tumors and are usually derived from natural sources. These include, but are not limited to estrogens and conjugated estrogens, progestins, and androgens. Leutinizing hormone releasing hormone agents or gonadotropin-releasing hormone antagonists are used primarily the treatment of prostate cancer. These include leuprolide acetate and goserelin acetate. They prevent the biosynthesis of steroids in the testes. Other anti-hormonal agents include anti-estrogenic agents, anti-androgen agents, and anti-adrenal agents such as Mitotane and Aminoglutethimide.

Representative chemotherapeutic agents are presented in Table 2.

TABLE 2

Chemotherapeutic Agents

| Agent Type | Examples |
| --- | --- |
| Alkylating Agents | |
| Nitrogen mustards | Chlorambucil, Cyclophosphamide, Isofamide, Mechlorethamine, Melphalan, Uracil mustard |
| Aziridines | Thiotepa |
| Methanesulfonate esters | Busulfan |
| Nitroso ureas | Carmustine, Lomustine, Streptozocin |
| Platinum complexes | Cisplatin, Carboplatin |
| Bioreductive alkylators | Mitomycin, Procarbazine |
| DNA strand breaking agents | Bleomycin |
| DNA topoisomerase II inhibitors | Amsacrine, Dactinomycin, Daunorubicin, Doxorubicin, Idarubicin, Mitoxantrone, Etoposide, Teniposide |
| DNA minor groove binder | Plicamycin |
| Anti-metabolites | |
| Folate antagonists | Methotrexate and trimetrexate |
| Pyrimidine antagonists | Fluorouracil, Fluorodeoxyuridine, CB3717, Azacytidine, Cytarabine, Floxuridine |
| Purine antagonists | Mercaptopurine, 6-Thioguanine, Fludarabine, Pentostatin |
| Sugar modified analogs | Cyctrabine, Fludarabine |
| Ribonucleotide reductase inhibitors | Hydroxyurea |
| Tubulin interactive agents | Vincristine, Vinblastine, Paclitaxel |
| Adrenal corticosteroids | Prednisone, Dexamethasone, Methylprednisolone, Prednisolone |
| Hormonal blocking agents | |
| Estrogens and related | Ethinyl Estradiol, Diethylstilbesterol, Chlorotrianisene, Idenestrol |
| Progestins | Hydroxyprogesterone caproate, Medroxyprogesterone, Megestrol |
| Androgens | Testosterone, Testosterone propionate; Fluoxymesterone, Methyltestosterone |

TABLE 2-continued

Chemotherapeutic Agents

| Agent Type | Examples |
| --- | --- |
| Leutinizing hormone releasing hormone agents and/or gonadotropin-releasing hormone antagonists | Leuprolide acetate; Goserelin acetate |
| Anti-estrogenic agents | Tamoxifen |
| Anti-androgen agents | Flutamide |
| Anti-adrenal agents | Mitotane, Aminoglutethimide |

A "potentiator" can be any material that improves or increases the efficacy of a pharmaceutical composition and/or acts on the immune system. Exemplary potentiators are triprolidine and its cis-isomer, which can be used in combination with chemotherapeutic agents. Triprolidine is described in U.S. Pat. No. 5,114,951. Other potentiators are procodazole 1H-Benzimidazole-2-propanoic acid; [β-(2-benzimidazole) propionic acid; 2-(2-carboxyethyl)benzimidazole; propazol) Procodazole is a non-specific active immunoprotective agent against viral and bacterial infections and can be used with the compositions disclosed herein. Potentiators can improve the efficacy of the disclosed compositions and can be used in a safe and effective amount.

Antioxidant vitamins such as ascorbic acid, beta-carotene, vitamin A, and vitamin E can also be administered with the compositions disclosed herein.

EXAMPLES

The following Examples have been included to illustrate modes of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

Materials and Methods used in the Examples

Cell lines and tissue culture. The 4T1 murine mammary adenocarcinoma cell line and B16F10 murine melanoma cells were obtained from the American Type Culture Collection (ATCC, Manassas, Va., United States of America). The two cell lines were cultured in Dulbeccos's modified Eagle's medium (DMEM) supplemented with 10% fetal bovine serum.

Reagents. $CoCl_2$, S-nitrosoglutathione (GSNO), potassium 2-(4-carboxyphenyl)-4,4,5,5-tetramethylimidazoline-1-oxyl-3-oxide (carboxy-PTIO)., and carrageenan were purchased from Sigma (St. Louis, Mo., United States of America). The proteasome inhibitor MG-132 was purchased from EMD Biosciences, Inc. (San Diego, Calif., United States of America). Luciferin was obtained from Xenogen (Alameda, Calif., United States of America). Nω-nitro-L-arginine methyl ester (L-NAME) and 1400W were purchased from Cayman Chemical (Ann Arbor, Mich., United States of America). N-(6-[biotinamido]hexyl)-3'-(2'-pyridyldithio)-propionamide (biotin-HPDP) was purchased from Pierce Biotechnology (Rockford, Ill., United States of America).

Plasmids and cloning procedures. The HIF-1α bioluminescence reporter (ODD-luc) construct was created by fusing PCR product of ODD domain of HIF-1α (GENBANK® Accession No. U59496) to the 5' end of firefly luciferase reporter gene. Along with this construct, a luciferase expression vector in which luciferase gene was driven by the CMV promoter was used as a control. A C533S ODD mutation was achieved by in vitro site-directed mutagenesis. ODD fragments with or without the mutation were cloned into pCMV-3Tag-4B Epitope Tagging Mammalian Expression vector (Stratagene, La Jolla, Calif., United States of America). The full length mouse VHL gene (GENBANK® Accession No. S76748) was cloned form mouse tissue and tagged with HA tag by PCR. All constructs were sequence-verified.

siRNA. siRNA sequences targeted to the VHL gene were designed by using an Internet-based program available at the website of Ambion Inc. (Austin, Tex., United States of America). A retroviral siRNA expression vector (pSilencer 5.1-U6 Retro from Ambion Inc.) was used to stably introduce the following siRNA sequence targeted to VHL gene to 4T1 cells: AACATCACATTGCCAGTGTAT (SEQ ID NO: 17). pSilencer 5.1-U6 Scrambled siRNA (Ambion Inc.) was used as a negative control.

Imaging luciferase activity. Luciferase expression/activity was detected and quantified as relative light units (RLUs) by using the Xenogen IVIS™ imaging system and associated LIVING IMAGE® software (Xenogen, Alameda, Calif., United States of America). For in vitro observations, cells transfected with luciferase reporter gene constructs were grown in 12-well or 24-well cell culture plates. After cells reached 80% confluence, they were treated with the different chemicals or were cultured in the hypoxic chamber (Sheldon Manufacturing, Inc., Cornelius, Oreg., United States of America). At the times indicated, luciferin (150 μg/ml) was added and the plates were imaged for luciferase expression. For in vivo experiments, treated tumor-bearing mice received an i.p. injection of luciferin (150 mg/kg) during isofluorane anesthesia. Repeated images of luciferase expression/activity were acquired following manufacturer's specified procedures.

Animal experiments. Female NIH Swiss nude mice, C57BL/6 mice were purchased from the National Cancer Institute (NCI; Fredrick, Md., United States of America). Mice with a genetic disruption of the inducible nitric acid synthase gene (C57BL/6 iNOS$^{-/-}$) were obtained from the Jackson Laboratory (Bar Harbor, Me., United States of America). Female BALB/c mice were obtained from Charles River Laboratories (Raleigh, N.C., United States of America). Animals were maintained and cared for in accordance with the Duke University Institutional Animal Care and Use Committee guidelines. For tumor implantation, 4T1 tumors were grown in nude mice or in syngeneic BALB/c mice, and B16F10 melanoma in syngeneic C57BL/6 or iNOS$^{-/-}$ mice. About $5\times10^5$ wild type- or luciferase reporter gene-transfected tumor cells were injected subcutaneously (s.c.) into mice in 50 μl of PBS solution in the hind legs of ketamine/xylazine-anesthetized mice. When the tumors reached 6-8 mm in diameter, mice were randomly assigned to experimental groups. To image the luciferase activity, single dose of 6 Gy X-ray was given to the tumor on the right leg and this day was set as day 0. The luciferase activity was imaged everyday or every other day for ten days. For the tumor growth delay assay, radiotherapy was employed in its clinical mode: tumors were treated with 3 fractions of 6 Gy every other day from day 0. Tumor growth was then followed by use of a caliper every 2 days. Tumor volume was calculated using the following formula: volume=(length×width$^2$)/2. Where indicated, mice received the Pan-NOS inhibitor L-NAME (500 mg/L) or the iNOS-selective inhibitor 1400W (50 mg/L) in the drinking water one day before X-ray treatment. Drinking water was renewed daily until animal sacrifice.

ELISA and western blot analysis. Tumor homogenates and tissue culture samples were both used for protein analysis. All results were normalized for total sample protein contents, determined by using a Bradford-based assay (BIO-RAD, Hercules, Calif., United States of America). Nuclear extracts were prepared by use of the NUCBUSTER™ Protein Extraction Kit (Novagen, San Diego, Calif., United States of America). HIF-1 binding activities in tumor homogenates were quantified with the TRANSAM™ HIF-1 ELISA Kit (Active Motif, Carlsbad, Calif., United States of America) with the use of an antibody against mouse HIF-1α (Novus Biologicals, Liftleton, Colo., United States of America). VEGF levels were assayed using the mouse VEGF quantikine ELISA Kit (R&D systems, Minneapolis, Minn., United States of America). HIF-1α levels in tissue culture samples were determined by Western Blot using a polyclonal rabbit anti-HIF-1 antibody (Novus Biologicals) detected with horseradish peroxidase (HRP)-conjugated donkey anti-rabbit secondary antibody (Santa Cruz Biotechnology, Santa Cruz, Calif., United States of America).

Macrophage depletion experiments. Macrophage depletion was achieved in mice as described in Muller et al., 2005. Briefly, nude mice received repeated i.p. injections of 2 mg carrageenan at 6, 3, and 1 day before s.c. injection of 4T1 tumor cells, after which mice were injected once per week until the end of the experiment.

Immunohistochemical stainings. Immunofluorescence stainings were performed on tumors biopsied 5 days after irradiation (6 Gy). Cryoslices were fixed in 4% paraformaldehyde. Endogenous peroxidases were quenched with 3% $H_2O_2$. slices were then blocked with 10% normal serum, probed with a primary antibody, and revealed with a secondary antibody coupled to FITC (to reveal CD68 and HIF-1α) or to TRITC (for iNOS detection; Jackson ImmunoResearch Labs, Inc., West Grove, Pa., United States of America). Primary antibodies were: polyclonal rat anti-CD68 to label macrophages (BD PHARMINGEN™, San Jose, Calif., United States of America), polyclonal goat anti-iNOS (Santa Cruz Biotechnology), and polyclonal rabbit anti-HIF-1α (Novus Biologicals). Cryoslices were examined with a Zeiss Axioskop microscope equipped for fluorescence. Digitized pictures were overlaid by using the METAMORPH™ software from Molecular Devices Corp. (Sunnyvale, Calif., United States of America).

Vessel staining was performed on tumor cryoslices by using the VECTASTAIN® ABC and the NOVARED™ kits from Vector Laboratories (Burlingame, Calif., United States of America), according to the manufacturer's protocol. The primary anti-CD31 antibody (Santa Cruz Biotechnology, Santa Cruz, Calif.) was labeled with a secondary biotinylated anti-rabbit antibody (Jackson ImmunoResearch Labs, Inc.). Slices were counterstained using Harris' hematoxilin. Vascular density was determined by counting CD31-positive structures in 5 random fields per tumor.

In vitro interaction assay for ODD and VHL Protein. 4T1 cells grown in 35 mm dishes were transfected with 3 µg of pCMV-ODD-3Myc, including c-myc-tagged wild type ODD and its mutant version, or 3 µg of pCMV-HAVHL encoding HA-tagged full-length VHL by using lipofectamine 2000 (Invitrogen, Carlsbad, Calif., United States of America). 24 hours later, cells were subjected to 1 mM GSNO for 8 hours. Cells were then scraped off the dishes and collected. To each cell pellet 300 µl lysis buffer (50 mM Tris, 150 mM NaCl, 0.5 µM ferrous chloride, 0.5% NP-40, 0.5 µM MG-132, protease inhibitor cocktail, pH 7.5) was added. After centrifugation (15,000×g for 30 min), supernatants were transferred to fresh tubes and the input ODD and VHL were detected by Western Blot analysis using antibodies against C-myc tag or HA tag (Novus Biologicals). 0.5 mg of supernatant from ODD-c-myc or C533S-ODD-cmyc-expressing cells were mixed with 0.25 mg of the supernatant from HA-VHL expressing cells and incubated at 4° C. for 2 hours. The co-immunoprecipitation was achieved by the addition of 20 µl of anti-HA antibody (agarose immobilized; Novus Biologicals). Beads were collected, washed three times with 1 ml washing buffer(20 mM Tris, 100 mM NaCl, 1 mM EDTA, 0.5% NP-40), supplemented with 50 µl 2× SDS-PAGE sample buffer, and boiled at 95° C. for 10 minutes. Beads were removed by centrifugation, and supernatants were loaded on 12% SDS-gels. The amount of ODD-c-myc or C533S-ODD-c-myc that had been pulled down with HA-VHL was probed with a primary anti-c-myc antibody (Novus Biologicals), and revealed with an anti-goat secondary antibody (Santa Cruz Biotechnology). After membrane stripping (RESTORE™ Western Blot Stripping Buffer, Pierce Biotechnology), immunoprecipitated HA-VHL was labeled with a primary antibody against HA (Novus Biologicals), and revealed with a secondary anti-goat antibody (Santa Cruz Biotechnology).

Biotin switch assay. Biotin switch assay was performed as described (Jaffrey & Snyder, 2001). Briefly, 4T1 cells were transfected with pCMV-ODD-3Myc. 24 hours later, cells were treated with 1 mM GSNO for 8 h. Cells were then homogenized by 26G needle in HEN buffer (250 mM HEPES-NaOH pH 7.7, 1 mM EDTA, 0.1 mM Neocuproine), and then centrifuged at 1000×g for 10 minutes at 4° C. Supernatant (300 µg) was added to 4 volumes of blocking buffer (9 volumes of HEN buffer plus 1 vol 25% SDS, 20 mM MMTS) at 50° C. for 20 minutes with frequent vortexing. The MMTS was then removed by desalting three times with the BIO-SPIN® 6 column (Bio-Rad, Hercules, Calif., United States of America) pre-equilibrated in HEN buffer. To the eluate was added biotin-HPDP (final concentration of 2 mM) prepared fresh as a 4 mM stock in DMSO from a 50 mM stock suspension in DMF. Sodium ascorbate was added to a final concentration of 1 mM. After incubation for 1 hour at 25° C., biotinylated proteins were precipitated by streptavidin-agarose beads (Pierce Biotechnology, Rockford, Illinois, United States of America). The streptavidin-agarose beads were then pelleted and washed 5 times with HENS buffer. The biotinylated proteins were eluted by SDS-PAGE sample buffer and subjected to Western blot analysis. The biotinylated ODD was detected by use of an antibody against the c-myc tag.

Statistics. Student's t test, one-way and two-way ANOVA were used where indicated. In growth delay experiments, the numbers of days for tumors to reach 5× their initial volume were used for comparing different treatment groups. P<0.05 was considered to be statistically significant.

Example 1

A Novel Reporter for Non-Invasive, In Vivo Observation of HIF-1 Activity

HIF-1 activity is difficult to study in vivo because of the very short half-life of the HIF-1α subunit (Yu et al., 1998). A strategy was adopted in which the oxygen-dependent degradation (ODD) domain of the protein was fused with the firefly luciferase gene (luc; see FIG. 1A). This approach took advantage of the fact that the stability of the HIF-1α subunit (and hence the activity of HIF-1) is mainly regulated by the ODD. It has been shown that the modification of key proline residues by proline hydroxylases (PHDs) under normoxic conditions render the HIF-1α susceptible to binding by VHL and subsequent degradation by the proteasome system.

Figure 1B:
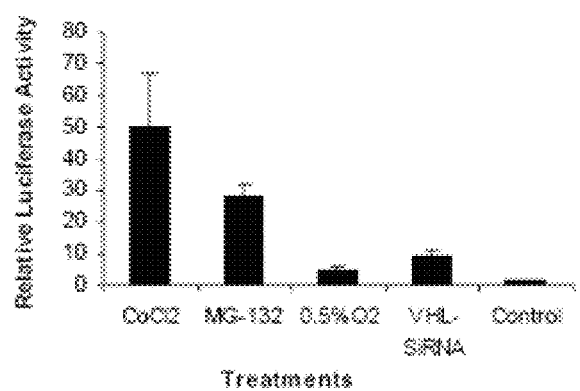

Thus, it was reasoned that the fusion protein would recapitulate the regulation of HIF-1α and serve as noninvasive reporter of HIF-1α activity. When introduced into several tumor cell lines and evaluated under various treatment conditions, the reporter fulfilled expectations. While background luminescence arising from reporter gene expression was very low, it rose significantly after cellular exposure to hypoxia, $CoCl_2$ (an established inhibitor of HIF-1α degradation), or MG132 (a proteasome inhibitor), closely mimicking the known regulation of HIF-1α (see FIG. 1B).

Figure 1C:
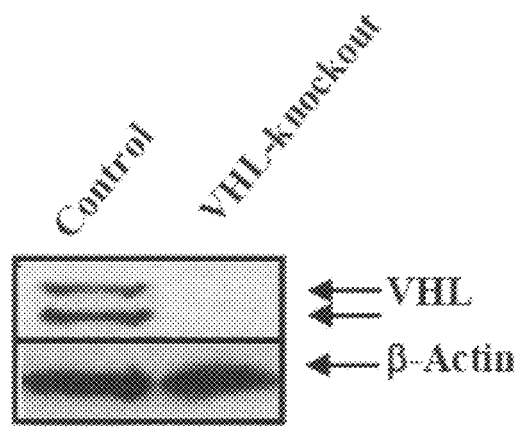
Figure 1D:
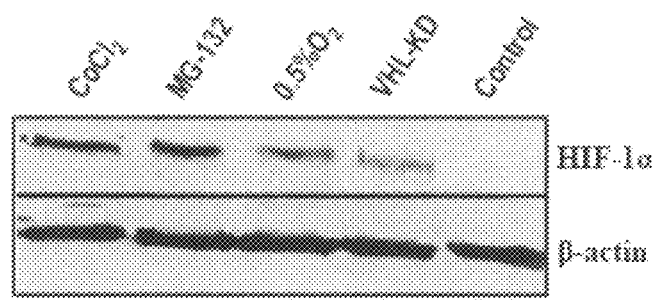

The successful recapitulation of HIF-1α stability regulation was further confirmed by transfecting the reporter cells With a VHL-targeted siRNA. The siRNA effectively reduced the level of the VHL expression (see FIG. 1C), which led to significant increases in ODD-luc level, consistent with the role of VHL as the main mediator of HIF-1α ubiquitylation and degradation. Western blot analysis showed a parallel increase in endogenous HIF-1α level after various treatment conditions (FIG. 1D), further validating the ODD-luc reporter as a surrogate marker for HIF-1α.

Discussion of Example 1

The ODD-luc reporter had a much better dynamic range for the detection of HIF-1α levels than previous promoter-based approaches. In previous studies dealing with the radiation-induced HIF-1α activation (Moeller et al., 2004; Moeller et al., 2005), the in vivo data were mostly obtained with a GFP reporter containing an artificial hypoxia-responsive promoter (HRP). As GFP is a very stable protein (with half life exceeding 24 hours) and the artificial HRP promoter is subject to HIF-independent biological influences that lead to high background activity, the sensitivity of the HRP-GFP reporter was very limited, with a dynamic range limited to 1-3 fold over background level. In addition, HIF-GFP-based experiments had to be carried out with invasive tumor models such as the dorsal skinfold window chamber tumors (Huang et al., 1999) to obtain quantitative data or to conduct repeated measurements. With the new reporter, any murine tumor system can be monitored with the dynamic range of the reporter increased from 1 to 100 fold over background, and repeated measurements acquired non-invasively by means of in vivo optical imaging such as the Xenogen IVIS™ imaging system (Contag et al., 1998; Zhang et al., 2004a).

Example 2

Radiation-induced HIF-1α Stabilization in Tumors

In order to observe HIF-1α regulation after treatment response, 4T1 murine breast tumor cells stably transduced with the ODD-luc reporter gene were implanted subcutaneously into mice. After the tumors reach 6-8 mm in diameter, they were irradiated and followed for ODD-luc expression using the Xenogen IVIS™ system. From day 3 after irradiation, the level of HIF-1α, as determined by ODD-luc, appeared to increase linearly over 3 days. It peaked at around 6 days and fall back to background levels after day 10 (see FIG. 2A). The differences between the irradiated and sham-irradiated groups were highly significant from day 3 ($p<0.01$).

Radiation-induced stabilization of ODD-luc was accompanied by increases in HIF-1 promoter binding activities to the corresponding HRE binding element (see FIG. 2B) and upregulation of a downstream target gene, vascular endothelial growth factor (VEGF; see FIG. 2C). Similar results were obtained with two other tumor models, B16.F10 melanoma model and the CT26 colon cancer model. These results indicated that radiation induced a persistently increasing level of HIF-1α expression and activity. While radiation has been shown to activate HIF-1α in previous studies (Moeller et al., 2004), the pattern of in vivo induction such as the one disclosed herein had never been observed previously.

Example 3

Role of Nitric Oxide in Mediating Radiation-Induced HIF-1α Activation

The cause of radiation-induced HIF-1α stabilization is not understood. One possibility is that radiation creates a more hypoxic condition in the tumor microenvironment than pre-treatment, which causes the stabilization of HIF-1α through the prolyl hydroxylase (PHD) pathway. However, this is highly unlikely. Previous studies have indicated no significant changes (Brizel et al., 1999; Brizel et al., 1996) in the level of hypoxia in tumor following radiation. Indeed, it had been shown that tumor oxygen tension actually increases after irradiation due to a reduced cell proliferation and tumor cell death. Measurements of 4T1 tumors after irradiation indicated a similar scenario (Moeller et al., 2004).

The co-inventors' previous studies had indicated that radiation induced free radicals are at least partially involved in the activation of so-called "stress granules" (Moeller et al., 2004). However, the identity of the free radicals involved in that response is not clear.

Figure 3A:
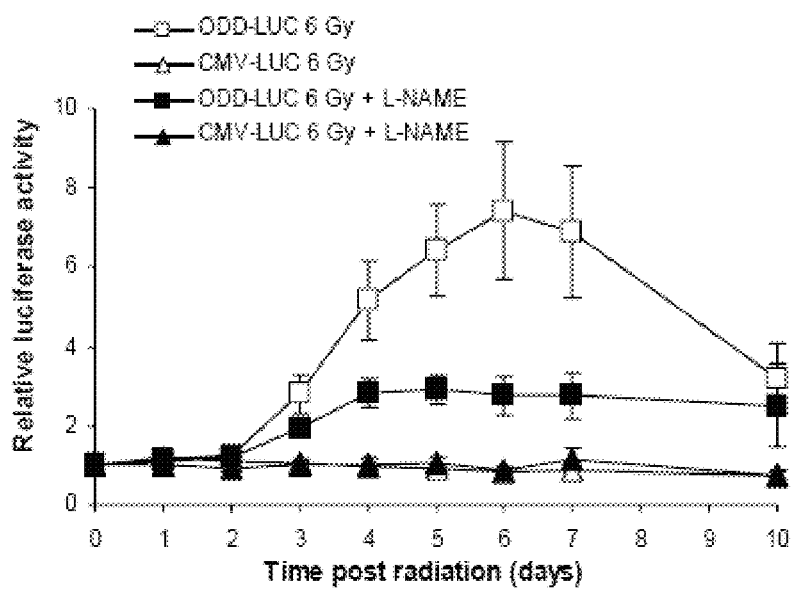
FIGS. 3A-3D depict the results of experiments showing that nitric oxide is a key regulator of radiation-induced HIF-1α activation.

After evaluation with various agents, nitric oxide (NO) was determined to be the main free radical species that was responsible for radiation-induced HIF-1α activation (see FIG. 3A). The administration of L-NAME, a potent non-specific inhibitor of nitric oxide synthases (NOS), to mice effectively attenuated radiation-induced HIF-1α stabilization in tumors, as shown by the loss of ODD-luc signal. As NOS are the major source of NO in vivo, the presently disclosed results indicated that NO played a pivotal role in radiation-induced HIF-1α stabilization. Control experiments indicated that NO produced by NOS did not influence the activity of constitutively expressed luciferase activity, confirming the role of NO in regulating ODD (and hence HIF-1α) stability (see FIG. 3A).

Figure 3B:
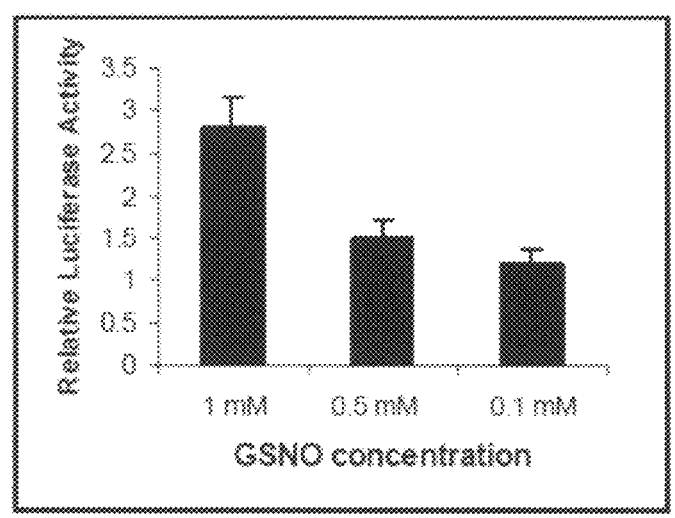
Figure 3C:
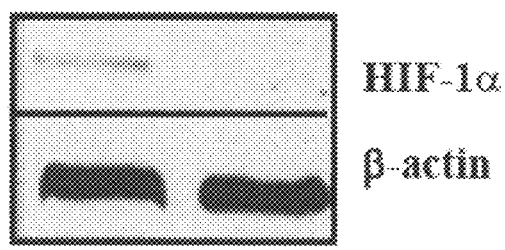
Figure 3D:
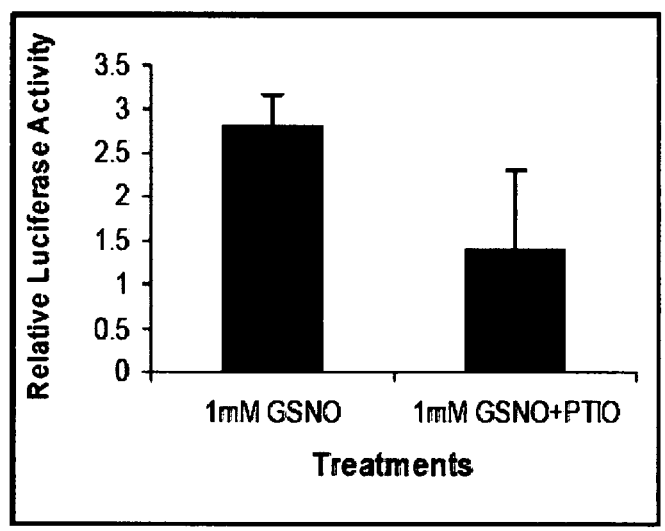

The role of NO was further confirmed in cell culture assays. Treatment of 4T1-ODD-luc cells with the NO donor S-nitrosoglutathione (GSNO) effectively induced dose-dependent HIF-1α activation, similar to treatment with ionizing radiation (see FIG. 3B). Western blot analysis of the GSNO treated cells clearly indicated endogenous HIF-1α induction (FIG. 3C. A NO scavenger, carboxy-PTIO(4-carboxyphenyl-4,4,5,5-tetramethylimidazoline-3-oxide-1-oxyl), effectively suppressed HIF-1α activation by GSNO (FIG. 3D), demonstrating that NO is directly responsible for the observed ODD-luc accumulation.

Example 4

Inducible Nitric Oxide Synthase as a Major Source of NO in Radiation-Induced HIF-1α Activation The source of the NO that stimulates HIF in irradiated tumors in vivo was investigated. Of the three NOS isoforms, inducible NO synthase (iNOS), is the most likely candidate because, unlike neuronal and endothelial NOS, which are constitutively activated in healthy tissues, it is exclusively expressed and activated in pathological tissues such as tumors, where it can produce high micromolar levels of NO.

Moreover, tumors usually contains significant number of macrophages (Colombo & Mantovani, 2005; Lewis & Murdoch, 2005), which express/activate their iNOS as part of their immunoeffector activity and thus provide a ready source of NO upon activation.

Figure 4:
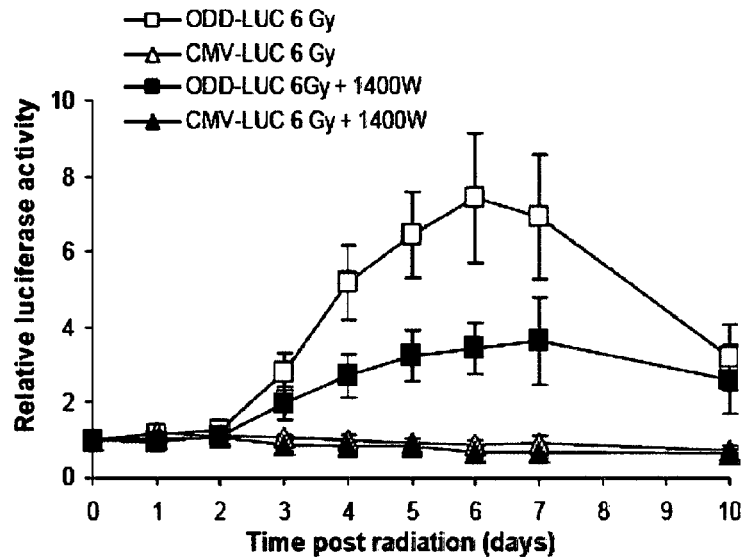
FIGS. 4A and 4B are graphical representations demonstrating the role of the inducible form of nitric oxide synthase (iNOS) in radiation-induced HIF-1α activation.
Figure 4:
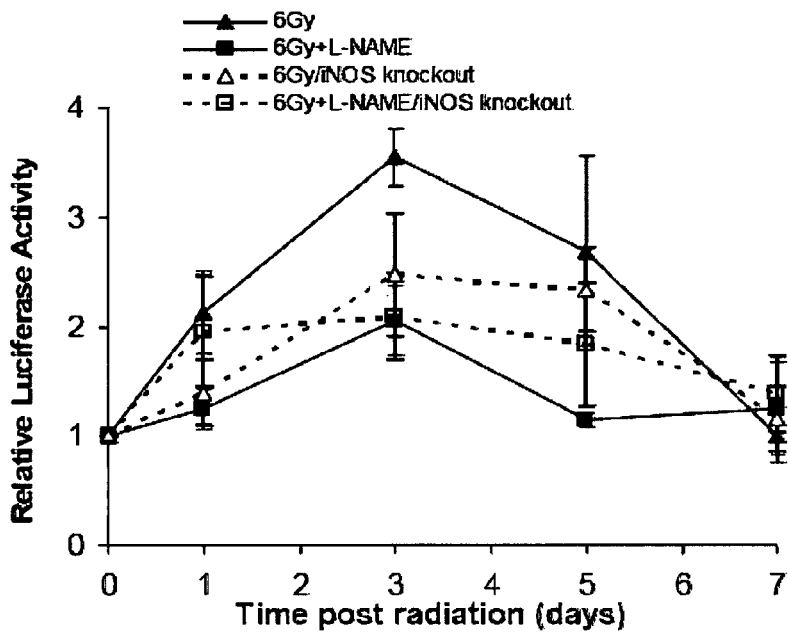

To pinpoint the source of NO, two series of experiments were performed. In the first series of experiments, the iNOS-specific inhibitor, 1400W (Alderton et al., 2001; Thomsen et al., 1997), was used to examine radiation-induced HIF-1α induction in ODD-luc-transduced 4T1 tumors. The results indicated that 1400W attenuated radiation-induced ODD-luc in 4T1 as potently as the general NOS inhibitor L-NAME (see FIG. 4A). This observation indicated that iNOS is the main mediator of radiation-induced HIF-1α stabilization.

In the second series of experiments, C57BL/6 mice with targeted disruption of the iNOS gene (iNOS$^{-/-}$) were implanted with syngeneic B16F10 melanoma cells stably transduced with ODD-luc gene. The tumors were then irradiated and observed for HIF-1α activation. A significant attenuation of radiation-induced ODD-luc induction in the tumors grown in iNOS$^{-/-}$ mice compared to wild-type controls was observed. In fact, ODD-luc suppression in iNOS$^{-/-}$ animals and in wild type mice treated with L-NAME were of similar amplitude (see FIG. 4B), indicating that L-NAME-suppressed HIF-1α activation in the wild type mice was attributable to the inhibition of iNOS.

Example 5

Macrophages are a Major Source of iNOS and NO in Radiation-Induced HIF-1α Activation Previous studies have indicated that macrophages are a rich source of NO and that the tumor microenvironment is abundantly populated with macrophages. In light of this information and together with the results presented hereinabove, it was hypothesized that tumor-associated macrophages might play a significant role in radiation-induced HIF-1α induction. This would also be consistent with previous findings that tumor-associated macrophages play important roles in regulating tumor angiogenesis, at least partially through NO release (Leek et al., 2000; Leek et al., 2002; Varney et al, 2002).

Figure 5A:
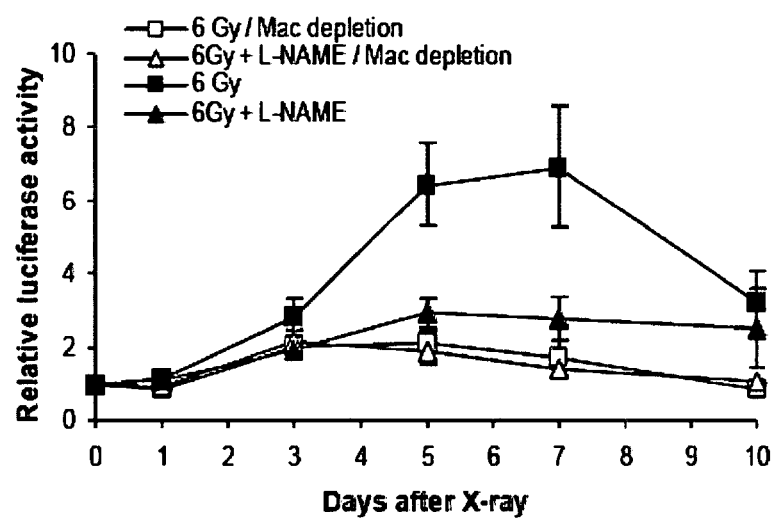
FIGS. 5A and 5B depict the role of macrophages in radiation-induced HIF-1α activation.

In order to investigate the potential involvement of macrophages in HIF-1α activation, radiation-induced ODD-luc activation in mice that had been chemically depleted of macrophages through the use of carrageenan was measured (Goldmann et al., 2004; Muller et al., 2005; Udono et al., 1994). The results were very similar to those obtained in iNOS$^{-/-}$ mice (see FIG. 4). A significant reduction in radiation-induced ODD-luc activation and the loss of L-NAME inhibition of the activation in tumors in mice with macrophage depletion was observed (FIG. 5A).

Figure 5B:
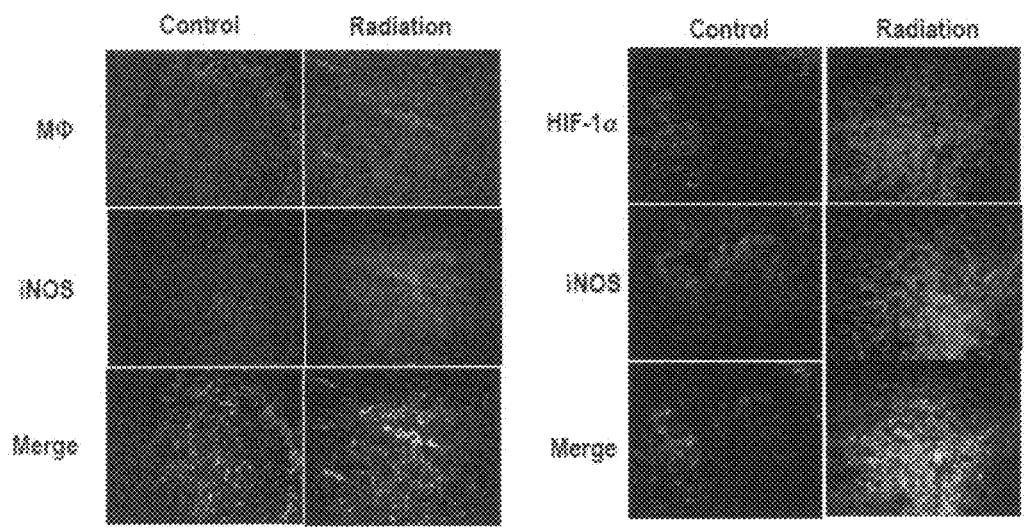

These results clearly established that iNOS in tumor-associated macrophages was the main source for the NO that was involved in radiation-induced HIF-1α activation. Immunohistochemistry analysis further confirmed that irradiation of the tumor increased the number of tumor-associated macrophages and activated the iNOS gene in these macrophages (see FIG. 5B, left panel). The results presented herein also confirmed that activated iNOS gene expression was accompanied by concomitant HIF-1α activation in tumors (FIG. 5B, right panel).

Example 6

The Molecular Mechanism of HIF-1α Activation by NO

The aforementioned experiments provided strong evidence that NO generated by tumor-associated macrophages played critical roles in radiation-induced HIF-1α activation. However, the exact molecular mechanism of how NO induces stabilization of HIF-1α remained unclear.

In theory, there are at least two ways NO can influence HIF-1α: the inactivation of upstream prolyl hydroxylases and/or the direct modification of the ODD domain. Others have shown that NO can inhibit the activity of the prolyl hydroxylases (PHDs), which can result in the stabilization of HIF-1α (Metzen et al., 2003). However, inhibition of PHDs did not appear to account for all the NO-induced HIF-1α activation. It was therefore reasoned that a direct modification of the ODD domain could also participate in HIF-1 activation.

A previous report suggested that, although all 13 cysteine residues in the purified HIF-1α protein are susceptible to nitrosylation in test tubes, only 3-4 can be nitrosylated in cells in cultured cells (Sumbayev et al., 2003). However, the biological significance of these nitrosylations on HIF-1α stability has not been identified.

Thus, NO might stabilize the HIF-1α through S-nitrosylation of ODD domain during radiotherapy. To test this hypothesis, a mutant (C533S) involving the only Cys residue in the murine HIF-1α ODD domain, Cys533, was generated. This residue corresponds to Cys520 (which also is the only Cys the human ODD domain) in human HIF-1α and is conserved among a wide spectrum of vertebrate species that included human, mouse, rat, frog, etc. (see FIG. 6A). The replacement of the cysteine by a serine was chosen because the only difference between these amino acids is that the thiol (—SH) group of cysteine is replaced by the hydroxyl (—OH) group of serine, thereby preventing S-nitrosylation. The likelihood that the point mutation will alter the 3-D structure of ODD is thus minimal. The C533S ODD domain was then fused with the luciferase reporter gene, transfected into 4T1 tumor cells, and examined for its activation in comparison with wild type ODD-luc in vitro and in vivo.

Figure 6:
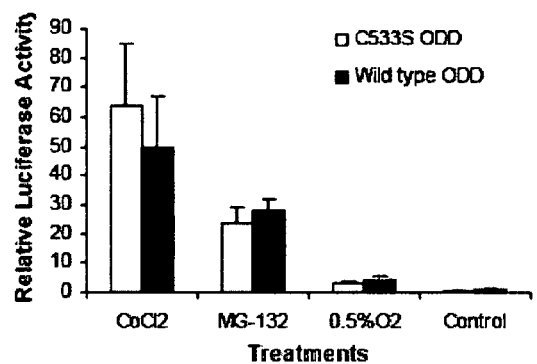
FIGS. 6A-6F depict normoxic prevention of HIF-1α degradation though S-nitrosylation of cysteine 533.
Figure 6:
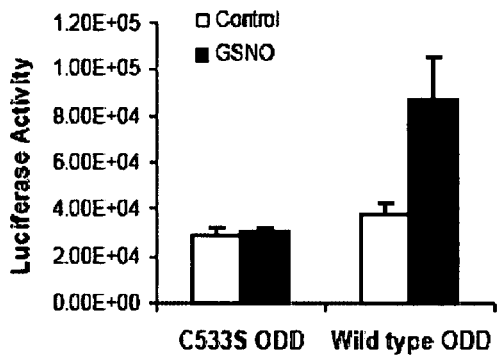
Figure 6:
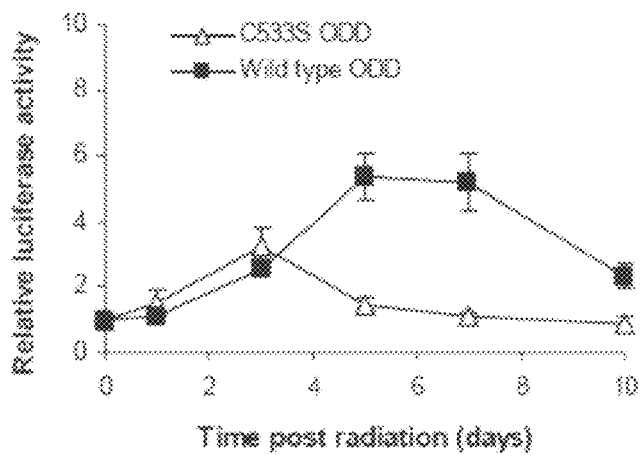
Figure 6:
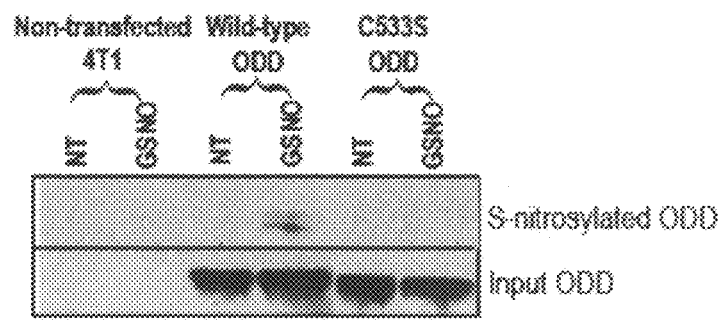
Figure 6:
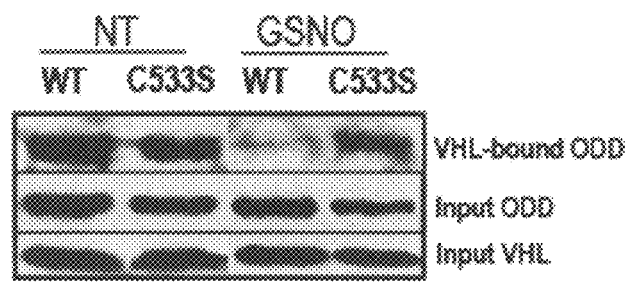

In vitro, the background expression level of mutant C533S-ODD-luc was very low, similar to wild type (see FIG. 6B). However, when C533S-ODD-luc was subjected to hypoxia, proteasome inhibition, or CoCl$_2$ exposure, significant inductions, similar to wild-type, were observed (see FIG. 6B), indicating that the mutation did not cause any gross structural perturbation that would disrupt normal processing by upstream PHDs and downstream VHL and proteasome.

However, when the mutant C533S-ODD-luc transduced cells were exposed to the NO donor GSNO, induced ODD-luc expression was almost absent, in sharp contrast to wild type ODD-luc transduced cells, which had significant GSNO induction (see FIG. 6C).

In vivo, background levels of mutant C533S-ODD-luc transduced tumors were similar to what was observed in wild type ODD-luc transduced tumors (see FIG. 6D). However, the C533S mutation significantly attenuated radiation-induced ODD-luc activation in vivo (see FIG. 6D, days 5, 7, and 10), indicating that S-nitrosylation of the Cys533 residue in the HIF-1α protein played a critical role in regulating the stabilization of HIF-1α after radiation therapy.

The direct proof for S-nitrosylation of HIF-1α at C533 came from "biotin switch" experiments (Jaffrey & Snyder, 2001) in which direct chemical evidence for the nitrosylation of the ODD domain was sought. In the absence of GSNO treatment, neither wild type ODD nor C533S-ODD was S-nitrosylated (see FIG. 6E). S-nitrosylation was clearly observed in wild type ODD upon GSNO treatment, but completely absent in C533S-ODD after GSNO treatment (see FIG. 6E), demonstrating that C533 was S-nitrosylated in the cellular environment with a sufficient amount of NO.

The site-directed mutagenesis experiments disclosed herein further suggested that nitrosylation at Cys533 rendered the HIF-1α protein resistant to degradation by preventing the binding of HIF-1α by VHL. To examine this possibility, the effects of NO and of C533S on the binding of ODD with VHL in ODD-transfected tumor cells were tested. Co-immunoprecipitation results revealed that the strong binding of wild-type ODD with VHL in the absence of NO was completely abolished in cells exposed to GSNO (see FIG. 6F). Strikingly, this regulation was completely lost in cells expressing C533S-ODD, which is consistent with the continuous degradation of the mutated ODD in the presence of NO (FIG. 6C and 6D). Taken together, the in vivo and in vitro results. (see FIG. 6A-F) provided compelling evidence that NO-mediated stabilization of HIF-1α is largely mediated by S-nitrosylation of the Cys533 in the ODD domain.

Example 7

Figure 7:
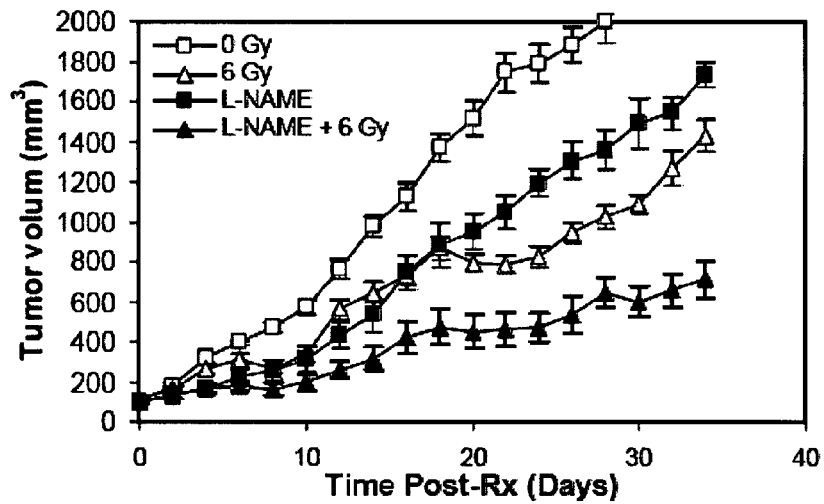
FIGS. 7A-7C depict the enhanced anti-tumor efficacy of radiotherapy in combination with L-NAME. B16F10 and 4T1 tumors were established in syngeneic C57BL/6 and 4T1 mice, respectively and irradiated with 3 fractions of X-rays at 6 Gy/fraction (irradiation every other day). In some of the groups, L-NAME was administered in the drinking water one day before irradiation. Tumor sizes were monitored every other day. At least 6 animals were used in each treatment groups. Tumor sizes were then plotted against time for each tumor type. The error bars represent the standard errors of the mean.
Figure 7:
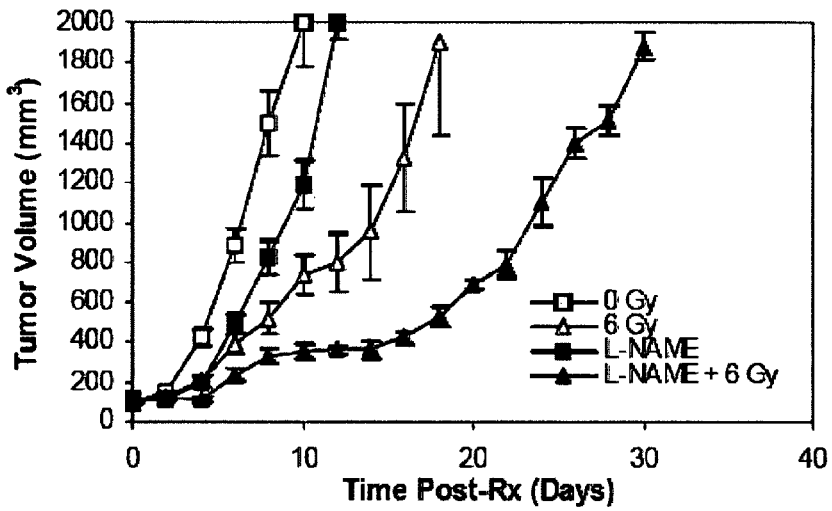
Figure 7:
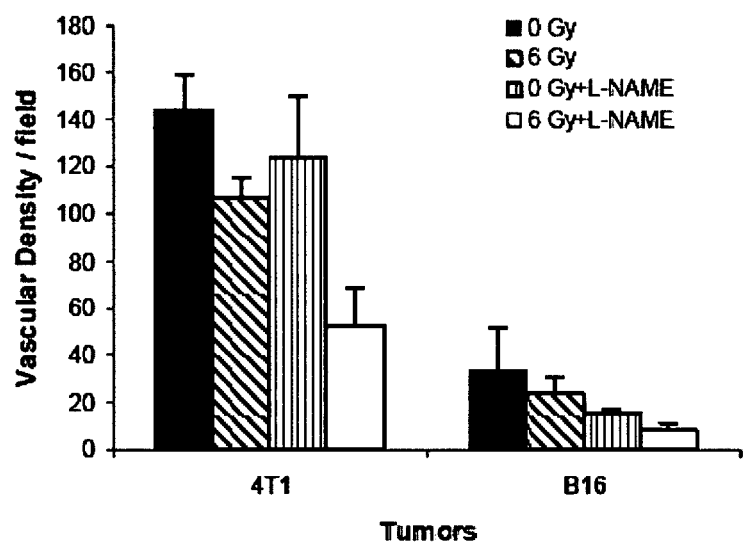

The Functional Importance of NO-Mediated HIF-1α Activation During Cancer Therapy As HIF-1α has been shown to be a key tumor survival factor during cancer therapy, it was postulated that the inhibition of HIF-1α activation through the prevention of NO production would have anti-tumor efficacy. To examine this hypothesis, tumor growth delay experiments with co-administration of radiotherapy (3{6 Gy) and L-NAME were performed in two aggressive tumor models: 4T1 (murine mammary adenocarcinoma; see FIG. 7A) and B16F10 (murine melanoma; see FIG. 7B). In both models, the inhibition of NO production by L-NAME significantly enhanced the therapeutic efficacy of radiotherapy. In addition, the use of L-NAME in conjunction with radiotherapy significantly reduced tumor vasculature (see FIG. 7C).

These results suggested that NO-mediated HIF-1α activation indeed played a critical role in overall tumor response to radiotherapy, consistent with previous reports that the survival of tumor vasculature is key to tumor survival during radiotherapy (Garcia-Barros et al., 2003; Moeller et al., 2004). They further suggested that NOS inhibitors can be used as therapeutic agents to enhance the efficacy of conventional cancer treatments.

Discussion of Examples 1-7

Understanding HIF-1 regulation during cancer treatment can provide insights into how tumor responds to therapy. This is because HIF-1 has been shown to be a key tumor survival factor after cancer therapy(Moeller et al., 2004; Zhang et al., 2004b). The presently disclosed discovery of HIF-1α upregulation through NO generated from tumor-associated macrophages is important for at least two reasons: recognizing the tumor-associated macrophages (TAMs) as a major regulator of HIF-1 and the identification of S-nitrosylation of C533 (human equivalent C520) as a key mechanism for NO-mediated HIF-1α stabilization. The present disclosure establishes for the first time that TAM is a pivotal mediator of tumor angiogenic activity after radiotherapy while the latter unveils a novel mechanism for HIF-1α regulation.

Previous studies have suggested that NO effects on HIF-1α to be different under hypoxic or normoxic conditions. Under hypoxic conditions, it was shown that the presence of NO can inhibit HIF-1 activity (Sogawa et al., 1998) by inducing the redistribution of intracellular oxygen (Hagen et al., 2003) that increased PHD activity and HIF-1α degradation.

Under normoxic conditions, however, NO has been shown to increase the stability and activity of HIF-1α in at least two different ways. First, NO can directly inhibit the activity of PHDs (Metzen et al., 2003) and thereby inhibiting proteasome-mediated degradation of HIF-1α. Second, NO can enhance the transcriptional activity of HIF-1 through the nitrosylation of Cys800 (Yasinska & Sumbayev, 2003), which enhances the binding of the HIF-1α C-terminal trans-activation domain (C-TAD) to p300.

The presently disclosed discovery that NO can regulate HIF-1α stability through S nitrosylation of Cys533 provides a third avenue for NO-mediated increase in HIF-1 transcriptional activity. It also provides a remarkable example where targeted S-nitrosyaltion of a single cysteine residue in a protein can significantly influence its interaction with other protein(s), very similar to a recent report (Kim et al., 2005) on nitric oxide regulation of the COX-2 gene activation.

Of special interest is the fact that HIF-1 has also been known to enhance iNOS gene expression in a variety of cell types (Jung et al., 2000; Matrone et al., 2004; Melillo et al.,1997). Therefore, it is possible that activated iNOS and HIF-1 forms an amplification loop during wound healing or inflammation. Inconsistent with this hypothesis is a recent report that indicate HIF-1 and iNOS do appear to regulate each other positively under normoxic conditions during bacterial infections (Peyssonnaux et al., 2005). This amplification loop might be a key mechanism during inflammatory response. If true, the relationship between NO and HIF-1α might afford new opportunities of drug development for various inflammatory diseases.

Figure 9A:
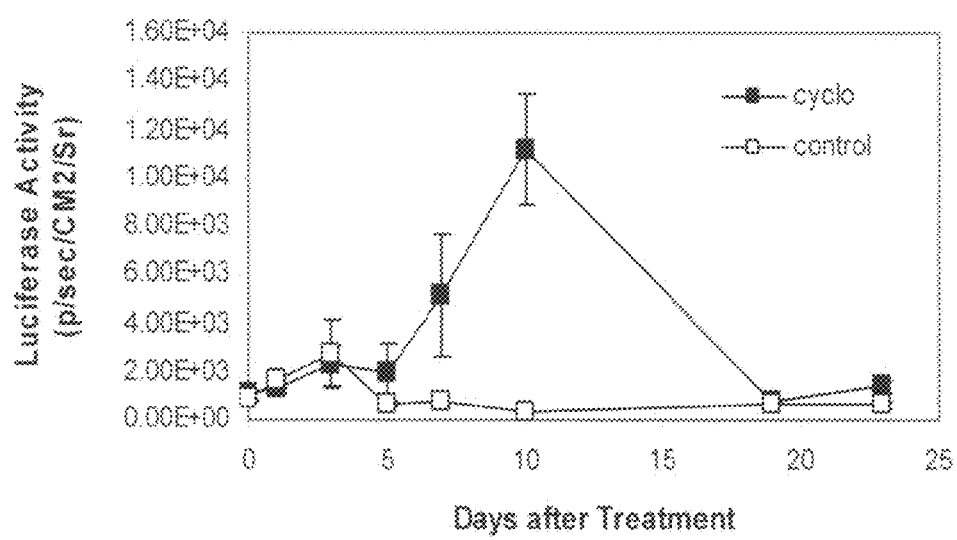
FIGS. 9A and 9B depict ODD-LUC expression in 4T1 tumor cells that have been treated with cyclophosphamide.
Figure 9B:
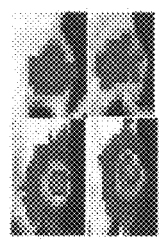

In terms of cancer therapy, the recognition that NO mediated S-nitrosylation of Cys 533 can upregulate HIF-1 activity during radiation or chemotherapy has important implications as well. This is because quite a few studies have indicated that HIF-1 plays, critical roles for tumor growth and survival during cancer therapy (Moeller et al., 2004; Yeo et al., 2003). The recognition of the role of NO in the up-regulation of HIF-1α during cancer therapy suggests a promising strategy to enhance current therapy: the use of NOS inhibitors in conjunction with conventional radiation and chemotherapy modalities. The results presented herein combining NOS inhibitor L-NAME and radiotherapy (see FIG. 7) support for this notion. A similar experiment with 4T1 tumors treated with cyclophosphamide (see FIG. 9) suggests that NOS inhibitors can also augment chemotherapy.

Although the presented studies were primarily conducted in tumors that were exposed to ionizing radiation, the same NO-mediated HIF-1 activation pathway might operate in other normal cells/tissues. Indeed, the instant co-inventors have observed NO-mediated HIF-1α activation in macrophages, fibroblasts, and epithelial cells, indicating the general applicability of this pathway.

In summary, the results presented herein establish the importance of nitric oxide-mediated S-nitrosylation in regulating the stability of HIF-1α. They indicate that S-nitrosylation of Cys533 (murine equivalent of human Cys520) in HIF-1α is directly responsible for radiation-induced HIF-1α stabilization in tumors. The instant disclosure also indicates that modulating HIF-1α activation through NOS inhibitors is a promising strategy for therapeutic development in a variety of diseases such as cancer and inflammatory diseases where it has been established that both NO and HIF-1α play prominent roles.

REFERENCES

The references listed below, as well as all references cited in the specification, including patents, patent applications, journal articles, and all database entries (e.g., GENBANK® database entries, including any annotations presented in the databases associated with the disclosed sequences), are incorporated herein by reference to the extent that they supplement, explain, provide a background for, or teach methodology, techniques, and/or compositions employed herein.

Adelman et al. (1983) *DNA* 2:183-193.
Alam & Cook (1990) *Anal Biochem* 188:245-254.
Alderton et al. (2001). *Biochem J* 357:593-615.
Altschul et al. (1990) *J Mol Biol* 215:403-410.
Ausubel et al. (1992) *Current Protocols in Molecular Biology*. Wiley, N.Y., N.Y., United States of America.
Ausubel (1995) *Short Protocols in Molecular Biology*, 3rd ed. Wiley, N.Y., N.Y., United States of America.
Bass (2001) *Nature* 411:428-429.
Brizel et al. (1999). *Radiother Oncol* 53:113-117.
Brizel et al. (1996). *Cancer Res* 56:5347-5350.
Chan et al. (2002). *J Biol Chem* 277:40112-40117.
Chen et al. (2003). *J Biol Chem* 278:13595-13598.
Cipolla et al. (2000) *Hum Gene Ther* 11:361-371.
Colombo & Mantovani (2005). *Cancer Res* 65:9113-9116.
Contag et al. (1998). *Nat Med* 4:245-247.
Cubitt et al. (1995) *Trends Biochem Sci* 20:448-455.
Cramer et al. (2003). *Cell* 112:645-657.
Dorr et al. (1997) *Cancer Chemotherapy Handbook*, 2d edition, Appleton & Lange, Stamford, Conn., United States of America.
Elbashir et al. (2001) Nature 411:494-498,
Fukuda et al. (2002). *J Biol Chem* 277:38205-38211.
Fukuda et al. (2003). *Cancer Res* 63:2330-2334.
Garcia-Barros et al. (2003). *Science* 300:1155-1159.
Giaccia et al. (2003). *Nat Rev Drug Discov* 2:803-811.
GENBANK® Accession Nos. AAA62405; AAH69465; AAP43517; AAU14021; AAX89137; AAY27087; ABB17537; BAE01417; BC069465; CAB96628; CAG29396; CAH93355; NM_000625; NP_000616; NP_001521; NP_034561; NP$_{13}$ 077335; NP_776764; NP_956527; NP_989628; S76748; U17327; U59496; and XP_852278.
Glover & Hames (1995) *DNA Cloning: A Practical Approach*, 2nd ed. IRL Press at Oxford University Press, New York, N.Y., United States of America.
Goldmann et al. (2004). *Infect Immun* 72:2956-2963.
Greenberg et al. (1994) *Mol Endocrinol* 8:230-239.
Habib et al. (1999) *Hum Gene Ther* 10:2019-2034.
Hagen et al. (2003). *Science* 302:1975-1978.
Harris (2002) *Nat Rev Cancer* 2:38-47.
Henikoff & Henikoff (1992) *Proc Natl Acad Sci USA* 89:10915-10919.
Huang et al. (1999). *Nat Biotechnol* 17:1033-1035.
Isaacs et al. (2005). *Cancer Cell* 8:143-153.
Ivan et al. (2001). *Science* 292:464-468.
Jaakkola et al. (2001). *Science* 292:468-472.
Jaffrey & Snyder (2001). *Sci STKE* 2001:PL1.
Jeong et al. (2002). *Cell* 111 :709-720.
Jiang et al. (1997). *Cancer Res* 57:5328-5335.
Jung et al. (2000). *Circ Res* 86:319-325.
Karlin & Altschul (1993) *Proc Natl Acad Sci USA* 90:5873-5877.
Kim et al. (2005). *Science* 310:1966-1970.
Kurihara et al. (2000) *J Clin Invest* 106:763-771.
Lando et al. (2002a). *Genes Dev* 16:1466-1471.
Lando et al. (2002b). *Science* 295:858-861.
Laughner et al. (2001) *Mol Cell Biol* 21:3995-4004.
Lee et al. (2000) *Anticancer Res* 20:417-422.
Leek et al. (2000). *J Pathol* 190:430-436.
Leek et al. (2002). *Cancer Res* 62:1326-1329.
Leibel & Phillips (1998) *Textbook of Radiation Oncology*, Saunders, Philadelphia, United States of America.
Lewis & Murdoch (2005). *Am J Pathol* 167:627-635.
Maltepe et al. (1997). *Nature* 386:403-407.
Matrone et al. (2004). *J Neurochem* 90:368-378.
Maxwell et al. (2001). *Adv Exp Med Biol* 502:365-376.
Maxwell et al. (1999). *Nature* 399:271-275.
Melillo (2004). *Cell Cycle* 3:154-155.
Melillo et al. (1997). *J Biol Chem* 272:12236-12243.
Metzen et al. (2003). *Mol Biol Cell* 14:3470-3481.
Moeller et al. (2004). *Cancer Cell* 5:429-441.
Moeller et al. (2005). *Cancer Cell* 8:99-110.
Muller et al. (2005). *Nat Med* 11:312-319.
Needleman & Wunsch (1970) *J Mol Biol* 48:443-453.
Ohh et al. (2000). *Nat Cell Biol* 2:423-427.
Pause et al. (1999). *Proc Natl Acad Sci USA* 96:9533-9538.
PCT International Publication Nos. WO 97/47763; WO 99/07409; WO 99/32619; WO 00/01846; WO 00/44895; WO 00/44914; WO 01/36646; and WO 01/29058.
Pearson & Lipman (1988) *Proc Natl Acad Sci USA* 85:2444-2448.
Peyssonnaux et al. (2005). *J Clin Invest* 115:1806-1815.
Rapisarda et al. (2002). *Cancer Res* 62:4316-4324.
Ravi et al. (2000). *Genes Dev* 14:34-44.
Rose & Botstein (1983) *Meth Enzymol* 101:167-180.
Sanchez-Puig et al. (2005). *Mol Cell* 17:11-21.
Sambrook & Russell (2001) *Molecular Cloning: A Laboratory Manual*, 3rd ed. Cold Spring Harbor Laboratory Press, Cold Spring Harbor, N.Y., United States of America.
Scharfmann et al. (1991) *Proc Natl Acad Sci USA* 88:4626-4630.
Selak et al. (2005). *Cancer Cell* 7:77-85.
Semenza (2002). *Trends Mol Med* 8:S62-67.
Semenza (2003) *Nat Rev Cancer* 3:721-32.
Semenza et al. (2000). *Adv Exp Med Biol* 475:123-130.
Silhavy et al. (1984) *Experiments with Gene Fusions*. Cold Spring Harbor Laboratory, Cold Spring Harbor, N.Y., United States of America.
Smith & Waterman (1981) *Adv Appl Math* 2:482-489.
Sogawa et al. (1998). *Proc Natl Acad Sci USA* 95:7368-7373.
Sumbayev et al. (2003). *FEBS Lett* 535:106-112.
Sutphin et al. (2004). *Cell Cycle* 3:160-163.
Thomsen et al. (1997). *Cancer Res* 57:3300-3304.
Tijssen (199.3) *Laboratory Techniques in Biochemistry and Molecular Biology-Hybridization with Nucleic Acid Probes*. Elsevier, N.Y., United States of America.
Udono et al. (1994). *Proc Natl Acad Sci USA* 91:3077-3081.
U.S. Pat. Nos. 5,114,951; 5,410,016; 5,411,554; 5,468,253; 5,573,934; 5,599,852; 5,631,015; 5,653,992; 5,688,900; 5,713,920; 5,728,752; 5,824,333; 5,858,746; 5,858,784; 6,013,638; 6,022,737; 6,136,295; 7,009,034; 7,011,842; and 7,012,126.
Varney et al. (2002). *In Vivo* 16:471-477.
Wachsberger et al. (2003). *Clin Cancer Res* 9:1957-1971.
Wang & Semenza (1993a). *J Biol Chem* 268:21513-21518.
Wang & Semenza (1993b). *Proc Natl Acad Sci U S A* 90:4304-4308.
Wang & Semenza (1995). *J Biol Chem* 270:1230-1237.
Williams et al. (1993) *J Clin Invest* 92:503-508.
Yasinska & Sumbayev (2003). *FEBS Lett* 549:105-109.
Yeo et al. (2003). *J Natl Cancer Inst* 95:516-525.
Yu et al. (1998). *Am J Physiol* 275:L818-826.
Yu et al. (1999) *Cancer Res* 59:4200-4203.
Zhang et al. (2004a). *Blood* 103:617-626.
Zhang et al. (2004b). *Cancer Res* 64:8139-8142.
Zhong et al. (2000). *Cancer Res* 60:1541-1545.
Zundel et al. (2000). *Genes Dev* 14:391-396.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method for enhancing radiation therapy by inhibiting a macrophage-mediated stabilization of HIF-1 in a tumor undergoing radiation therapy free of cytotoxic chemotherapy, the method comprising:
   (i) providing a radiation therapy free of cytotoxic chemotherapy by irradiating a tumor in a subject, wherein the radiation increases the number of tumor-associated macrophages, wherein the tumor-associated macrophages produce nitric oxide through inducible nitric oxide synthase, whereby the nitric oxide stabilizes HIF-1 in the irradiated tumor; and then
   (ii) contacting the irradiated tumor having stabilized HIF-1 with a composition comprising a minimally therapeutic dose of an inhibitor of inducible nitric oxide synthase to inhibit HIF-1 stabilization, whereby the minimally therapeutic dose of an inhibitor of inducible nitric oxide synthase is sufficient to prevent production of nitric oxide through inducible nitric oxide synthase in tumor-associated macrophages for a number of days following irradiation,
   whereby a macrophage-mediated stabilization of HIF-1 in the tumor is inhibited such that the radiation therapy is enhanced.

2. The method of claim 1, wherein the subject is a mammal.

3. The method of claim 2, wherein the mammal is a human.

4. The method of claim 1, wherein the composition inhibits nitrosylation of Cys520 of SEQ ID NO: 6.

5. The method of claim 1, wherein the nitric oxide produced by inducible nitric oxide synthase nitrosylates Cys520 of SEQ ID NO: 6, whereby the nitrosylation of Cys520 of SEQ ID NO: 6 stabilizes HIF-1 in the tumor.

6. The method of claim 1, wherein the tumor is irradiated in step (i), and then after a period of time the tumor is contacted with the composition in step (ii).

* * * * *

SEQUENCE LISTING

<160> NUMBER OF SEQ ID NOS: 21

<210> SEQ ID NO 1
<211> LENGTH: 824
<212> TYPE: PRT
<213> ORGANISM: Spalax judaei

<400> SEQUENCE: 1

```
Met Glu Gly Ala Gly Gly Glu Asn Glu Lys Lys Met Ser Ser Glu
1               5                   10                  15

Arg Arg Lys Glu Lys Ser Arg Asp Ala Ala Arg Ser Arg Arg Ser Lys
                20                  25                  30

Glu Ser Glu Val Phe Tyr Glu Leu Ala His Gln Leu Pro Leu Pro His
            35                  40                  45

Asn Val Ser Ser His Leu Asp Lys Ala Ser Val Met Arg Leu Thr Ile
        50                  55                  60

Ser Tyr Leu Arg Val Arg Lys Leu Leu Asp Ala Gly Asp Leu Asp Ile
65                  70                  75                  80

Glu Asp Glu Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Pro Val Lys Glu Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly Arg Ile His Val Tyr Asp Thr Asn Ser Asn Gln Pro
        195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
        275                 280                 285

Lys Thr His His Asp Met Phe Thr Lys Gly Gln Val Thr Thr Gly Gln
    290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
            340                 345                 350

Ser Leu Gln Gln Thr Glu Cys Val Leu Lys Pro Val Glu Ser Ser Asp
        355                 360                 365
```

```
Met Lys Met Thr Gln Leu Phe Thr Lys Val Glu Ser Glu Asp Thr Ser
    370             375             380
Cys Leu Phe Asp Lys Leu Lys Lys Glu Pro Asp Ala Leu Thr Met Leu
385             390             395                 400
Ala Pro Ala Ala Gly Asp Thr Ile Ile Ser Leu Asp Phe Gly Ser Asp
                405             410              415
Asp Thr Glu Thr Glu Asp Gln Gln Leu Glu Asp Val Pro Leu Tyr Asn
            420             425             430
Asp Val Met Phe Pro Ser Ser Asp Lys Leu Thr Ser Ile Asn Leu
            435             440             445
Ala Met Ser Pro Leu Pro Ala Pro Glu Thr Pro Lys Pro Leu Arg Ser
    450             455             460
Asn Ala Asp Pro Ala Leu Asn Gln Glu Val Ala Leu Lys Leu Glu Pro
465             470             475                 480
Asn Ala Glu Ser Leu Glu Leu Ser Phe Thr Met Pro Gln Ile Gln Asp
                485             490             495
Gln Pro Ala Ser Pro Ser Asp Gly Ser Thr Arg Gln Ser Ser Pro Glu
            500             505             510
Pro Asn Ser Pro Ser Glu Tyr Cys Phe Asp Val Asp Ser Asp Met Val
    515             520             525
Asn Val Phe Lys Leu Glu Leu Val Glu Lys Leu Phe Ala Glu Asp Thr
    530             535             540
Glu Ala Lys Asn Pro Phe Ser Thr Gln Asp Thr Asp Leu Asp Leu Glu
545             550             555                 560
Met Leu Ala Pro Tyr Ile Pro Met Asp Asp Asp Phe Gln Leu Arg Leu
                565             570             575
Phe Asp Gln Leu Ser Pro Leu Glu Ser Ser Ser Pro Ser Pro Pro Gly
            580             585             590
Val Asn Thr Ala Thr Ala Phe Gln Gln Thr Gln Leu Gln Glu Pro Thr
        595             600             605
Ile Ser Thr Thr Thr Thr Thr Thr Thr Asn Glu Leu Lys Thr Val
    610             615             620
Thr Lys Asp Asn Ile Glu Asp Ile Lys Ile Leu Ile Ala Ser Pro Ser
625             630             635                 640
Ser Thr His Thr Pro Lys Glu Thr Thr Thr Ala Thr Thr Ser Ser Pro
            645             650             655
Tyr Ser Gly Thr Gln Ser Arg Thr Ala Ser Pro Asn Arg Ala Gly Gln
            660             665             670
Gly Val Ile Glu Gln Thr Glu Lys Ser His Pro Arg Ser Pro Asn Leu
            675             680             685
Leu Ser Val Ser Leu Ser Gln Arg Asn Thr Val Pro Glu Glu Glu Leu
    690             695             700
Asn Pro Lys Ile Ile Ala Leu Gln Asn Ala Gln Arg Lys Arg Lys Met
705             710             715                 720
Glu His Asp Gly Ser Leu Phe Gln Ala Ala Gly Ile Gly Thr Leu Leu
                725             730             735
Gln Gln Pro Asp Asp Arg Ala Pro Ala Thr Ser Leu Ser Trp Lys Arg
            740             745             750
Val Lys Gly Cys Lys Ser Ser Gly Gln Asn Gly Met Glu Gln Lys Thr
            755             760             765
Ile Ile Leu Ile Pro Ser Asp Leu Ala Cys Arg Leu Leu Gly Gln Ser
    770             775             780
Met Asp Gly Ser Gly Leu Pro Gln Leu Thr Ser Tyr Asp Cys Glu Val
```

```
                    785                 790                 795                 800
Asn Ala Pro Ile Gln Gly Ser Arg Asn Leu Leu Gln Gly Glu Glu Leu
                805                 810                 815
Leu Arg Ala Leu Asp Gln Val Asn
                820
```

<210> SEQ ID NO 2
<211> LENGTH: 819
<212> TYPE: PRT
<213> ORGANISM: Eospalax baileyi

<400> SEQUENCE: 2

```
Met Glu Gly Ala Ala Gly Gly Glu Glu Lys Lys Asn Arg Met Ser Ser
1               5                   10                  15
Glu Arg Arg Lys Glu Lys Ser Arg Asp Ala Ala Arg Ser Arg Arg Ser
                20                  25                  30
Lys Glu Ser Glu Val Phe Tyr Glu Leu Ala His Gln Leu Pro Leu Pro
                35                  40                  45
His Asn Val Ser Ser His Leu Asp Lys Ala Ser Val Met Arg Leu Thr
            50                  55                  60
Ile Ser Tyr Leu Arg Val Arg Lys Leu Leu Asp Ala Gly Asp Leu Asp
65                  70                  75                  80
Ile Glu Asp Asp Met Lys Ala Gln Met Asn Cys Phe Tyr Leu Lys Ala
                85                  90                  95
Leu Asp Gly Phe Val Met Val Leu Thr Asp Asp Gly Asp Met Ile Tyr
                100                 105                 110
Ile Ser Asp Asn Val Asn Lys Tyr Met Gly Leu Thr Gln Phe Glu Leu
                115                 120                 125
Thr Gly His Ser Val Phe Asp Phe Thr His Pro Cys Asp His Glu Glu
            130                 135                 140
Met Arg Glu Met Leu Thr His Arg Asn Gly Pro Ile Lys Lys Gly Lys
145                 150                 155                 160
Glu Gln Asn Thr Gln Arg Ser Phe Phe Leu Arg Met Lys Cys Thr Leu
                165                 170                 175
Thr Ser Arg Gly Arg Thr Met Asn Ile Lys Ser Ala Thr Trp Lys Val
                180                 185                 190
Leu His Cys Thr Gly His Ile His Val Tyr Asp Thr Asn Ser Asn Gln
                195                 200                 205
Pro Gln Cys Gly Tyr Lys Lys Pro Pro Met Thr Cys Leu Val Leu Ile
            210                 215                 220
Cys Glu Pro Ile Pro His Pro Ser Asn Ile Glu Ile Pro Leu Asp Ser
225                 230                 235                 240
Lys Thr Phe Leu Ser Arg His Ser Leu Asp Met Lys Phe Ser Tyr Cys
                245                 250                 255
Asp Glu Arg Ile Thr Glu Leu Met Gly Tyr Glu Pro Glu Glu Leu Leu
                260                 265                 270
Gly Arg Ser Ile Tyr Glu Tyr Tyr His Ala Leu Asp Ser Asp His Leu
                275                 280                 285
Thr Lys Thr His His Asp Met Phe Thr Lys Gly Gln Val Thr Thr Gly
            290                 295                 300
Gln Tyr Arg Met Leu Ala Lys Arg Gly Gly Tyr Val Trp Val Glu Thr
305                 310                 315                 320
Gln Ala Thr Val Ile Tyr Asn Thr Lys Asn Ser Gln Pro Gln Cys Ile
                325                 330                 335
```

```
Val Cys Val Asn Tyr Val Val Ser Gly Ile Ile Gln His Asp Leu Ile
                340                 345                 350

Phe Ser Leu Gln Gln Thr Glu Cys Val Leu Lys Pro Val Glu Ser Ser
            355                 360                 365

Asp Met Lys Met Thr Gln Leu Phe Thr Lys Val Glu Ser Glu Asp Thr
        370                 375                 380

Ser Cys Leu Phe Asp Lys Leu Lys Lys Glu Pro Asp Ala Leu Thr Leu
385                 390                 395                 400

Leu Ala Pro Ala Ala Gly Asp Thr Ile Ile Ser Leu Asp Phe Gly Ser
                405                 410                 415

Asp Asp Thr Glu Thr Glu Asp Gln Gln Leu Glu Asp Val Pro Leu Tyr
            420                 425                 430

Asn Asp Val Met Phe Pro Ser Ser Asp Asp Lys Leu Thr Ser Ile Asn
        435                 440                 445

Leu Ala Met Ser Pro Leu Pro Ala Ser Glu Thr Pro Lys Pro Leu Arg
450                 455                 460

Ser Asn Ala Asp Pro Ala Leu Asn Gln Glu Val Ala Leu Lys Leu Glu
465                 470                 475                 480

Pro Asn Ala Glu Ser Leu Glu Leu Ser Phe Thr Met Pro Gln Ile Gln
                485                 490                 495

Asp Gln Pro Ala Ser Pro Ser Asp Gly Ser Thr Arg Gln Ser Ser Pro
            500                 505                 510

Glu Pro Asn Ser Pro Ser Glu Tyr Cys Phe Asp Val Asp Ser Asp Met
        515                 520                 525

Val Asn Val Phe Lys Leu Glu Leu Val Glu Lys Leu Phe Ala Glu Asp
530                 535                 540

Thr Glu Ala Lys Asn Pro Phe Ser Thr Gln Asp Thr Asp Leu Asp Leu
545                 550                 555                 560

Glu Met Leu Ala Pro Tyr Ile Pro Met Asp Asp Asp Phe Gln Leu Arg
                565                 570                 575

Ser Phe Asp Gln Leu Ser Pro Leu Glu Ser Ser Ser Pro Asn Pro Pro
            580                 585                 590

Ser Val Ser Thr Ala Phe Gln Gln Thr Gln Leu Gln Glu Pro Thr Ile
        595                 600                 605

Thr Thr Thr Thr Thr Glu Glu Leu Lys Thr Val Thr Lys Asp Ser Thr
610                 615                 620

Glu Asp Ile Lys Ile Leu Ile Thr Ser Pro Ser Ser Thr His Thr Pro
625                 630                 635                 640

Lys Glu Thr Thr Thr Ala Thr Thr Ser Ser Pro Tyr Ser Gly Thr Gln
                645                 650                 655

Ser Arg Thr Ala Ser Pro Asn Arg Ala Gly Gln Gly Val Ile Glu Gln
            660                 665                 670

Thr Glu Lys Ser His Pro Arg Ser Pro Asn Val Leu Ser Val Thr Leu
        675                 680                 685

Ser Gln Arg Asn Thr Val Pro Glu Glu Glu Leu Asn Pro Lys Ile Ile
690                 695                 700

Ala Leu Gln Asn Ala Gln Arg Lys Arg Lys Met Glu His Asp Gly Ser
705                 710                 715                 720

Leu Phe Gln Ala Ala Gly Ile Gly Thr Leu Gln Gln Pro Asp Asp
                725                 730                 735

Arg Ala Pro Ala Thr Ser Leu Ser Trp Lys Arg Val Lys Gly Cys Lys
            740                 745                 750

Ser Ser Gly Gln Asn Gly Met Glu Gln Lys Thr Ile Ile Leu Ile Pro
```

```
                755                 760                 765
Ser Asp Leu Ala Cys Arg Leu Leu Gly Gln Ser Met Asp Gly Ser Gly
770                 775                 780
Leu Pro Gln Leu Thr Ser Tyr Asp Cys Glu Val Asn Ala Pro Ile Gln
785                 790                 795                 800
Gly Ser Arg Asn Leu Leu Gln Gly Glu Glu Leu Leu Arg Ala Leu Asp
                805                 810                 815
Gln Val Asn

<210> SEQ ID NO 3
<211> LENGTH: 836
<212> TYPE: PRT
<213> ORGANISM: Mus musculus

<400> SEQUENCE: 3

Met Glu Gly Ala Gly Gly Glu Asn Glu Lys Lys Met Ser Ser Glu
1               5                   10                  15

Arg Arg Lys Glu Lys Ser Arg Asp Ala Ala Arg Ser Arg Arg Ser Lys
                20                  25                  30

Glu Ser Glu Val Phe Tyr Glu Leu Ala His Gln Leu Pro Leu Pro His
            35                  40                  45

Asn Val Ser Ser His Leu Asp Lys Ala Ser Val Met Arg Leu Thr Ile
        50                  55                  60

Ser Tyr Leu Arg Val Arg Lys Leu Leu Asp Ala Gly Gly Leu Asp Ser
65                  70                  75                  80

Glu Asp Glu Met Lys Ala Gln Met Asp Cys Phe Tyr Leu Lys Ala Leu
                85                  90                  95

Asp Gly Phe Val Met Val Leu Thr Asp Asp Gly Asp Met Val Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
130                 135                 140

Arg Glu Met Leu Thr His Arg Asn Gly Pro Val Arg Lys Gly Lys Glu
145                 150                 155                 160

Leu Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
        195                 200                 205

Gln Cys Gly Tyr Lys Lys Pro Pro Met Thr Cys Leu Val Leu Ile Cys
210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
        275                 280                 285

Lys Thr His His Asp Met Phe Thr Lys Gly Gln Val Thr Thr Gly Gln
290                 295                 300

Tyr Arg Met Leu Ala Lys Arg Gly Gly Tyr Val Trp Val Glu Thr Gln
```

```
              305                 310                 315                 320
        Ala Thr Val Ile Tyr Asn Thr Lys Asn Ser Gln Pro Gln Cys Ile Val
                        325                 330                 335

Cys Val Asn Tyr Val Val Ser Gly Ile Ile Gln His Asp Leu Ile Phe
                        340                 345                 350

Ser Leu Gln Gln Thr Glu Ser Val Leu Lys Pro Val Glu Ser Ser Asp
                        355                 360                 365

Met Lys Met Thr Gln Leu Phe Thr Lys Val Glu Ser Glu Asp Thr Ser
                        370                 375                 380

Cys Leu Phe Asp Lys Leu Lys Lys Glu Pro Asp Ala Leu Thr Leu Leu
        385                 390                 395                 400

Ala Pro Ala Ala Gly Asp Thr Ile Ile Ser Leu Asp Phe Gly Ser Asp
                        405                 410                 415

Asp Thr Glu Thr Glu Asp Gln Gln Leu Glu Asp Val Pro Leu Tyr Asn
                        420                 425                 430

Asp Val Met Phe Pro Ser Ser Asn Glu Lys Leu Asn Ile Asn Leu Ala
                        435                 440                 445

Met Ser Pro Leu Pro Ser Ser Glu Thr Pro Lys Pro Leu Arg Ser Ser
                        450                 455                 460

Ala Asp Pro Ala Leu Asn Gln Glu Val Ala Leu Lys Leu Glu Ser Ser
        465                 470                 475                 480

Pro Glu Ser Leu Gly Leu Ser Phe Thr Met Pro Gln Ile Gln Asp Gln
                        485                 490                 495

Pro Ala Ser Pro Ser Asp Gly Ser Thr Arg Gln Ser Ser Pro Glu Arg
                        500                 505                 510

Leu Leu Gln Glu Asn Val Asn Thr Pro Asn Phe Ser Gln Pro Asn Ser
                        515                 520                 525

Pro Ser Glu Tyr Cys Phe Asp Val Asp Ser Asp Met Val Asn Val Phe
                        530                 535                 540

Lys Leu Glu Leu Val Glu Lys Leu Phe Ala Glu Asp Thr Glu Ala Lys
        545                 550                 555                 560

Asn Pro Phe Ser Thr Gln Asp Thr Asp Leu Asp Leu Glu Met Leu Ala
                        565                 570                 575

Pro Tyr Ile Pro Met Asp Asp Asp Phe Gln Leu Arg Ser Phe Asp Gln
                        580                 585                 590

Leu Ser Pro Leu Glu Ser Asn Ser Pro Ser Pro Ser Met Ser Thr
                        595                 600                 605

Val Thr Gly Phe Gln Gln Thr Gln Leu Gln Lys Pro Thr Ile Thr Ala
                        610                 615                 620

Thr Ala Thr Thr Thr Ala Thr Thr Asp Glu Ser Lys Thr Glu Thr Lys
        625                 630                 635                 640

Asp Asn Lys Glu Asp Ile Lys Ile Leu Ile Ala Ser Pro Ser Ser Thr
                        645                 650                 655

Gln Val Pro Gln Glu Thr Thr Thr Ala Lys Ala Ser Ala Tyr Ser Gly
                        660                 665                 670

Thr His Ser Arg Thr Ala Ser Pro Asp Arg Ala Gly Lys Arg Val Ile
                        675                 680                 685

Glu Gln Thr Asp Lys Ala His Pro Arg Ser Leu Lys Leu Ser Ala Thr
                        690                 695                 700

Leu Asn Gln Arg Asn Thr Val Pro Glu Glu Leu Asn Pro Lys Thr
        705                 710                 715                 720

Ile Ala Ser Gln Asn Ala Gln Arg Lys Arg Lys Met Glu His Asp Gly
                        725                 730                 735
```

```
Ser Leu Phe Gln Ala Ala Gly Ile Gly Thr Leu Leu Gln Gln Pro Gly
                740                 745                 750

Asp Cys Ala Pro Thr Met Ser Leu Ser Trp Lys Arg Val Lys Gly Phe
                755                 760                 765

Ile Ser Ser Glu Gln Asn Gly Thr Glu Gln Lys Thr Ile Ile Leu Ile
                770                 775                 780

Pro Ser Asp Leu Ala Cys Arg Leu Leu Gly Gln Ser Met Asp Glu Ser
785                 790                 795                 800

Gly Leu Pro Gln Leu Thr Ser Tyr Asp Cys Glu Val Asn Ala Pro Ile
                805                 810                 815

Gln Gly Ser Arg Asn Leu Leu Gln Gly Glu Glu Leu Leu Arg Ala Leu
                820                 825                 830

Asp Gln Val Asn
        835

<210> SEQ ID NO 4
<211> LENGTH: 823
<212> TYPE: PRT
<213> ORGANISM: Rattus norvegicus

<400> SEQUENCE: 4

Met Glu Gly Ala Gly Gly Glu Asn Glu Lys Lys Asn Arg Met Ser Ser
1               5                   10                  15

Glu Arg Arg Lys Glu Lys Ser Arg Asp Ala Ala Arg Ser Arg Arg Ser
                20                  25                  30

Lys Glu Ser Glu Val Phe Tyr Glu Leu Ala His Gln Leu Pro Leu Pro
                35                  40                  45

His Asn Val Ser Ser His Leu Asp Lys Ala Ser Val Met Arg Leu Thr
            50                  55                  60

Ile Ser Tyr Leu Arg Val Arg Lys Leu Leu Gly Ala Gly Asp Leu Asp
65              70                  75                  80

Ile Glu Asp Glu Met Lys Ala Gln Met Asn Cys Phe Tyr Leu Lys Ala
                85                  90                  95

Leu Asp Gly Phe Val Met Val Leu Thr Asp Asp Gly Asp Met Ile Tyr
                100                 105                 110

Ile Ser Asp Asn Val Asn Lys Tyr Met Gly Leu Thr Gln Phe Glu Leu
                115                 120                 125

Thr Gly His Ser Val Phe Asp Phe Thr His Pro Cys Asp His Glu Glu
                130                 135                 140

Met Arg Glu Met Leu Thr His Arg Asn Gly Pro Val Arg Lys Gly Lys
145                 150                 155                 160

Glu Gln Asn Thr Gln Arg Ser Phe Phe Leu Arg Met Lys Cys Thr Leu
                165                 170                 175

Thr Ser Arg Gly Arg Thr Met Asn Ile Lys Ser Ala Thr Trp Lys Val
                180                 185                 190

Leu His Cys Thr Gly His Ile His Val Tyr Asp Thr Ser Ser Asn Gln
                195                 200                 205

Pro Gln Cys Gly Tyr Lys Lys Pro Pro Met Thr Cys Leu Val Leu Ile
                210                 215                 220

Cys Glu Pro Ile Pro His Pro Ser Asn Ile Glu Ile Pro Leu Asp Ser
225                 230                 235                 240

Lys Thr Phe Leu Ser Arg His Ser Leu Asp Met Lys Phe Ser Tyr Cys
                245                 250                 255

Asp Glu Arg Ile Thr Glu Leu Met Gly Tyr Glu Pro Glu Glu Leu Leu
```

```
                260                 265                 270
Gly Arg Ser Ile Tyr Glu Tyr Tyr His Ala Leu Asp Ser Asp His Leu
            275                 280                 285

Thr Lys Thr His His Asp Met Phe Thr Lys Gly Gln Val Thr Thr Gly
290                 295                 300

Gln Tyr Arg Met Leu Ala Lys Arg Gly Gly Tyr Val Trp Val Glu Thr
305                 310                 315                 320

Gln Ala Thr Val Ile Tyr Asn Thr Lys Asn Ser Gln Pro Gln Cys Ile
                325                 330                 335

Val Cys Val Asn Tyr Val Val Ser Gly Ile Ile Gln His Asp Leu Ile
                340                 345                 350

Phe Ser Leu Gln Gln Thr Glu Ser Val Leu Lys Pro Val Glu Ser Ser
            355                 360                 365

Asp Met Lys Met Thr Gln Leu Phe Thr Lys Val Glu Ser Glu Asp Thr
            370                 375                 380

Ser Cys Leu Phe Asp Lys Leu Lys Lys Glu Pro Asp Ala Leu Thr Leu
385                 390                 395                 400

Leu Ala Pro Ala Ala Gly Asp Thr Ile Ile Ser Leu Asp Phe Gly Ser
                405                 410                 415

Asp Asp Thr Glu Thr Glu Asp Gln Gln Leu Glu Asp Val Pro Leu Tyr
            420                 425                 430

Asn Asp Val Met Phe Pro Ser Ser Asn Glu Lys Leu Asn Ile Asn Leu
            435                 440                 445

Ala Met Ser Pro Leu Pro Ala Ser Glu Thr Pro Lys Pro Leu Arg Ser
        450                 455                 460

Ser Ala Asp Pro Ala Leu Asn Gln Glu Val Ala Leu Lys Leu Glu Ser
465                 470                 475                 480

Ser Pro Glu Ser Leu Gly Leu Ser Phe Thr Met Pro Gln Ile Gln Asp
                485                 490                 495

Gln Pro Ala Ser Pro Ser Asp Gly Ser Thr Arg Gln Ser Ser Pro Glu
            500                 505                 510

Pro Asn Ser Pro Ser Glu Tyr Cys Phe Asp Val Asp Ser Asp Met Val
        515                 520                 525

Asn Val Phe Lys Leu Glu Leu Val Glu Lys Leu Phe Ala Glu Asp Thr
530                 535                 540

Glu Ala Lys Asn Pro Phe Ser Ala Gln Asp Thr Asp Leu Asp Leu Glu
545                 550                 555                 560

Met Leu Ala Pro Tyr Ile Pro Met Asp Asp Asp Phe Gln Leu Arg Ser
                565                 570                 575

Phe Asp Gln Leu Ser Pro Leu Glu Ser Asn Ser Pro Ser Pro Pro Ser
            580                 585                 590

Val Ser Thr Val Thr Gly Phe Gln Gln Thr Gln Leu Gln Lys Pro Thr
            595                 600                 605

Ile Thr Val Thr Ala Thr Ala Thr Ala Thr Asp Glu Ser Lys Ala
        610                 615                 620

Val Thr Lys Asp Asn Ile Glu Asp Ile Lys Ile Leu Ile Ala Ser Pro
625                 630                 635                 640

Pro Ser Thr Gln Val Pro Gln Glu Met Thr Thr Ala Lys Ala Ser Ala
                645                 650                 655

Tyr Ser Gly Thr His Ser Arg Thr Ala Ser Pro Asp Arg Ala Gly Lys
            660                 665                 670

Arg Val Ile Glu Lys Thr Asp Lys Ala His Pro Arg Ser Leu Asn Leu
        675                 680                 685
```

Ser Val Thr Leu Asn Gln Arg Asn Thr Val Pro Glu Glu Leu Asn
690                 695                 700

Pro Lys Thr Ile Ala Leu Gln Asn Ala Gln Arg Lys Arg Lys Met Glu
705                 710                 715                 720

His Asp Gly Ser Leu Phe Gln Ala Ala Gly Ile Gly Thr Leu Leu Gln
            725                 730                 735

Gln Pro Gly Asp Arg Ala Pro Thr Met Ser Leu Ser Trp Lys Arg Val
        740                 745                 750

Lys Gly Tyr Ile Ser Ser Glu Gln Asp Gly Met Glu Gln Lys Thr Ile
    755                 760                 765

Phe Leu Ile Pro Ser Asp Leu Ala Cys Arg Leu Leu Gly Gln Ser Met
770                 775                 780

Asp Glu Ser Gly Leu Pro Gln Leu Thr Ser Tyr Asp Cys Glu Val Asn
785                 790                 795                 800

Ala Pro Ile Gln Gly Ser Arg Asn Leu Leu Gln Gly Glu Glu Leu Leu
            805                 810                 815

Arg Ala Leu Asp Gln Val Asn
            820

<210> SEQ ID NO 5
<211> LENGTH: 828
<212> TYPE: PRT
<213> ORGANISM: Microtus oeconomus

<400> SEQUENCE: 5

Met Glu Gly Ala Gly Gly Glu Asn Glu Lys Lys Met Ser Ser Glu
1               5                   10                  15

Arg Arg Lys Glu Lys Ser Arg Asp Ala Ala Arg Ser Arg Arg Ser Lys
                20                  25                  30

Glu Ser Glu Val Phe Tyr Glu Leu Ala His Gln Leu Pro Leu Pro His
            35                  40                  45

Asn Val Ser Ser His Leu Asp Lys Ala Ser Val Met Arg Leu Thr Ile
        50                  55                  60

Ser Tyr Leu Arg Val Arg Lys Leu Leu Asp Ala Gly Asp Leu Asp Ile
65                  70                  75                  80

Glu Asp Glu Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
130                 135                 140

Arg Glu Met Leu Thr His Arg Asn Gly Pro Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Ser
        195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys

```
                225                 230                 235                 240
        Thr Phe Leu Ser Arg His Ser Leu Asp Met Lys Phe Ser Tyr Cys Asp
                        245                 250                 255

Glu Arg Ile Thr Glu Leu Met Gly Tyr Glu Pro Glu Leu Leu Gly
                        260                 265                 270

Arg Ser Ile Tyr Glu Tyr Tyr His Ala Leu Asp Ser Asp His Leu Thr
                        275                 280                 285

Lys Thr His His Asp Met Phe Thr Lys Gly Gln Val Thr Thr Gly Gln
                    290                 295                 300

Tyr Arg Met Leu Ala Lys Arg Gly Gly Tyr Val Trp Val Glu Thr Gln
        305                 310                 315                 320

Ala Thr Val Ile Tyr Asn Thr Lys Asn Ser Gln Pro Gln Cys Ile Val
                        325                 330                 335

Cys Val Asn Tyr Val Val Ser Gly Ile Ile Gln His Asp Leu Ile Phe
                        340                 345                 350

Ser Leu Gln Gln Thr Glu Cys Val Leu Lys Pro Val Glu Ser Ser Asp
                        355                 360                 365

Met Lys Met Thr Gln Leu Phe Thr Lys Val Glu Ser Glu Asp Thr Ser
                    370                 375                 380

Cys Leu Phe Asp Lys Leu Lys Lys Glu Pro Asp Ala Leu Thr Leu Leu
        385                 390                 395                 400

Ala Pro Ala Ala Gly Asp Thr Ile Ile Ser Leu Asp Phe Gly Ser Asp
                        405                 410                 415

Asp Thr Glu Thr Glu Asp Gln Gln Leu Glu Asp Val Pro Leu Tyr Asn
                        420                 425                 430

Asp Val Met Phe Pro Ser Ser Asn Glu Lys Leu Thr Asn Ile Asn Leu
                    435                 440                 445

Ala Leu Ser Pro Leu Pro Ala Ser Glu Thr Pro Lys Pro Leu Arg Ser
                    450                 455                 460

Ser Ala Asp Pro Ala Leu Asn Gln Glu Val Ala Leu Lys Leu Glu Pro
        465                 470                 475                 480

Ser Pro Glu Ser Leu Glu Leu Ser Phe Thr Met Pro Gln Ile Gln Asp
                        485                 490                 495

Gln Pro Ala Ser Pro Ser Asp Gly Ser Thr Arg Gln Ser Ser Pro Glu
                    500                 505                 510

Pro Asn Ser Pro Ser Glu Tyr Cys Phe Asp Val Asp Ser Asp Met Val
                    515                 520                 525

Asn Val Phe Lys Leu Glu Leu Val Glu Lys Leu Phe Ala Glu Asp Thr
                    530                 535                 540

Glu Ala Lys Asn Pro Phe Ser Thr Gln Asp Thr Asp Leu Asp Leu Glu
        545                 550                 555                 560

Met Leu Ala Pro Tyr Ile Pro Met Asp Asp Asp Phe Gln Leu Arg Ser
                        565                 570                 575

Phe Asp Gln Leu Ser Pro Leu Glu Ser Ser Ser Ser Pro Pro Ser
                        580                 585                 590

Val Ser Thr Val Thr Gly Phe Gln Gln Thr Pro Leu Gln Lys Pro Thr
                    595                 600                 605

Ile Thr Ala Ala Ala Thr Thr Ala Thr Thr Ala Thr Thr Thr
                    610                 615                 620

Asp Glu Leu Lys Thr Val Thr Lys Asp Asn Ile Glu Asp Ile Lys Ile
        625                 630                 635                 640

Leu Ile Ala Ser Pro Ser Ser Val His Val Pro Gln Glu Thr Thr Ala
                        645                 650                 655
```

-continued

```
Ala Thr Ala Ser Ala Tyr Ser Ala Pro His Ser Arg Thr Ala Ser Pro
            660                 665                 670

Asp Arg Ala Gly Lys Arg Val Arg Glu Gln Ala Glu Lys Ala His Pro
        675                 680                 685

Arg Ser Pro Asn Met Ser Val Thr Leu Ser Gln Arg Asn Thr Val Thr
690                 695                 700

Glu Glu Asp Leu Asn Pro Lys Ile Ile Ala Leu Gln Asn Ala Gln Arg
705                 710                 715                 720

Lys Arg Lys Met Glu His Asp Gly Ser Leu Phe Gln Ala Ser Gly Ile
                725                 730                 735

Gly Thr Leu Leu Gln Gln Pro Gly Asp Arg Ala Pro Thr Thr Ser Leu
            740                 745                 750

Ser Trp Lys Arg Val Lys Gly Cys Lys Ser Asn Glu Gln Asn Gly Met
        755                 760                 765

Glu Gln Lys Thr Ile Ile Leu Ile Pro Ser Asp Leu Ala Cys Arg Leu
770                 775                 780

Leu Gly Gln Ser Met Asp Glu Ser Gly Leu Pro Gln Leu Thr Ser Tyr
785                 790                 795                 800

Asp Cys Glu Val Asn Ala Pro Val Gln Gly Ser Arg Asn Leu Leu Gln
                805                 810                 815

Gly Glu Asp Leu Leu Arg Ala Leu Asp Gln Val Asn
            820                 825

<210> SEQ ID NO 6
<211> LENGTH: 826
<212> TYPE: PRT
<213> ORGANISM: Homo sapiens

<400> SEQUENCE: 6

Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
```

-continued

```
                195                 200                 205
Gln Cys Gly Tyr Lys Lys Pro Pro Met Thr Cys Leu Val Leu Ile Cys
210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
                260                 265                 270

Arg Ser Ile Tyr Glu Tyr Tyr His Ala Leu Asp Ser Asp His Leu Thr
                275                 280                 285

Lys Thr His His Asp Met Phe Thr Lys Gly Gln Val Thr Thr Gly Gln
290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
                340                 345                 350

Ser Leu Gln Gln Thr Glu Cys Val Leu Lys Pro Val Glu Ser Ser Asp
                355                 360                 365

Met Lys Met Thr Gln Leu Phe Thr Lys Val Glu Ser Glu Asp Thr Ser
370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                405                 410                 415

Asp Thr Glu Thr Asp Asp Gln Gln Leu Glu Glu Val Pro Leu Tyr Asn
                420                 425                 430

Asp Val Met Leu Pro Ser Pro Asn Glu Lys Leu Gln Asn Ile Asn Leu
                435                 440                 445

Ala Met Ser Pro Leu Pro Thr Ala Glu Thr Pro Lys Pro Leu Arg Ser
450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Thr Pro Ser Pro Ser Asp Gly Ser Thr Arg Gln Ser Ser Pro Glu
                500                 505                 510

Pro Asn Ser Pro Ser Glu Tyr Cys Phe Tyr Val Asp Ser Asp Met Val
                515                 520                 525

Asn Glu Phe Lys Leu Glu Leu Val Glu Lys Leu Phe Ala Glu Asp Thr
530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Asp Phe Gln Leu Arg Ser
                565                 570                 575

Phe Asp Gln Leu Ser Pro Leu Glu Ser Ser Ser Ala Ser Pro Glu Ser
                580                 585                 590

Ala Ser Pro Gln Ser Thr Val Thr Val Phe Gln Gln Thr Gln Ile Gln
                595                 600                 605

Glu Pro Thr Ala Asn Ala Thr Thr Thr Thr Ala Thr Thr Asp Glu Leu
610                 615                 620
```

```
Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
            645                 650                 655

Ser Pro Tyr Arg Asp Thr Gln Ser Arg Thr Ala Ser Pro Asn Arg Ala
            660                 665                 670

Gly Lys Gly Val Ile Glu Gln Thr Glu Lys Ser His Pro Arg Ser Pro
            675                 680                 685

Asn Val Leu Ser Val Ala Leu Ser Gln Arg Thr Thr Val Pro Glu Glu
            690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
                725                 730                 735

Leu Leu Gln Gln Pro Asp Asp His Ala Ala Thr Thr Ser Leu Ser Trp
            740                 745                 750

Lys Arg Val Lys Gly Cys Lys Ser Ser Glu Gln Asn Gly Met Glu Gln
            755                 760                 765

Lys Thr Ile Ile Leu Ile Pro Ser Asp Leu Ala Cys Arg Leu Leu Gly
770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
                805                 810                 815

Glu Leu Leu Arg Ala Leu Asp Gln Val Asn
            820                 825

<210> SEQ ID NO 7
<211> LENGTH: 827
<212> TYPE: PRT
<213> ORGANISM: Pongo pygmaeus

<400> SEQUENCE: 7

Met Glu Gly Ala Gly Gly Ala Asn Asp Lys Lys Asn Arg Ile Ser Ser
1               5                   10                  15

Glu Arg Arg Lys Glu Lys Ser Arg Asp Ala Ala Arg Ser Arg Arg Ser
                20                  25                  30

Lys Glu Ser Glu Val Phe Tyr Glu Leu Ala His Gln Leu Pro Leu Pro
            35                  40                  45

His Asn Val Ser Ser His Leu Asp Lys Ala Ser Val Met Arg Leu Thr
        50                  55                  60

Ile Ser Tyr Leu Arg Val Arg Lys Leu Leu Asp Ala Gly Asp Leu Asp
65              70                  75                  80

Ile Glu Asp Glu Met Lys Ala Gln Met Asn Cys Phe Tyr Leu Lys Ala
                85                  90                  95

Leu Asp Gly Phe Val Met Val Leu Thr Asp Asp Gly Asp Met Ile Tyr
            100                 105                 110

Ile Ser Asp Asn Val Asn Lys Tyr Met Gly Leu Thr Gln Phe Glu Leu
        115                 120                 125

Thr Gly His Ser Val Phe Asp Phe Thr His Pro Cys Asp His Glu Glu
    130                 135                 140

Met Arg Glu Met Leu Thr His Arg Asn Gly Pro Val Lys Lys Gly Lys
145                 150                 155                 160

Glu Gln Asn Thr Gln Arg Ser Phe Phe Leu Arg Met Lys Cys Thr Leu
```

```
                165                 170                 175
Thr Ser Arg Gly Arg Thr Met Asn Ile Lys Ser Ala Thr Trp Lys Val
            180                 185                 190

Leu His Cys Thr Gly His Ile His Val Tyr Asp Thr Asn Ser Asn Gln
            195                 200                 205

Pro Gln Cys Gly Tyr Lys Lys Pro Pro Met Thr Cys Leu Val Leu Ile
            210                 215                 220

Cys Glu Pro Ile Pro His Pro Ser Asn Ile Glu Ile Pro Leu Asp Ser
225                 230                 235                 240

Lys Thr Phe Leu Ser Arg His Ser Leu Asp Met Lys Phe Ser Tyr Cys
                245                 250                 255

Asp Glu Arg Ile Thr Glu Leu Met Gly Tyr Glu Pro Glu Glu Leu Leu
            260                 265                 270

Gly Arg Ser Ile Tyr Glu Tyr Tyr His Ala Leu Asp Ser Asp His Leu
            275                 280                 285

Thr Lys Thr His His Asp Met Phe Thr Lys Gly Gln Val Thr Thr Gly
            290                 295                 300

Gln Tyr Arg Met Leu Ala Lys Arg Gly Gly Tyr Val Trp Val Glu Thr
305                 310                 315                 320

Gln Ala Thr Val Ile Tyr Asn Thr Lys Asn Ser Gln Pro Gln Cys Ile
                325                 330                 335

Val Cys Val Asn Tyr Val Val Ser Gly Ile Ile Gln His Asp Leu Ile
                340                 345                 350

Phe Ser Leu Gln Gln Thr Glu Cys Val Leu Lys Pro Val Glu Ser Ser
            355                 360                 365

Asp Met Lys Met Thr Gln Leu Phe Thr Lys Val Glu Ser Glu Asp Thr
            370                 375                 380

Ser Ser Leu Phe Asp Lys Leu Lys Lys Glu Pro Asp Ala Leu Thr Leu
385                 390                 395                 400

Leu Ala Pro Ala Ala Gly Asp Thr Ile Ile Ser Leu Asp Phe Gly Ser
                405                 410                 415

Asn Asp Thr Glu Thr Asp Asp Gln Gln Leu Glu Glu Val Pro Leu Tyr
            420                 425                 430

Asn Asp Val Met Leu Pro Ser Pro Asn Glu Lys Leu Gln Asn Ile Asn
            435                 440                 445

Leu Ala Met Ser Pro Leu Pro Thr Ala Glu Thr Pro Lys Pro Leu Arg
450                 455                 460

Ser Ser Ala Asp Pro Ala Leu Asn Gln Glu Val Ala Leu Lys Leu Glu
465                 470                 475                 480

Pro Asn Pro Glu Ser Leu Glu Leu Ser Phe Thr Met Pro Gln Ile Gln
                485                 490                 495

Asp Gln Pro Pro Ser Pro Ser Asp Gly Ser Thr Arg Gln Ser Ser Pro
                500                 505                 510

Glu Pro Asn Ser Pro Ser Glu Tyr Cys Phe Tyr Val Asp Ser Asp Met
            515                 520                 525

Val Asn Glu Phe Lys Leu Glu Leu Val Glu Lys Leu Phe Ala Glu Asp
            530                 535                 540

Thr Glu Ala Lys Asn Pro Phe Ser Thr Gln Asp Thr Asp Leu Asp Leu
545                 550                 555                 560

Glu Met Leu Ala Pro Tyr Ile Pro Met Asp Asp Phe Gln Leu Arg
                565                 570                 575

Ser Phe Asp Gln Leu Ser Pro Leu Glu Ser Ser Ser Ala Ser Pro Glu
            580                 585                 590
```

Ser Ala Ser Pro Gln Ser Thr Val Thr Val Phe Gln Gln Thr Gln Ile
            595                 600                 605

Gln Glu Pro Thr Ala Asn Ala Thr Thr Thr Thr Ala Thr Thr Asp Glu
        610                 615                 620

Leu Lys Thr Val Thr Lys Asp Arg Met Glu Asp Ile Lys Ile Leu Ile
625                 630                 635                 640

Ala Ser Pro Ser Pro Thr His Ile His Lys Glu Thr Thr Ser Ala Thr
            645                 650                 655

Ser Ser Pro Tyr Arg Asp Thr Gln Ser Arg Thr Ala Ser Pro Asn Arg
        660                 665                 670

Ala Gly Lys Gly Val Ile Glu Gln Thr Glu Lys Ser His Pro Arg Ser
    675                 680                 685

Pro Asn Val Leu Ser Val Ala Leu Ser Gln Arg Thr Thr Val Pro Glu
690                 695                 700

Glu Glu Leu Asn Pro Lys Ile Leu Ala Leu Gln Asn Ala Gln Arg Lys
705                 710                 715                 720

Arg Lys Met Glu His Asp Gly Ser Leu Phe Gln Ala Val Gly Ile Gly
            725                 730                 735

Thr Leu Leu Gln Gln Pro Glu Asp His Ala Ala Thr Thr Ser Leu Ser
        740                 745                 750

Trp Lys Arg Val Lys Gly Cys Lys Ser Ser Glu Gln Asn Gly Met Glu
    755                 760                 765

Gln Lys Thr Ile Ile Leu Ile Pro Ser Asp Leu Ala Cys Arg Leu Leu
770                 775                 780

Gly Gln Ser Met Asp Glu Ser Gly Leu Pro Gln Leu Thr Ser Tyr Asp
785                 790                 795                 800

Cys Glu Val Asn Ala Pro Ile Gln Gly Ser Arg Asn Leu Leu Gln Gly
            805                 810                 815

Glu Glu Leu Leu Arg Ala Leu Asp Gln Val Asn
        820                 825

<210> SEQ ID NO 8
<211> LENGTH: 826
<212> TYPE: PRT
<213> ORGANISM: Macaca fascicularis

<400> SEQUENCE: 8

Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65                  70                  75                  80

Glu Asp Glu Met Lys Ala Gln Met Asn Cys Phe Tyr Leu Lys Ala Leu
            85                  90                  95

Asp Gly Phe Val Met Val Leu Thr Asp Asp Gly Asp Met Ile Tyr Ile
        100                 105                 110

Ser Asp Asn Val Asn Lys Tyr Met Gly Leu Thr Gln Phe Glu Leu Thr
    115                 120                 125

Gly His Ser Val Phe Asp Phe Thr His Pro Cys Gly His Glu Glu Met

```
              130                 135                 140
Arg Glu Met Leu Thr His Arg Asn Gly Pro Val Lys Gly Lys Glu
145                 150                 155                 160

Gln Asn Thr Gln Arg Ser Phe Phe Leu Arg Met Lys Cys Thr Leu Thr
                    165                 170                 175

Ser Arg Gly Arg Thr Met Asn Ile Lys Ser Ala Thr Trp Lys Val Leu
                180                 185                 190

His Cys Thr Gly His Ile His Val Tyr Asp Thr Asn Ser Asn Gln Pro
            195                 200                 205

Gln Cys Gly Tyr Lys Lys Pro Pro Met Thr Cys Leu Val Leu Ile Cys
        210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                    245                 250                 255

Glu Arg Ile Thr Glu Leu Met Gly Tyr Glu Pro Glu Glu Leu Leu Gly
                260                 265                 270

Arg Ser Ile Tyr Glu Tyr Tyr His Ala Leu Asp Ser Asp His Leu Thr
            275                 280                 285

Lys Thr His His Gly Met Phe Thr Lys Gly Gln Val Thr Thr Gly Gln
        290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                    325                 330                 335

Cys Val Asn Tyr Val Val Ser Gly Ile Ile Gln His Asp Leu Ile Phe
                340                 345                 350

Ser Leu Gln Gln Thr Glu Cys Val Leu Lys Pro Val Glu Ser Ser Asp
            355                 360                 365

Met Lys Met Thr Gln Leu Phe Thr Lys Val Glu Ser Glu Asp Thr Ser
        370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                    405                 410                 415

Asp Thr Glu Thr Asp Asp Gln Gln Leu Glu Glu Val Pro Leu Tyr Asn
                420                 425                 430

Asp Val Met Leu Pro Ser Ser Asn Glu Lys Leu Gln Asn Ile Asn Leu
            435                 440                 445

Ala Met Ser Pro Leu Pro Thr Ser Glu Thr Pro Lys Pro Leu Arg Ser
        450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                    485                 490                 495

Gln Pro Pro Ser Pro Ser Asp Gly Ser Thr Arg Gln Ser Ser Pro Glu
                500                 505                 510

Pro Asn Ser Pro Ser Glu Tyr Cys Phe Tyr Val Asp Ser Asp Met Val
            515                 520                 525

Asn Glu Phe Lys Leu Glu Leu Val Glu Lys Leu Phe Ala Glu Asp Thr
        530                 535                 540

Glu Ala Lys Asn Pro Phe Ser Thr Gln Asp Thr Asp Leu Asp Leu Glu
545                 550                 555                 560
```

Met Leu Ala Pro Tyr Ile Pro Met Asp Asp Phe Gln Leu Arg Ser
            565                 570                 575

Phe Asp Gln Leu Ser Pro Leu Glu Ser Ser Ala Ser Pro Glu Ser
        580                 585                 590

Ala Ser Pro Gln Ser Thr Val Thr Val Phe Gln Thr Gln Ile Gln
        595                 600                 605

Glu Pro Thr Ala Asn Ala Thr Thr Thr Ala Thr Thr Asp Glu Leu
    610                 615                 620

Lys Thr Val Thr Lys Asp Arg Met Glu Asp Ile Lys Ile Leu Ile Ala
625                 630                 635                 640

Ser Pro Ser Ser Thr His Ile His Lys Glu Thr Thr Ser Ala Thr Ser
                645                 650                 655

Ser Pro Tyr Arg Asp Thr Gln Ser Arg Thr Ala Ser Pro Asn Arg Ala
                660                 665                 670

Gly Lys Gly Val Ile Glu Gln Thr Glu Lys Ser His Pro Arg Ser Pro
            675                 680                 685

Asn Val Leu Ser Val Thr Leu Ser Gln Arg Thr Thr Val Pro Glu Glu
690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
                725                 730                 735

Leu Leu Gln Gln Pro Asp Asp His Ala Ala Thr Thr Ser Leu Ser Trp
                740                 745                 750

Lys Arg Val Lys Gly Cys Lys Ser Ser Glu Gln Asn Gly Met Glu Gln
                755                 760                 765

Lys Thr Ile Ile Leu Ile Pro Ser Asp Leu Ala Cys Arg Leu Leu Gly
770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
                805                 810                 815

Glu Leu Leu Arg Ala Leu Asp Gln Val Asn
            820                 825

<210> SEQ ID NO 9
<211> LENGTH: 821
<212> TYPE: PRT
<213> ORGANISM: Spermophilus tridecemlineatus
<220> FEATURE:
<221> NAME/KEY: misc_feature
<222> LOCATION: (49)..(49)
<223> OTHER INFORMATION: Xaa can be any naturally occurring amino acid

<400> SEQUENCE: 9

Met Glu Gly Ala Gly Gly Thr Asn Asp Lys Lys Ile Ser Glu
1               5                   10                  15

Arg Arg Lys Glu Lys Ser Arg Asp Ala Ala Arg Ser Arg Ser Lys
            20                  25                  30

Glu Ser Glu Val Phe Tyr Glu Leu Ala His Gln Leu Pro Leu Pro His
        35                  40                  45

Xaa Val Ser Ser His Leu Asp Lys Ala Ser Val Met Arg Leu Thr Ile
    50                  55                  60

Ser Tyr Leu Leu Val Arg Lys Leu Leu Asp Ala Gly Asp Leu Asp Ile
65                  70                  75                  80

-continued

Glu Asp Glu Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
            115                 120                 125

Gly His Ser Val Phe Asp Phe Thr His Pro Cys Asp His Glu Glu Met
        130                 135                 140

Arg Glu Met Leu Thr His Arg Asn Gly Pro Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Ser
            195                 200                 205

Gln Cys Gly Tyr Lys Lys Pro Pro Met Thr Cys Leu Val Leu Ile Cys
        210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
        275                 280                 285

Lys Thr His His Asp Met Phe Thr Lys Gly Gln Val Thr Thr Gly Gln
290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
            325                 330                 335

Cys Val Asn Tyr Val Val Ser Gly Ile Ile Gln His Gly Leu Ile Phe
            340                 345                 350

Ser Leu Gln Gln Thr Glu Cys Val Leu Lys Pro Val Glu Ser Ser Asp
        355                 360                 365

Met Lys Met Thr Gln Leu Phe Thr Lys Val Glu Ser Glu Asp Thr Ser
        370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                405                 410                 415

Asp Thr Glu Thr Glu Asp Gln Gln Leu Glu Glu Val Pro Leu Tyr Asn
            420                 425                 430

Asp Val Met Phe Pro Ser Ser Glu Lys Leu Gln Asn Ile Asn Leu
            435                 440                 445

Ala Met Ser Pro Leu Pro Ala Ser Glu Thr Pro Lys Pro Leu Arg Ser
450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Pro Ala Ser Pro Ser Asp Gly Ser Thr Arg Gln Ser Ser Pro Glu

```
            500                 505                 510
Pro Asn Ser Pro Ser Glu Tyr Cys Phe Asp Val Asp Ser Asp Met Val
        515                 520                 525

Asn Val Phe Lys Leu Glu Leu Val Glu Lys Leu Phe Ala Glu Asp Thr
    530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Phe Gln Leu Arg Ser
                565                 570                 575

Phe Asp Gln Leu Ser Pro Leu Glu Ser Ser Ser Ser Pro Gln Ser
            580                 585                 590

Val Ser Thr Ile Ser Val Phe Gln Gln Thr Gln Ile Gln Glu Pro Thr
        595                 600                 605

Ile Asn Thr Thr Thr Ala Thr Thr Asp Glu Leu Lys Thr Val Thr Lys
    610                 615                 620

Asp Asp Met Glu Asp Ile Lys Ile Leu Ile Ala Ser Trp Ser Pro Thr
625                 630                 635                 640

His Ala Pro Lys Glu Thr Thr Ser Ala Thr Thr Ser Ser Tyr Asn Asp
                645                 650                 655

Thr Gln Ser Arg Thr Ala Ser Pro Asn Arg Ala Gly Lys Glu Val Ile
            660                 665                 670

Glu Gln Thr Glu Lys Ser His Pro Arg Ser Pro Asn Val Val Ser Val
        675                 680                 685

Thr Leu Ser Gln Arg Asn Thr Val Pro Glu Glu Leu Asn Pro Lys
    690                 695                 700

Ile Leu Ala Leu Gln Asn Ala Gln Lys Lys Ala Lys Met Glu Gln Asp
705                 710                 715                 720

Gly Ser Leu Phe Gln Ala Val Gly Ile Gly Thr Leu Leu Gln Gln Pro
                725                 730                 735

Asp Asp Arg Ala Thr Thr Thr Ser Leu Ser Trp Lys Arg Val Lys Gly
            740                 745                 750

Cys Lys Ser Ser Glu Gln Asn Gly Met Glu Gln Lys Thr Ile Ile Leu
        755                 760                 765

Ile Pro Ser Asp Leu Ala Cys Arg Leu Leu Gly Gln Ser Met Asp Glu
    770                 775                 780

Ser Gly Leu Pro Gln Leu Thr Ser Tyr Asp Cys Glu Val Asn Ala Pro
785                 790                 795                 800

Ile Gln Gly Ser Arg Asn Leu Leu Gln Gly Glu Glu Leu Leu Arg Ala
                805                 810                 815

Leu Asp Gln Val Asn
            820

<210> SEQ ID NO 10
<211> LENGTH: 823
<212> TYPE: PRT
<213> ORGANISM: Bos taurus

<400> SEQUENCE: 10

Met Glu Gly Ala Gly Gly Ala Asn Asp Lys Lys Ile Ser Ser Glu
1               5                   10                  15

Arg Arg Lys Glu Lys Ser Arg Asp Ala Ala Arg Ser Arg Arg Ser Lys
                20                  25                  30

Glu Ser Glu Val Phe Tyr Glu Leu Ala His Gln Leu Pro Leu Pro His
            35                  40                  45
```

```
Asn Val Ser Ser His Leu Asp Lys Ala Ser Val Met Arg Leu Thr Ile
 50                  55                  60

Ser Tyr Leu Arg Val Arg Lys Leu Leu Asp Ala Gly Asp Leu Asp Ile
 65                  70                  75                  80

Glu Asp Glu Met Lys Ala Gln Met Asn Cys Phe Tyr Leu Lys Ala Leu
                 85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Ser
        195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
        275                 280                 285

Lys Thr His His Asp Met Phe Thr Lys Gly Gln Val Thr Thr Gly Gln
290                 295                 300

Tyr Arg Met Leu Ala Lys Arg Gly Gly Tyr Val Trp Ile Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
            340                 345                 350

Ser Leu Gln Gln Thr Glu Cys Val Leu Lys Pro Val Glu Ser Ser Asp
        355                 360                 365

Met Lys Met Thr Gln Leu Phe Thr Lys Val Glu Ser Glu Asp Thr Ser
370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                405                 410                 415

Asp Thr Glu Thr Asp Asp Gln Gln Leu Glu Glu Val Pro Leu Tyr Asn
            420                 425                 430

Asp Val Met Leu Pro Ser Ser Asn Glu Lys Leu Gln Asn Ile Asn Leu
        435                 440                 445

Ala Met Ser Pro Leu Pro Ala Ser Glu Thr Pro Lys Pro Leu Arg Ser
450                 455                 460

Ser Ala Asp Pro Ala Leu Asn Gln Glu Val Ala Leu Lys Leu Glu Pro
```

```
                465                 470                 475                 480
Asn Pro Glu Ser Leu Glu Leu Ser Phe Thr Met Pro Gln Ile Gln Asp
                485                 490                 495
Gln Pro Ala Ser Pro Ser Asp Gly Ser Thr Arg Gln Ser Ser Pro Glu
            500                 505                 510
Pro Asn Ser Pro Ser Glu Tyr Cys Phe Asp Val Asp Ser Asp Met Val
        515                 520                 525
Asn Glu Phe Lys Leu Glu Leu Val Glu Lys Leu Phe Ala Glu Asp Thr
    530                 535                 540
Glu Ala Lys Asn Pro Phe Ser Thr Gln Asp Thr Asp Leu Asp Leu Glu
545                 550                 555                 560
Met Leu Ala Pro Tyr Ile Pro Met Asp Asp Asp Phe Gln Leu Arg Ser
                565                 570                 575
Phe Asp Gln Leu Ser Pro Leu Glu Asn Ser Ser Thr Ser Pro Gln Ser
                580                 585                 590
Ala Ser Thr Asn Thr Val Phe Gln Pro Thr Gln Met Gln Lys Pro Pro
            595                 600                 605
Ile Ala Thr Val Thr Thr Thr Ala Thr Ser Asp Glu Leu Lys Thr Val
        610                 615                 620
Thr Lys Asp Gly Met Glu Asp Ile Lys Ile Leu Ile Ala Phe Pro Ser
625                 630                 635                 640
Pro Pro His Val Pro Lys Glu Pro Pro Cys Ala Thr Thr Ser Pro Tyr
                645                 650                 655
Ser Asp Thr Gly Ser Arg Thr Ala Ser Pro Asn Arg Ala Gly Lys Gly
                660                 665                 670
Val Ile Glu Gln Thr Glu Lys Ser His Pro Arg Ser Pro Asn Val Leu
            675                 680                 685
Ser Val Ala Leu Ser Gln Arg Thr Thr Ala Pro Glu Glu Leu Asn
        690                 695                 700
Pro Lys Ile Leu Ala Leu Gln Asn Ala Gln Arg Lys Arg Lys Ile Glu
705                 710                 715                 720
His Asp Gly Ser Leu Phe Gln Ala Val Gly Ile Gly Thr Leu Leu Gln
                725                 730                 735
Gln Pro Asp Asp Arg Ala Thr Thr Thr Ser Leu Ser Trp Lys Arg Val
            740                 745                 750
Lys Gly Cys Lys Ser Ser Glu Gln Asn Gly Met Glu Gln Lys Thr Ile
        755                 760                 765
Ile Leu Ile Pro Ser Asp Leu Ala Cys Arg Leu Leu Gly Gln Ser Met
    770                 775                 780
Asp Glu Ser Gly Leu Pro Gln Leu Thr Ser Tyr Asp Cys Glu Val Asn
785                 790                 795                 800
Ala Pro Ile Gln Gly Ser Arg Asn Leu Leu Gln Gly Glu Glu Leu Leu
                805                 810                 815
Arg Ala Leu Asp Gln Val Asn
            820

<210> SEQ ID NO 11
<211> LENGTH: 823
<212> TYPE: PRT
<213> ORGANISM: Pantholops hodgsonii

<400> SEQUENCE: 11

Met Glu Gly Ala Gly Gly Ala Asn Asp Lys Lys Lys Ile Ser Ser Glu
1               5                   10                  15
```

```
Arg Arg Lys Glu Lys Ser Arg Asp Ala Ala Arg Ser Arg Arg Ser Lys
             20                  25                  30

Glu Ser Glu Val Phe Tyr Glu Leu Ala His Gln Leu Pro Leu Pro His
         35                  40                  45

Asn Val Ser Ser His Leu Asp Lys Ala Ser Val Met Arg Leu Thr Ile
     50                  55                  60

Ser Tyr Leu Arg Val Arg Lys Leu Leu Asp Ala Gly Asp Leu Asp Ile
 65                  70                  75                  80

Glu Asp Glu Met Lys Ala Gln Met Asn Cys Phe Tyr Leu Lys Ala Leu
                 85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Ser
        195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
        275                 280                 285

Lys Thr His His Asp Met Phe Thr Lys Gly Gln Val Thr Thr Gly Gln
    290                 295                 300

Tyr Arg Met Leu Ala Lys Arg Gly Gly Tyr Val Trp Ile Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
            340                 345                 350

Ser Leu Gln Gln Thr Glu Cys Val Leu Lys Pro Val Glu Ser Ser Asp
        355                 360                 365

Met Lys Met Thr Gln Leu Phe Thr Lys Val Glu Ser Glu Asp Thr Ser
    370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                405                 410                 415

Asp Ala Glu Thr Asp Asp Gln Gln Leu Glu Glu Val Pro Leu Tyr Asn
            420                 425                 430

Asp Val Met Leu Pro Ser Ser Asn Glu Lys Leu Gln Asn Ile Asn Leu
```

```
            435                 440                 445
Ala Met Ser Pro Leu Pro Ala Ser Glu Thr Pro Lys Pro Leu Arg Ser
    450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Pro Ala Ser Pro Ser Asp Gly Ser Thr Arg Gln Ser Ser Pro Glu
            500                 505                 510

Pro Asn Ser Pro Ser Glu Tyr Cys Phe Asp Val Asp Ser Asp Met Val
        515                 520                 525

Asn Glu Phe Lys Leu Glu Leu Val Glu Lys Leu Phe Ala Glu Asp Thr
    530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Asp Phe Gln Leu Arg Ser
                565                 570                 575

Phe Asp Gln Leu Ser Pro Leu Glu Asn Ser Ser Thr Ser Pro Gln Ser
            580                 585                 590

Ala Ser Thr Asp Thr Val Phe Gln Pro Thr Gln Met Gln Glu Pro Pro
        595                 600                 605

Ile Ala Thr Ala Thr Thr Thr Ala Thr Asn Asp Glu Leu Lys Thr Val
    610                 615                 620

Thr Lys Asp Gly Met Glu Asp Ile Lys Ile Leu Ile Ala Phe Pro Ser
625                 630                 635                 640

Pro Pro His Val Pro Lys Glu Pro Pro Cys Ala Thr Thr Ser Pro Tyr
                645                 650                 655

Ser Asp Thr Gly Ser Arg Thr Ala Ser Pro Asn Arg Ala Gly Lys Gly
            660                 665                 670

Val Ile Glu Gln Thr Glu Lys Ser His Pro Arg Ser Pro Asn Val Leu
        675                 680                 685

Ser Val Ala Leu Ser Gln Arg Thr Thr Ala Pro Glu Glu Glu Leu Asn
    690                 695                 700

Pro Lys Ile Leu Ala Leu Gln Asn Ala Gln Arg Lys Arg Lys Ile Glu
705                 710                 715                 720

His Asp Gly Ser Leu Phe Gln Ala Val Gly Ile Gly Thr Leu Leu Gln
                725                 730                 735

Gln Pro Asp Asp Arg Ala Thr Thr Thr Ser Leu Ser Trp Lys Arg Val
            740                 745                 750

Lys Gly Cys Lys Ser Ser Glu Gln Asn Gly Met Glu Gln Lys Thr Ile
        755                 760                 765

Ile Leu Ile Pro Ser Asp Leu Ala Cys Arg Leu Leu Gly Gln Ser Met
    770                 775                 780

Asp Glu Ser Gly Leu Pro Gln Leu Thr Ser Tyr Asp Cys Glu Val Asn
785                 790                 795                 800

Ala Pro Ile Gln Gly Ser Arg Asn Leu Leu Gln Gly Glu Glu Leu Leu
                805                 810                 815

Arg Ala Leu Asp Gln Val Asn
            820

<210> SEQ ID NO 12
<211> LENGTH: 823
<212> TYPE: PRT
<213> ORGANISM: Canis familiaris
```

<400> SEQUENCE: 12

```
Met Glu Gly Ala Gly Gly Ala Asn Asp Lys Lys Ile Ser Ser Glu
1               5                   10                  15

Arg Arg Lys Glu Lys Ser Arg Asp Ala Ala Arg Ser Arg Arg Ser Lys
                20                  25                  30

Glu Ser Glu Val Phe Tyr Glu Leu Ala His Gln Leu Pro Leu Pro His
            35                  40                  45

Asn Val Ser Ser His Leu Asp Lys Ala Ser Val Met Arg Leu Thr Ile
        50                  55                  60

Ser Tyr Leu Arg Val Arg Lys Leu Leu Asp Ala Gly Asp Leu Asp Ile
65                  70                  75                  80

Glu Asp Glu Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
130                 135                 140

Arg Glu Met Leu Thr His Arg Asn Gly Leu Val Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Ser
        195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser His Leu Thr
        275                 280                 285

Lys Thr His His Asp Met Phe Thr Lys Gly Gln Val Thr Thr Gly Gln
    290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
            340                 345                 350

Ser Leu Gln Gln Thr Glu Cys Val Leu Lys Pro Val Glu Ser Ser Asp
        355                 360                 365

Met Lys Met Thr Gln Leu Phe Thr Lys Val Glu Ser Glu Asp Thr Ser
    370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
```

```
                    405                 410                 415
Asp Thr Glu Thr Asp Gln Gln Leu Glu Glu Val Pro Leu Tyr Asn
                420                 425                 430

Asp Val Met Leu Pro Ser Ser Asn Glu Lys Leu Gln Asn Ile Asn Leu
            435                 440                 445

Ala Met Ser Pro Leu Pro Ala Ser Glu Thr Pro Lys Pro Leu Arg Ser
        450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Pro Ala Ser Pro Ser Asp Gly Ser Thr Arg Gln Ser Ser Pro Glu
                500                 505                 510

Pro Asn Ser Pro Ser Glu Tyr Cys Phe Asp Val Asp Ser Asp Met Val
            515                 520                 525

Asn Glu Phe Lys Leu Glu Leu Val Glu Lys Leu Phe Ala Glu Asp Thr
        530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Asp Phe Gln Leu Arg Ser
                565                 570                 575

Phe Asp Gln Leu Ser Pro Leu Glu Ser Asn Ser Thr Ser Pro Gln Ser
            580                 585                 590

Ala Ser Thr Ile Thr Val Phe Gln Pro Thr Pro Met Gln Glu Pro Pro
        595                 600                 605

Leu Thr Thr Thr Ser Thr Thr Ala Thr Thr Asp Glu Leu Lys Thr Val
610                 615                 620

Thr Lys Asp Gly Ile Glu Asp Ile Lys Ile Leu Ile Ala Ala Pro Ser
                630                 635                 640
625

Pro Thr His Val Pro Lys Val Thr Thr Ser Ala Thr Thr Ser Pro Tyr
            645                 650                 655

Ser Asp Thr Gly Ser Arg Thr Ala Ser Pro Asn Arg Ala Gly Lys Gly
        660                 665                 670

Val Ile Glu Gln Thr Glu Lys Ser His Pro Arg Ser Pro Asn Val Leu
            675                 680                 685

Ser Val Thr Leu Ser Gln Arg Thr Thr Ile Pro Glu Glu Glu Leu Asn
        690                 695                 700

Pro Lys Ile Leu Ala Leu Gln Asn Ala Gln Arg Lys Arg Lys Ile Glu
705                 710                 715                 720

His Asp Gly Ser Leu Phe Gln Ala Val Gly Ile Gly Thr Leu Leu Gln
                725                 730                 735

Gln Pro Asp Asp Arg Ala Thr Thr Thr Ser Leu Ser Trp Lys Arg Val
            740                 745                 750

Lys Gly Cys Lys Ser Ser Glu Gln Asn Gly Met Glu Gln Lys Thr Ile
        755                 760                 765

Ile Leu Ile Pro Ser Asp Leu Ala Cys Arg Leu Leu Gly Gln Ser Met
    770                 775                 780

Asp Glu Ser Gly Leu Pro Gln Leu Thr Ser Tyr Asp Cys Glu Val Asn
785                 790                 795                 800

Ala Pro Ile Gln Gly Ser Arg Asn Leu Leu Gln Gly Glu Glu Leu Leu
                805                 810                 815

Arg Ala Leu Asp Gln Val Asn
                820
```

<210> SEQ ID NO 13
<211> LENGTH: 819
<212> TYPE: PRT
<213> ORGANISM: Oryctolagus cuniculus

<400> SEQUENCE: 13

```
Met Glu Gly Ala Gly Gly Ala Asn Asp Lys Lys Ile Ser Ser Glu
1               5                   10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65              70                  75                  80

Glu Asp Glu Met Lys Ala Gln Met Asn Cys Phe Tyr Leu Lys Ala Leu
            85                  90                  95

Asp Gly Phe Val Met Val Leu Thr Asp Asp Gly Asp Met Ile Tyr Ile
        100                 105                 110

Ser Asp Asn Val Asn Lys Tyr Met Gly Leu Thr Gln Phe Glu Leu Thr
    115                 120                 125

Gly His Ser Val Phe Asp Phe Thr His Pro Cys Asp His Glu Glu Met
130                 135                 140

Arg Glu Met Leu Thr His Arg Asn Gly Pro Val Lys Lys Gly Lys Glu
145                 150                 155                 160

Gln Asn Thr Gln Arg Ser Phe Phe Leu Arg Met Lys Cys Thr Leu Thr
            165                 170                 175

Ser Arg Gly Arg Thr Met Asn Ile Lys Ser Ala Thr Trp Lys Val Leu
        180                 185                 190

His Cys Thr Gly His Ile His Val Tyr Asp Thr Asn Ser Asn Gln Ser
    195                 200                 205

Gln Cys Gly Tyr Lys Lys Pro Pro Met Thr Cys Leu Val Leu Ile Cys
210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
            245                 250                 255

Glu Arg Ile Thr Glu Leu Met Gly Tyr Glu Pro Glu Glu Leu Leu Gly
        260                 265                 270

Arg Ser Ile Tyr Glu Tyr Tyr His Ala Leu Asp Ser Asp His Leu Thr
    275                 280                 285

Lys Thr His His Asp Met Phe Thr Lys Gly Gln Val Thr Thr Gly Gln
290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
            325                 330                 335

Cys Val Asn Tyr Val Val Ser Gly Ile Ile Gln His Asp Leu Ile Phe
        340                 345                 350

Ser Leu Gln Gln Thr Glu Cys Val Leu Lys Pro Val Glu Ser Ser Asp
    355                 360                 365

Met Lys Met Thr Gln Leu Phe Thr Lys Val Glu Ser Ala Asp Thr Ser
```

```
                370                 375                 380
Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                405                 410                 415

Asp Thr Glu Thr Asp Asp Gln Gln Leu Glu Val Pro Leu Tyr Asn
                420                 425                 430

Asp Val Met Phe Pro Ser Ser Asn Glu Lys Leu Gln Asp Ile Asn Leu
                435                 440                 445

Ala Met Ser Pro Leu Pro Ala Ser Glu Ser Pro Lys Pro Leu Arg Ser
                450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Pro Ala Ser Pro Ser Asp Gly Ser Thr Arg Gln Ser Ser Pro Glu
                500                 505                 510

Pro Thr Ser Pro Ser Glu Tyr Cys Phe Asp Val Asp Ser Asp Met Val
                515                 520                 525

Asn Val Phe Lys Leu Glu Leu Val Glu Lys Leu Phe Ala Glu Asp Thr
                530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Asp Phe Gln Leu Arg Ser
                565                 570                 575

Phe Asp Gln Leu Ser Pro Leu Glu Ser Ser Ser Ala Gly Ala Val Thr
                580                 585                 590

Val Phe Pro Gln Thr Gln Gly Gln Glu Pro Ala Ala Asn Thr Ala Pro
                595                 600                 605

Cys Ala Pro Pro Pro Leu Thr Ile Lys Thr Ser Ala Lys Asp Ser Val
610                 615                 620

Glu Asp Met Lys Val Leu Ile Ala Ser Pro Ser Pro Asn His Ile Pro
625                 630                 635                 640

Lys Glu Thr Ala Ser Ala Thr Thr Ser Pro Pro Tyr Arg Asp Thr Pro
                645                 650                 655

Ser Arg Thr Ala Ser Pro Asn Thr Ala Gly Lys Gly Val Ile Glu Gln
                660                 665                 670

Thr Glu Lys Ser His Pro Arg Ser Pro Asn Val Leu Ala Val Thr Leu
                675                 680                 685

Ser Gln Arg Thr Thr Ala Pro Glu Glu Glu Leu Asn Pro Lys Ile Leu
                690                 695                 700

Ala Leu Gln Asn Ala Gln Arg Lys Arg Lys Met Glu Ser Asp Gly Ser
705                 710                 715                 720

Leu Phe Gln Ala Val Gly Ile Gly Thr Leu Leu Gln Gln Pro Asp Asp
                725                 730                 735

Arg Thr Thr Thr Ala Ser Leu Ser Trp Lys Arg Val Lys Gly Cys Lys
                740                 745                 750

Ser Ser Glu Gln Asn Gly Met Glu Gln Lys Thr Ile Ile Leu Ile Pro
                755                 760                 765

Ser Asp Leu Ala Cys Arg Leu Leu Gly Gln Ser Met Asp Glu Ser Gly
                770                 775                 780

Leu Pro Gln Leu Thr Ser Tyr Asp Cys Glu Val Asn Ala Pro Ile Gln
785                 790                 795                 800
```

Gly Ser Arg Asn Leu Leu Gln Gly Glu Glu Leu Leu Arg Ala Leu Asp
            805                 810                 815

Gln Val Asn

<210> SEQ ID NO 14
<211> LENGTH: 811
<212> TYPE: PRT
<213> ORGANISM: Gallus gallus

<400> SEQUENCE: 14

Met Asp Ser Pro Gly Gly Val Thr Asp Lys Lys Arg Ile Ser Ser Glu
1               5                   10                  15

Arg Arg Lys Glu Lys Ser Arg Asp Ala Ala Arg Cys Arg Arg Ser Lys
            20                  25                  30

Glu Ser Glu Val Phe Tyr Glu Leu Ala His Gln Leu Pro Leu Pro His
        35                  40                  45

Thr Val Ser Ala His Leu Asp Lys Ala Ser Ile Met Arg Leu Thr Ile
    50                  55                  60

Ser Tyr Leu Arg Met Arg Lys Leu Leu Asp Ala Gly Glu Leu Glu Thr
65                  70                  75                  80

Glu Ala Asn Met Glu Lys Glu Leu Asn Cys Phe Tyr Leu Lys Ala Leu
                85                  90                  95

Asp Gly Phe Val Met Val Leu Ser Glu Asp Gly Asp Met Ile Tyr Met
            100                 105                 110

Ser Glu Asn Val Asn Lys Cys Met Gly Leu Thr Gln Phe Asp Leu Thr
        115                 120                 125

Gly His Ser Val Phe Asp Phe Thr His Pro Cys Asp His Glu Glu Leu
    130                 135                 140

Arg Glu Met Leu Thr His Arg Asn Gly Pro Val Lys Lys Gly Lys Glu
145                 150                 155                 160

Gln Asn Thr Glu Arg Ser Phe Phe Leu Arg Met Lys Cys Thr Leu Thr
                165                 170                 175

Ser Arg Gly Arg Thr Val Asn Ile Lys Ser Ala Thr Trp Lys Val Leu
            180                 185                 190

His Cys Thr Gly His Ile Arg Val Tyr Asp Thr Cys Asn Asn Gln Thr
        195                 200                 205

His Cys Gly Tyr Lys Lys Pro Pro Met Thr Cys Leu Val Leu Ile Cys
    210                 215                 220

Glu Pro Ile Pro His Pro Ser Asn Ile Glu Val Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
        275                 280                 285

Lys Thr His His Asp Met Phe Thr Lys Gly Gln Val Thr Thr Gly Gln
    290                 295                 300

Tyr Arg Met Leu Ala Lys Gln Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Leu Ser Gly Ile Val Gln Lys Asp Leu Ile Phe
            340                 345                 350

```
Ser Leu Gly Gln Thr Glu Cys Met Leu Lys Pro Val Glu Ser Pro Glu
            355                 360                 365

Met Lys Met Thr Lys Ile Phe Ser Lys Asp Asp Trp Asp Asp Thr Asn
    370                 375                 380

Ser Leu Phe Glu Lys Leu Lys Gln Glu Pro Asp Ala Leu Thr Val Leu
385                 390                 395                 400

Ala Pro Ala Ala Gly Asp Thr Ile Ile Ser Leu Asp Phe Ser Ser Asn
                405                 410                 415

Glu Ser Asp Glu Gln Gln Cys Asp Glu Val Pro Leu Tyr Asn Asp Val
            420                 425                 430

Met Leu Pro Ser Ser Glu Lys Leu Gln Asn Ile Asn Ile Ala Met
            435                 440                 445

Ser Pro Leu Pro Ala Ser Glu Thr Thr Lys Pro Leu Arg Ser Asn Ala
            450                 455                 460

Asp Pro Ala Leu Asn Arg Glu Val Val Ser Lys Leu Glu Pro Asn Thr
465                 470                 475                 480

Glu Thr Leu Glu Leu Ser Phe Thr Met Pro Gln Val Gln Glu Gln Pro
                485                 490                 495

Thr Ser Pro Ser Asp Ala Ser Thr Ser Gln Ser Ser Pro Glu Pro Ser
            500                 505                 510

Ser Pro Asn Asp Tyr Cys Phe Asp Val Asp Asn Asp Met Ala Asn Glu
            515                 520                 525

Phe Lys Leu Glu Leu Val Glu Lys Leu Phe Ala Ile Asp Thr Glu Ala
            530                 535                 540

Lys Asn Pro Phe Ser Thr Gln Glu Thr Asp Leu Asp Leu Glu Met Leu
545                 550                 555                 560

Ala Pro Tyr Ile Pro Met Asp Asp Asp Phe Gln Leu Arg Ser Phe Asp
                565                 570                 575

Gln Leu Ser Pro Leu Glu Ser Ser Ser Gly Ser Gln Asn Ala Ala
            580                 585                 590

Thr Ile Thr Ile Leu Gln Gln Thr Gln Thr Pro Ser Thr Ala Ala Asp
            595                 600                 605

Glu Ile Lys Pro Val Ala Glu Arg Val Asp Asp Val Lys Ala Leu Ile
610                 615                 620

Val Pro Ser Ser Pro Val His Val Ile Asn Asp Thr Ser Ser Ala Pro
625                 630                 635                 640

Ala Ser Pro Tyr Ser Gly Asn Arg Ser Arg Thr Ala Ser Pro Ile Arg
                645                 650                 655

Ala Gly Lys Gly Thr Leu Glu Gln Thr Glu Lys Ser Cys Pro Gly Ala
            660                 665                 670

Pro Ser Leu Ile Thr Val Thr Leu Asn Lys Arg Ser Thr Ala Met Asp
            675                 680                 685

Glu Glu Leu Asn Pro Lys Met Leu Ala Leu His Asn Ala Gln Arg Lys
            690                 695                 700

Arg Lys Met Glu His Asp Gly Ser Leu Phe Gln Ala Val Gly Ile Gly
705                 710                 715                 720

Ser Leu Phe Gln Gln Thr Gly Asp Arg Gly Asn Ala Ser Leu Ala
            725                 730                 735

Trp Lys Arg Val Lys Ala Cys Lys Thr Asn Gly His Asn Gly Val Glu
            740                 745                 750

Gln Lys Thr Ile Ile Leu Leu Ser Thr Asp Ile Ala Ser Lys Leu Leu
            755                 760                 765
```

```
Gly Gln Ser Met Asp Glu Ser Gly Leu Pro Gln Leu Thr Ser Tyr Asp
    770                 775                 780

Cys Glu Val Asn Ala Pro Ile Gln Gly Asn Arg Asn Leu Leu Gln Gly
785                 790                 795                 800

Glu Glu Leu Leu Arg Ala Leu Asp Gln Val Asn
                805                 810

<210> SEQ ID NO 15
<211> LENGTH: 533
<212> TYPE: PRT
<213> ORGANISM: Danio rerio

<400> SEQUENCE: 15

Met Asp Thr Gly Val Thr Glu Lys Lys Arg Val Ser Ser Glu Arg
1               5                   10                  15

Arg Lys Gly Lys Ser Arg Asp Ala Ala Arg Ser Arg Gly Lys Glu
                20                  25                  30

Ser Glu Val Phe Tyr Glu Leu Ala His Gln Leu Pro Leu Pro His Asn
                35                  40                  45

Val Thr Ser His Leu Asp Lys Ala Ser Ile Met Arg Leu Thr Ile Ser
    50                  55                  60

Tyr Leu Arg Met Arg Lys Leu Leu Asn Ser Asp Glu Lys Glu Glu Lys
65                  70                  75                  80

Glu Glu Asn Glu Leu Gly Ser Gln Leu Asn Gly Phe Tyr Leu Lys Ala
                85                  90                  95

Leu Glu Gly Phe Leu Met Val Leu Ser Glu Asp Gly Asp Met Val Tyr
                100                 105                 110

Leu Ser Glu Asn Val Ser Lys Ser Met Gly Leu Thr Gln Phe Asp Leu
                115                 120                 125

Thr Gly His Ser Ile Phe Glu Phe Ser His Pro Cys Asp His Glu Glu
    130                 135                 140

Leu Arg Glu Met Leu Val His Arg Thr Gly Ser Lys Lys Thr Lys Glu
145                 150                 155                 160

Gln Asn Thr Glu Arg Ser Phe Phe Leu Arg Met Lys Cys Thr Leu Thr
                165                 170                 175

Ser Arg Gly Arg Thr Val Asn Ile Lys Ser Ala Thr Trp Lys Val Leu
                180                 185                 190

His Cys Ala Gly His Val Arg Val His Glu Gly Ser Glu Ala Ser Glu
    195                 200                 205

Asp Ser Gly Phe Lys Glu Pro Pro Val Thr Tyr Leu Val Leu Ile Cys
210                 215                 220

Glu Pro Ile Pro His Pro Ser Asn Ile Glu Val Pro Leu Asp Ser Lys
225                 230                 235                 240

Thr Phe Leu Ser Arg His Thr Leu Asp Met Lys Phe Ser Tyr Cys Asp
                245                 250                 255

Glu Arg Ile Thr Glu Leu Met Gly Tyr Glu Pro Asp Asp Leu Leu Asn
                260                 265                 270

Arg Ser Val Tyr Glu Tyr Tyr His Ala Leu Asp Ser Asp His Leu Thr
                275                 280                 285

Lys Thr His His Asn Leu Phe Ala Lys Gly Gln Ala Thr Thr Gly Gln
    290                 295                 300

Tyr Arg Met Leu Ala Lys Lys Gly Gly Phe Val Trp Val Glu Thr Gln
305                 310                 315                 320

Ala Thr Val Ile Tyr Asn Pro Lys Asn Ser Gln Pro Gln Cys Ile Val
                325                 330                 335
```

```
Cys Val Asn Tyr Val Leu Ser Gly Ile Val Glu Gly Asp Val Val Leu
            340                 345                 350

Ser Leu Gln Gln Thr Val Thr Glu Pro Lys Ala Val Glu Lys Glu Ser
            355                 360                 365

Glu Glu Thr Glu Glu Lys Thr Ser Glu Leu Asp Ile Leu Lys Leu Phe
            370                 375                 380

Lys Pro Glu Ser Leu Asn Cys Ser Leu Glu Ser Ser Thr Leu Tyr Asn
385                 390                 395                 400

Lys Leu Lys Glu Glu Pro Glu Ala Leu Thr Val Leu Ala Pro Ala Ala
                405                 410                 415

Gly Asp Ala Ile Ile Ser Leu Asp Phe Asn Asn Ser Ser Asp Ile
            420                 425                 430

Gln Leu Leu Lys Glu Val Pro Leu Tyr Asn Asp Val Met Leu Pro Ser
            435                 440                 445

Ser Ser Glu Lys Leu Pro Leu Ser Leu Ser Pro Leu Thr Pro Ser Asp
    450                 455                 460

Ser Leu Ser Ser His Ala Thr Thr Ala Lys Ser Thr Leu Pro Cys Arg
465                 470                 475                 480

Arg Arg His Pro Gly Pro Leu His Pro Tyr Thr Cys Cys Arg Arg Cys
                485                 490                 495

Ala Val His Leu Ser Arg Ser Ser Val Ala Val Gly Met Pro His Leu
            500                 505                 510

Phe Asp Pro Ala Pro His Arg Ala Ala Val Ser Ser Thr Thr Glu Lys
            515                 520                 525

Cys Leu Gln Arg Cys
    530

<210> SEQ ID NO 16
<211> LENGTH: 805
<212> TYPE: PRT
<213> ORGANISM: Xenopus laevis

<400> SEQUENCE: 16

Met Glu Gly Ser Val Val Ser Glu Lys Lys Arg Ile Ser Ser Glu
1               5                   10                  15

Arg Arg Lys Glu Lys Ser Arg Asp Ala Ala Arg Cys Arg Arg Ser Asn
                20                  25                  30

Glu Ser Glu Val Phe Tyr Glu Leu Ser His Glu Leu Pro Leu Pro His
            35                  40                  45

Asn Val Ser Ser His Leu Asp Lys Ala Ser Ile Met Arg Leu Asp His
    50                  55                  60

Gln Leu Pro Ala Val Glu Lys Val Ala Asp Ala Gly Asp Leu Asp Gly
65                  70                  75                  80

Glu Thr Glu Leu Asp Lys Gln Leu Asn Cys Phe Tyr Leu Lys Ala Leu
                85                  90                  95

Glu Gly Phe Val Leu Val Leu Thr Glu Glu Gly Asp Met Ile Tyr Leu
            100                 105                 110

Ser Glu Asn Val Asn Lys Cys Met Gly Leu Thr Gln Phe Glu Leu Thr
            115                 120                 125

Gly His Ser Val Phe Asp Phe Thr His Pro Cys Asp His Glu Glu Leu
            130                 135                 140

Arg Glu Met Leu Thr Phe Arg Asn Gly Pro Ala Lys Lys Arg Lys Arg
145                 150                 155                 160

Thr Asn His Arg Glu Lys Phe Leu Pro Ser Tyr Glu Met Tyr Ile Asn
```

```
                   165                 170                 175
Gln Ser Trp Lys Asn Arg Glu Tyr Lys Val Ser His Met Glu Gly Pro
            180                 185                 190

Ser Leu Tyr Arg Thr His Ala Cys Ile Tyr Asp Asn Ala Asn Asn Gln
            195                 200                 205

Asn His Cys Gly Tyr Lys Lys Pro Pro Met Thr Cys Met Val Val Ile
            210                 215                 220

Cys Glu Pro Ile Pro His Pro Ser Asn Ile Glu Phe Pro Leu Asp Ser
225                 230                 235                 240

Lys Thr Phe Leu Ser Arg His Ser Leu Asp Met Lys Phe Ser Tyr Cys
                245                 250                 255

Asp Glu Arg Val Thr Glu Leu Val Gly Tyr Glu Pro Asp Glu Leu Leu
                260                 265                 270

Gly Arg Ser Val Tyr Glu Tyr Tyr His Ala Leu Asp Ser Asp His Leu
            275                 280                 285

Thr Lys Pro Asn Tyr Asn Met Phe Thr Lys Gly Gln Val Thr Thr Gly
            290                 295                 300

Gln Tyr Arg Met Leu Ala Lys Lys Gly Gly Tyr Val Trp Val Glu Thr
305                 310                 315                 320

Gln Ala Thr Val Ile Tyr Asn Ser Lys Asn Ser Gln Pro Gln Cys Ile
                325                 330                 335

Val Cys Val Asn Tyr Val Leu Ser Glu Val Val Glu Lys Asp Leu Ile
                340                 345                 350

Leu Ser Leu Gly Gln Thr Ala Ser Val Leu Ile Pro Val Glu Ser Gln
            355                 360                 365

Glu Ile Lys Met Pro Glu Ile Phe Thr Glu Leu Asn Glu Glu Asn Asn
370                 375                 380

Ser Glu Cys Leu Phe Asp Lys Leu Lys Gln Glu Pro Gly Ser Leu Thr
385                 390                 395                 400

Val Leu Ala Pro Asp Ala Gly Asp Glu Ile Ile Pro Leu Asp Phe Ser
                405                 410                 415

Ser Gly Asp Ser Asp Lys Pro Tyr Glu Asp Val Pro Leu Tyr Asn Asp
                420                 425                 430

Val Met Leu His Ser Thr Ser Asn Lys Leu Glu Ser Thr Pro Ile Thr
                435                 440                 445

Pro Leu Pro Ala Pro Glu Met Pro Lys Pro Leu Arg Ser Asn Val Asp
            450                 455                 460

Pro Ala Leu Asn Arg Glu Val Val Ile Lys Met Glu Ser Asn Pro Arg
465                 470                 475                 480

Thr Thr Cys Ala Ser Ile His His Ser Thr Ala Ile Gln Ala Arg Gln
                485                 490                 495

Pro Phe Arg Tyr Gln Phe Gln Ser Glu Pro Ser Thr Glu Pro Asn Thr
            500                 505                 510

Pro Glu Tyr Cys Phe Asp Val Asp Ser Glu Met Ala Ser Glu Phe Lys
            515                 520                 525

Leu Asp Leu Val Glu Lys Leu Phe Ala Ile Asp Thr Glu Ala Lys Ala
            530                 535                 540

Pro Phe Tyr Tyr Pro Gly Asn Asp Leu Asp Leu Glu Met Leu Ala Pro
545                 550                 555                 560

Tyr Ile Pro Met Asp Asp Asp Phe Gln Leu Arg Thr Phe Asp Gln Leu
                565                 570                 575

Ser Ser Leu Glu Cys Asp Ser Ser Ile Pro Gln Thr Leu Gly Ser Met
            580                 585                 590
```

```
Thr Thr Leu Phe His Gln Ser Leu Ser Pro Ser Thr Ser Asp Phe Lys
        595                 600                 605

Pro Glu Asp Ala Met Ser Asp Leu Lys Thr Ile Ile Gln Ser Pro Val
610                 615                 620

His Met Met Lys Glu Ser Thr Ser Ala Pro Val Ser Pro Tyr Asn Gly
625                 630                 635                 640

Asn Arg Ser Arg Thr Ser Ser Pro Val Arg Pro Ala Lys Ala Val Val
                645                 650                 655

Asp Lys Thr Glu Lys Ser Arg Pro Gly Thr Pro Asn Leu Pro Val Pro
                660                 665                 670

Leu Asn Lys Arg Cys Thr Ile Leu Asp Glu Glu Leu Asn Pro Lys Met
                675                 680                 685

Ile Cys Phe Thr Gln Cys Thr Ala Glu Lys Arg Lys Met Glu Ser Asp
            690                 695                 700

Gly Pro Leu Phe Gln Ala Ile Gly Ile Gly Thr Leu Phe Gln Thr Asn
705                 710                 715                 720

Val Asp Pro Gly Pro Asn Ser Ser Leu Gln Trp Lys Arg Val Lys Gly
                725                 730                 735

Ser Asp Ser Glu Arg Leu Ser Ser Ala Glu Gln Arg Thr Ile Leu Leu
                740                 745                 750

Leu Ser Thr Asp Met Ala Ser Gln Leu Leu Gly Gln Ser Phe Asp Gly
            755                 760                 765

Thr Val Leu Pro Gln Leu Thr Gly Tyr Asp Cys Glu Val Asn Ala Pro
        770                 775                 780

Val His Gly Thr Arg Asn Leu Leu Gln Gly Glu Glu Leu Leu Arg Ala
785                 790                 795                 800

Leu Asp Gln Ala Asn
                805

<210> SEQ ID NO 17
<211> LENGTH: 21
<212> TYPE: DNA
<213> ORGANISM: Artificial Sequence
<220> FEATURE:
<223> OTHER INFORMATION: siRNA directed against mouse VHL factor,
      including 3' AT

<400> SEQUENCE: 17
aacatcacat tgccagtgta t                                              21

<210> SEQ ID NO 18
<211> LENGTH: 15
<212> TYPE: PRT
<213> ORGANISM: Homo sapiens

<400> SEQUENCE: 18

Pro Asn Ser Pro Ser Glu Tyr Cys Phe Tyr Val Asp Ser Asp Met
1               5                   10                  15

<210> SEQ ID NO 19
<211> LENGTH: 15
<212> TYPE: PRT
<213> ORGANISM: Mus musculus

<400> SEQUENCE: 19

Pro Asn Ser Pro Ser Glu Tyr Cys Phe Asp Val Asp Ser Asp Met
1               5                   10                  15
```

```
<210> SEQ ID NO 20
<211> LENGTH: 15
<212> TYPE: PRT
<213> ORGANISM: Carassius carassius

<400> SEQUENCE: 20

Pro Asn Ser Pro Met Glu Tyr Cys Phe Gln Val Asp Ser Asp Ile
1               5                   10                  15

<210> SEQ ID NO 21
<211> LENGTH: 15
<212> TYPE: PRT
<213> ORGANISM: Xenopus laevis

<400> SEQUENCE: 21

Glu Pro Asn Thr Pro Glu Tyr Cys Phe Asp Val Asp Ser Glu Met
1               5                   10                  15
```